(12) United States Patent
Diaz et al.

(10) Patent No.: US 9,121,778 B2
(45) Date of Patent: *Sep. 1, 2015

(54) APPARATUS FOR DETERMINING DEFORMATION RESPONSE

(75) Inventors: Troy Diaz, Fort Collins, CO (US); Kevin N. Albertsen, Fort Collins, CO (US); Josh Landrum, Fort Collins, CO (US); Jean-Jacques Brun, Fort Collins, CO (US); Brett A. Tatman, Fort Collins, CO (US)

(73) Assignee: Snaptron, Inc., Windsor, CO (US)

( * ) Notice: Subject to any disclaimer, the term of this patent is extended or adjusted under 35 U.S.C. 154(b) by 128 days.

This patent is subject to a terminal disclaimer.

(21) Appl. No.: 13/439,520

(22) Filed: Apr. 4, 2012

(65) Prior Publication Data

US 2012/0247192 A1    Oct. 4, 2012

Related U.S. Application Data

(63) Continuation of application No. 12/663,836, filed as application No. PCT/US2008/066596 on Jun. 11, 2008, now Pat. No. 8,156,825.

(60) Provisional application No. 60/934,210, filed on Jun. 11, 2007.

(51) Int. Cl.
*G01L 1/04* (2006.01)
*G01L 5/00* (2006.01)
*G01N 3/42* (2006.01)

(52) U.S. Cl.
CPC ............... *G01L 5/0038* (2013.01); *G01N 3/42* (2013.01); *G01N 2203/0082* (2013.01); *G01N 2203/0286* (2013.01)

(58) Field of Classification Search
USPC ..................... 73/760, 849, 862.621
See application file for complete search history.

(56) References Cited

U.S. PATENT DOCUMENTS

| 4,403,499 A | 9/1983 | Sack et al. |
| 5,029,029 A | 7/1991 | Hatchett et al. |

(Continued)

FOREIGN PATENT DOCUMENTS

| WO | 2002073162 A2 | 9/2002 |
| WO | 2006071240 A1 | 7/2006 |

OTHER PUBLICATIONS

ASTM F2592-07—Standard Test Method for Measuring the Force-displacement of a Membrane Switch, Jul. 2, 2007.

(Continued)

*Primary Examiner* — Max Noori
(74) *Attorney, Agent, or Firm* — Santangelo Law Offices, P.C.

(57) ABSTRACT

One aspect of the inventive technology may be generally described as a method for determining test object deformation response that comprises the steps of moving a deformation force deliverer 1 to deliver deformation force 24 to a test object 3; adjusting a deformation force deliverer affecting input so as to meet at least one constraint while performing the step of moving the deformation force deliverer 1; deforming the test object 3 with the deformation force 24; and determining test object response to the deformation force. Corollary apparatus, in addition to other inventive apparatus and method aspects relating variously to test object deformation response determination are part of the inventive technology. Such aspects may relate to the use of a linear actuator 15 in a test object deformation and to identity of motion of a deformation force deliverer 3 and a force deliverer drive component 75, as herein described.

49 Claims, 49 Drawing Sheets

(56) References Cited

U.S. PATENT DOCUMENTS

| | | | |
|---|---|---|---|
| 5,103,682 | A | 4/1992 | Moreland |
| 5,117,189 | A | 5/1992 | Terminiello et al. |
| 5,130,506 | A | 7/1992 | Zuercher et al. |
| 5,388,467 | A | 2/1995 | Jereb et al. |
| 5,616,857 | A * | 4/1997 | Merck et al. ............ 73/82 |
| 5,918,266 | A | 6/1999 | Robinson |
| 6,142,010 | A * | 11/2000 | Merck et al. ............ 73/81 |
| 6,332,364 | B1 | 12/2001 | Buschmann et al. |
| 6,484,586 | B1 | 11/2002 | Dutoit et al. |
| 6,615,680 | B1 | 9/2003 | Dahlstrom et al. |
| 6,623,326 | B2 | 9/2003 | Judkins |
| 6,900,641 | B2 | 5/2005 | Draggie et al. |
| 6,999,162 | B1 | 2/2006 | Takahaski |
| 7,141,963 | B1 | 11/2006 | Rankin, II et al. |
| 7,327,054 | B2 | 2/2008 | Ng et al. |
| 7,328,626 | B2 * | 2/2008 | Beller et al. ............ 73/861 |
| 8,156,825 | B2 * | 4/2012 | Diaz et al. ............ 73/862.621 |
| 2004/0134263 | A1 * | 7/2004 | Tsujii et al. ............ 73/81 |
| 2009/0230338 | A1 | 9/2009 | Sanders et al. |
| 2010/0170348 | A1 | 7/2010 | Diaz et al. |
| 2013/0173199 | A1 * | 7/2013 | Guasco ............ 702/95 |

OTHER PUBLICATIONS

Tricor Model 933 Lifecycle Test System; www.tricor-systems.com/products/spec/prod933.htm; May 24, 2007.
Tricor Model 911 Automated Keyboard and LED Test System; www.tricor-systems.com/products/spec/prod911.htm; May 24, 2007.
Tricor Model 913 LED & Keyboard Switch Test System; www.tricor-systems.com/products/spec/prod913.htm; May 24, 2007.
Tricor Model 921 Force Displacement and Switch Test Station; www.tricor-systems.com/products/spec/prod921.htm; May 24, 2007.
Tricor Model 921xy Automated Keyboard Test System; www.tricor-systems.com/products/spec/prod921xy.htm; May 24, 2007.
Tricor Model 951 Displacement Force Resistance Test Station; www.tricor-systems.com/products/spec/prod951.htm; May 24, 2007.
Tricor Model 961 Displacement Force Resistance Test Station; www.tricor-systems.com/products/spec/prod961.htm; May 24, 2007.
U.S. Appl. No. 60/934,210, filed Jun. 11, 2007.
International Search Report dated Oct. 31, 2008 for International Application No. PCT/US08/66596.
Written Opinion of International Searching Authority dated Oct. 31, 2008 for International Application No. PCT/US08/66596.
International Preliminary Report on Patentability dated Jun. 9, 2009 for International Application No. PCT/US08/66596.
U.S. Appl. No. 12/663,836, filed Dec. 9, 2009.

\* cited by examiner

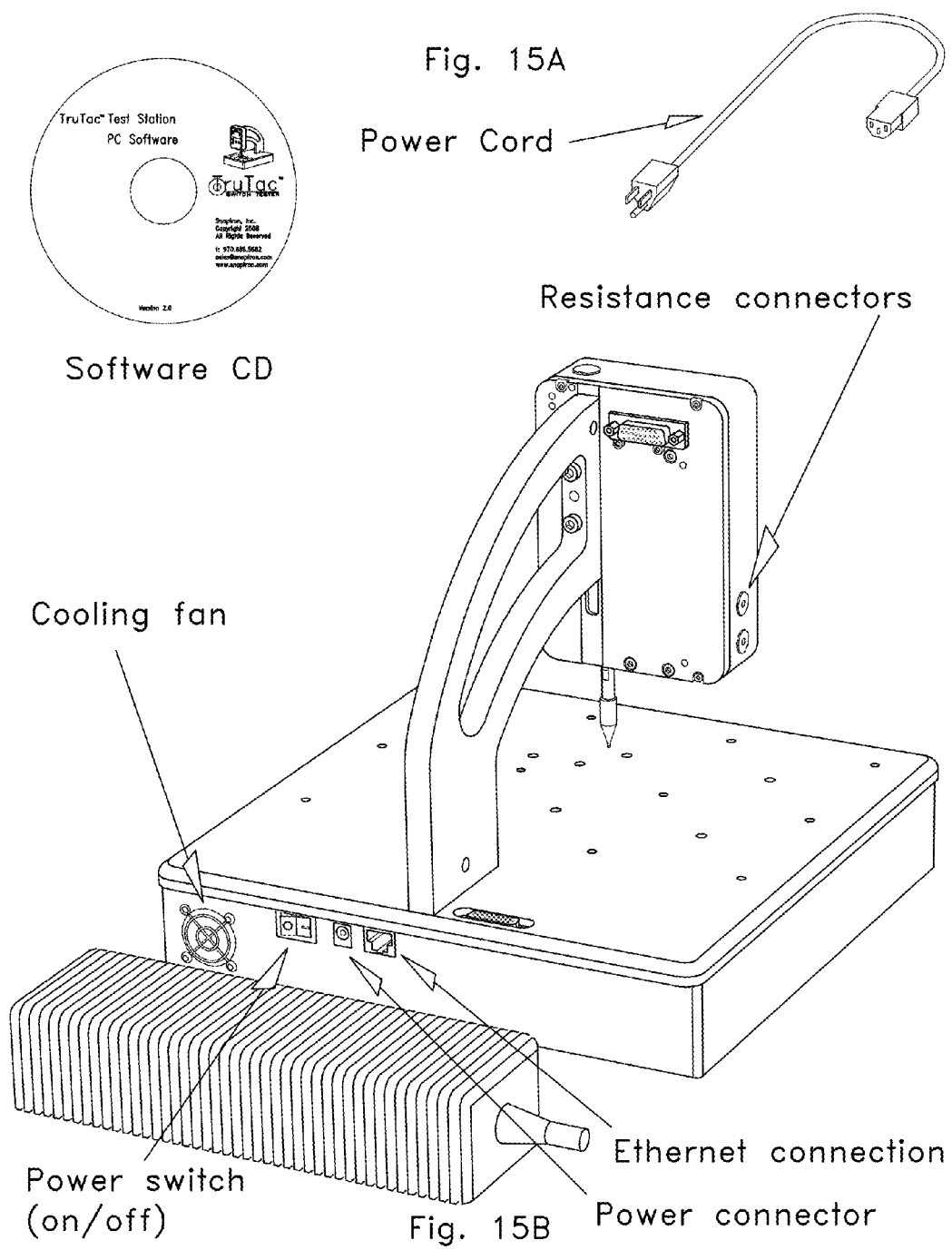

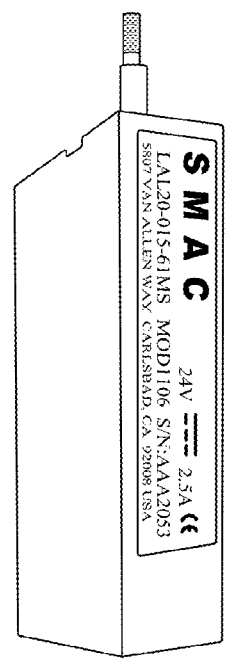 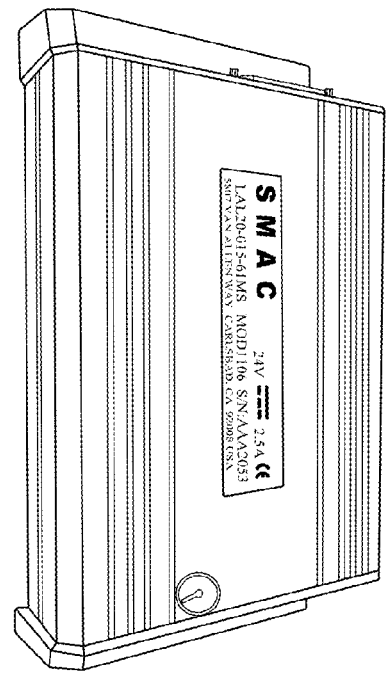
Fig. 17A　　　　　　　　Fig. 17B
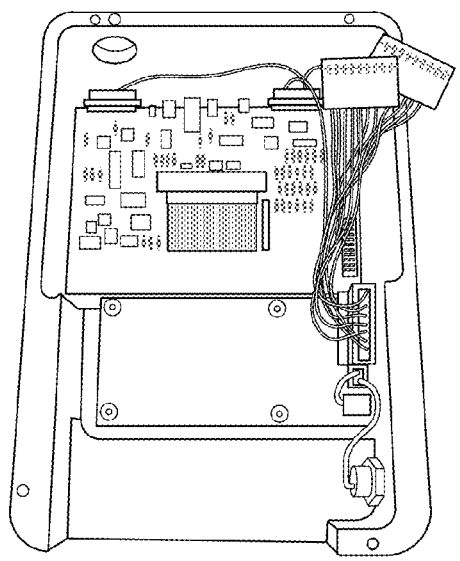 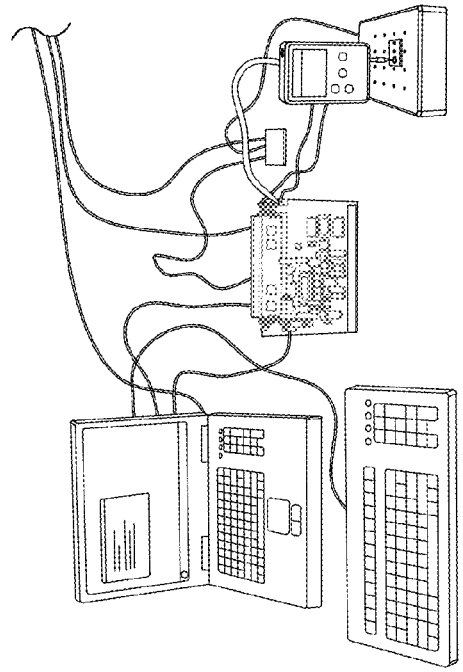
Fig. 17C　　　　　　　　Fig. 17D

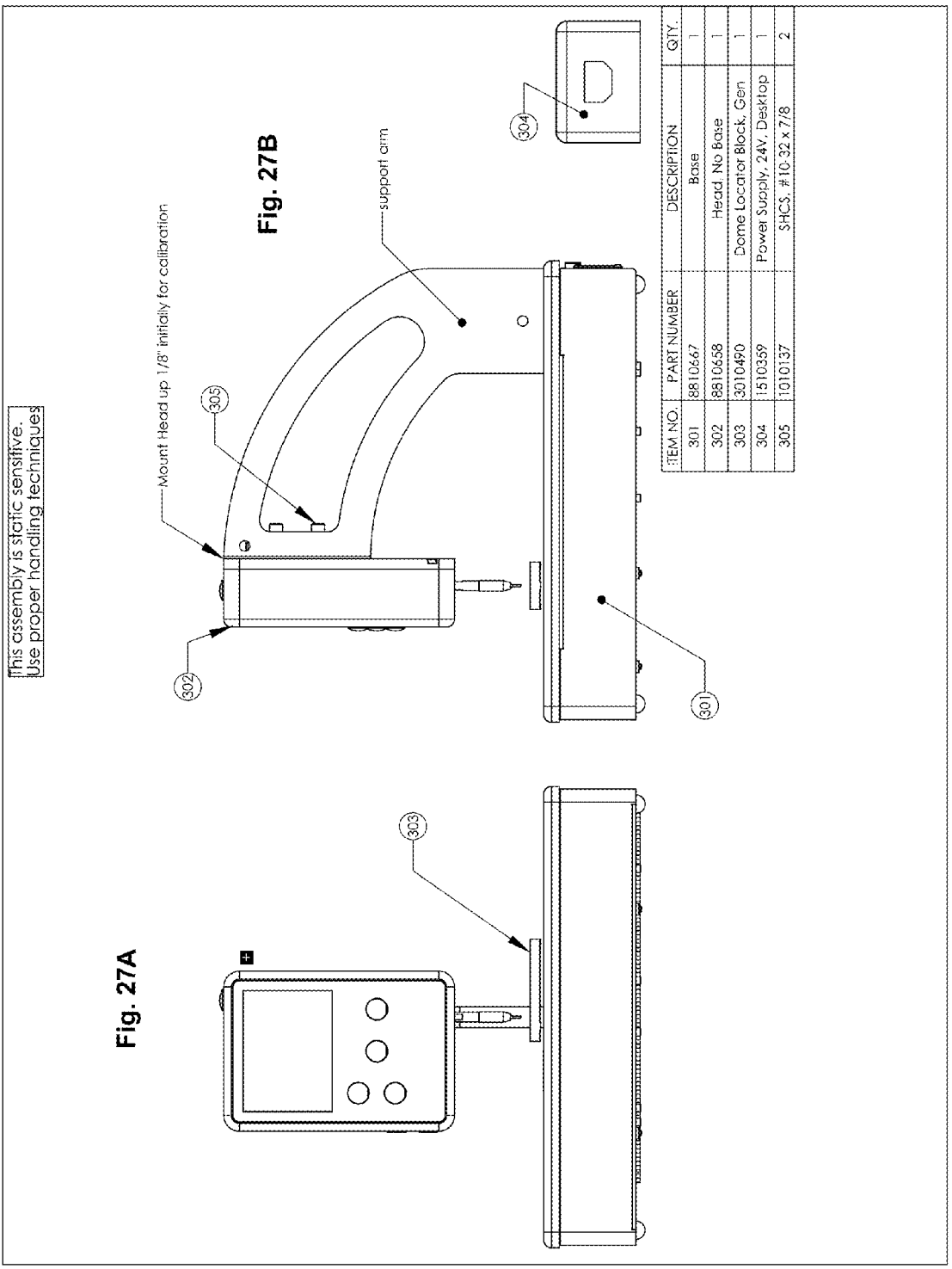

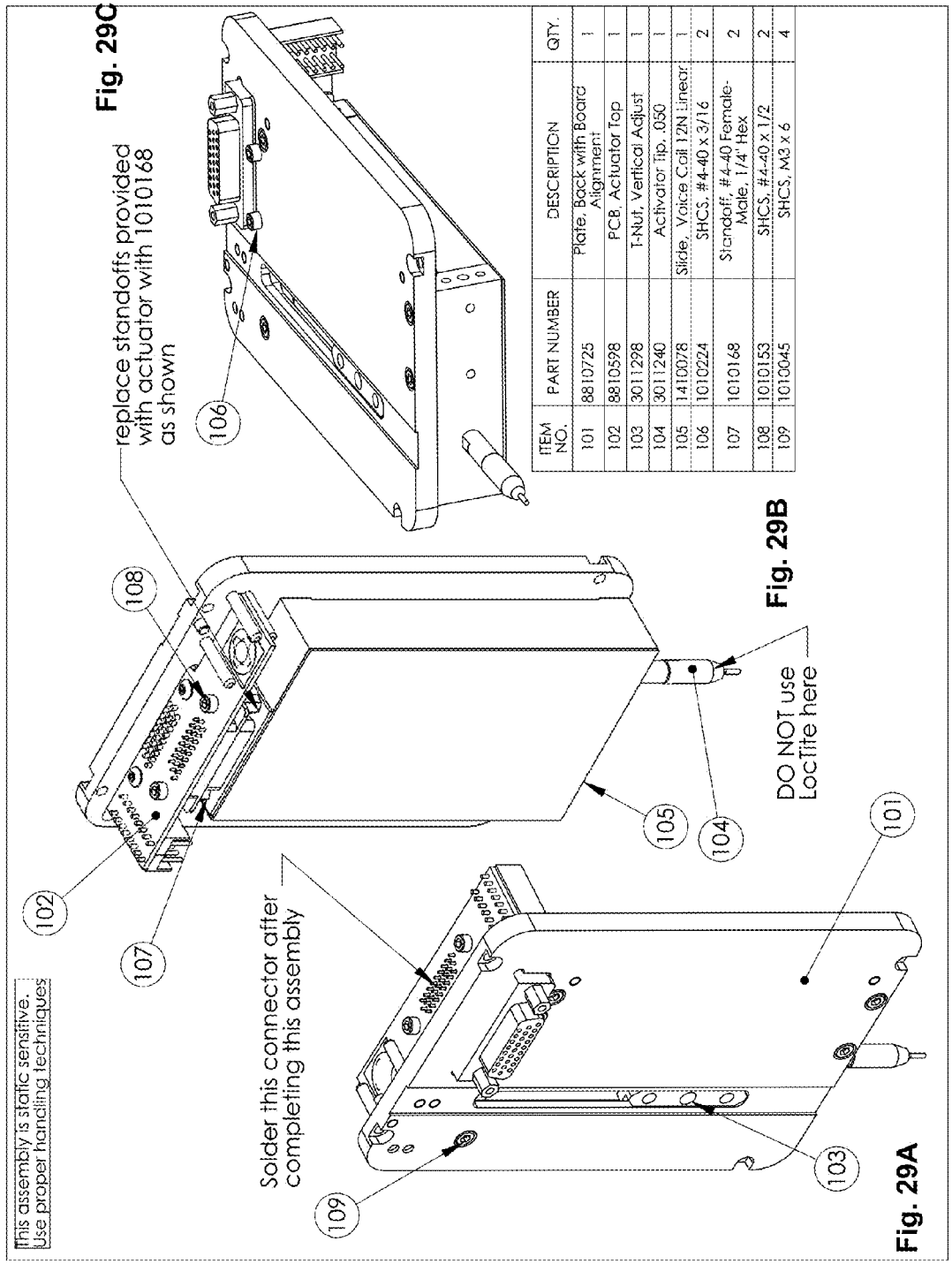

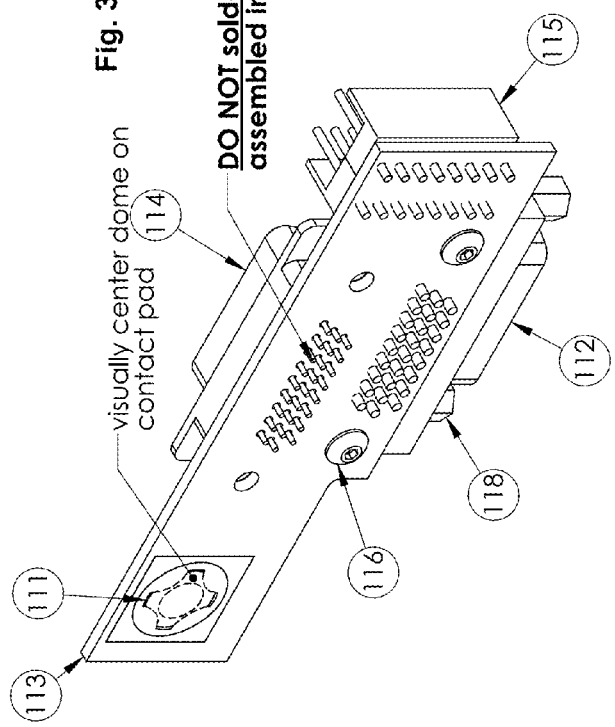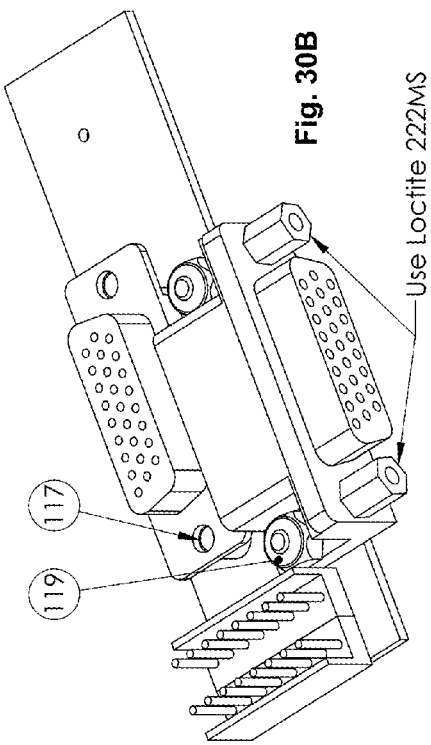

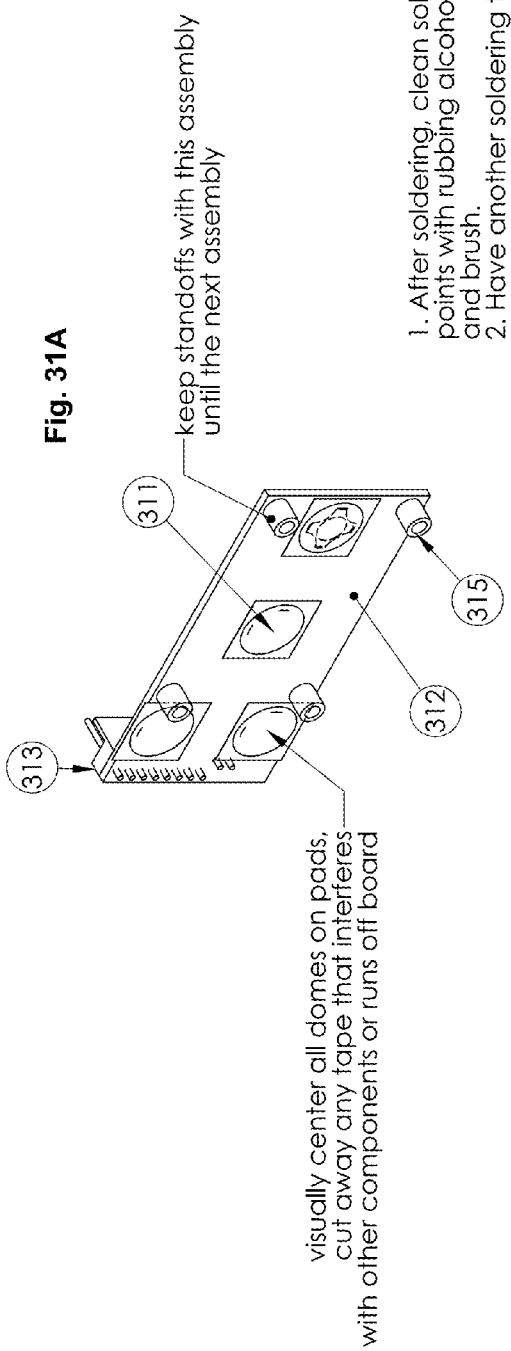
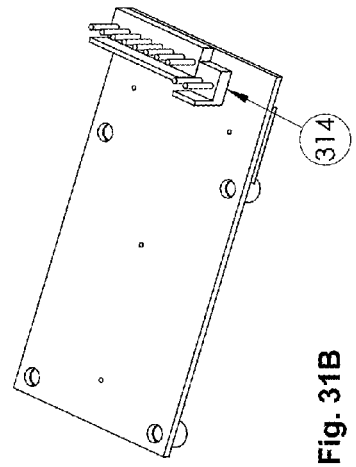
Fig. 31A
Fig. 31B

Instructions for etching TruTac Buttons
1. On the proto laser computer, open the relevant etching file
2. Pound down all the pins in the laser platform.
3. Insert a sheet of 10 mil poly over the std seal area
4. cut only the green at 30%, 100% speed and a pulse width of 3
5. Remove both sides of the poly and discard the outside piece
6. Insert the std seal pins in the plate
7. fit the small piece of poly on the pins
8. cut only the red at 30% power, 100% speed and a pulse width of 3
9. remove the poly form the pins and remove the cut out pieces from the plate
10. reinstall the poly to the pins and insert the buttons into the holes you just cut in the poly
11. set the height of the table to the top of the buttons
12. cut only the black layer at 3% power, 75% speed, and a pulse width of 3

Laser mark character here
as needed for next assembly.
Do laser operation before
attaching bumper part.

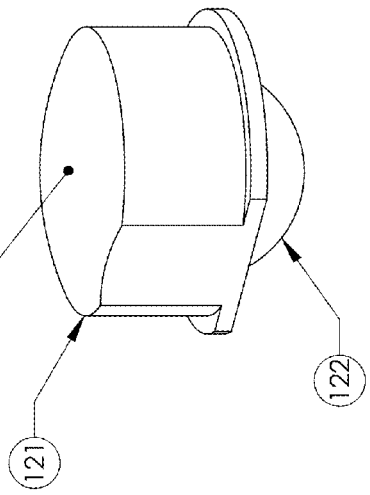

| ITEM NO. | PART NUMBER | DESCRIPTION | QTY. |
|---|---|---|---|
| 121 | 3011309 | Button, Concentrator 1/2" | 1 |
| 122 | 1210235 | Bumper, Adhesive Backed | 1 |

Fig. 32

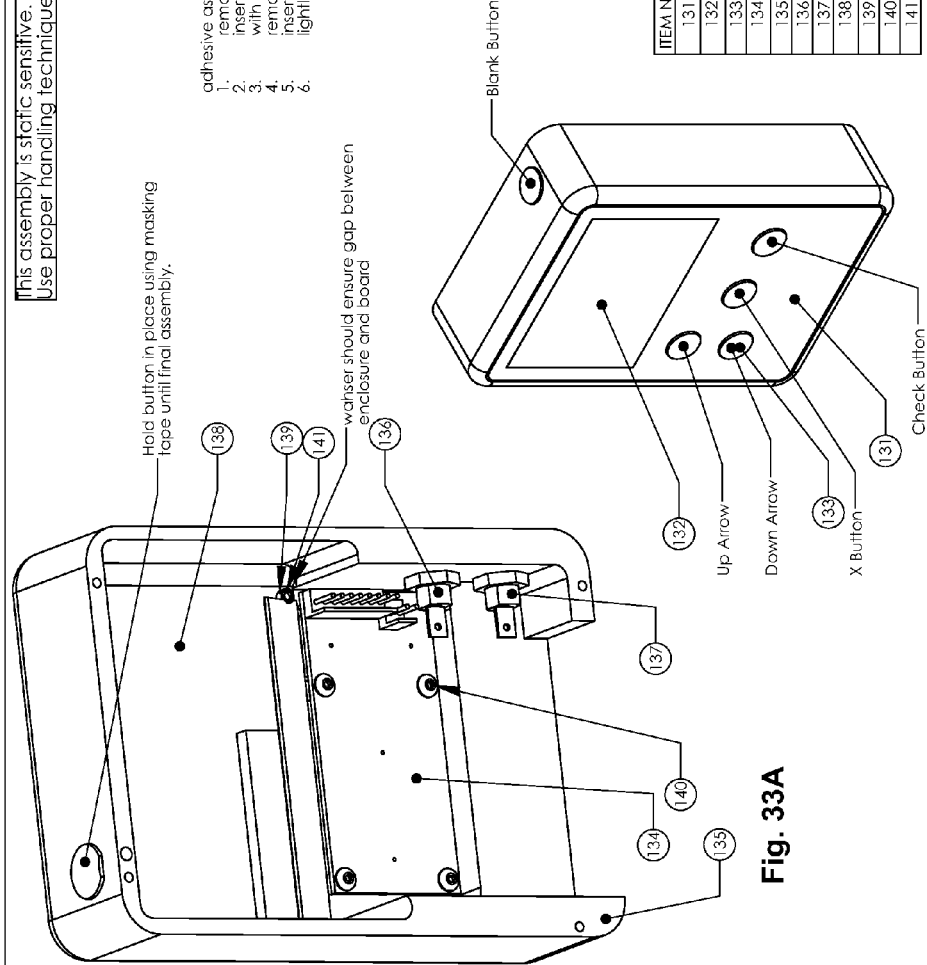

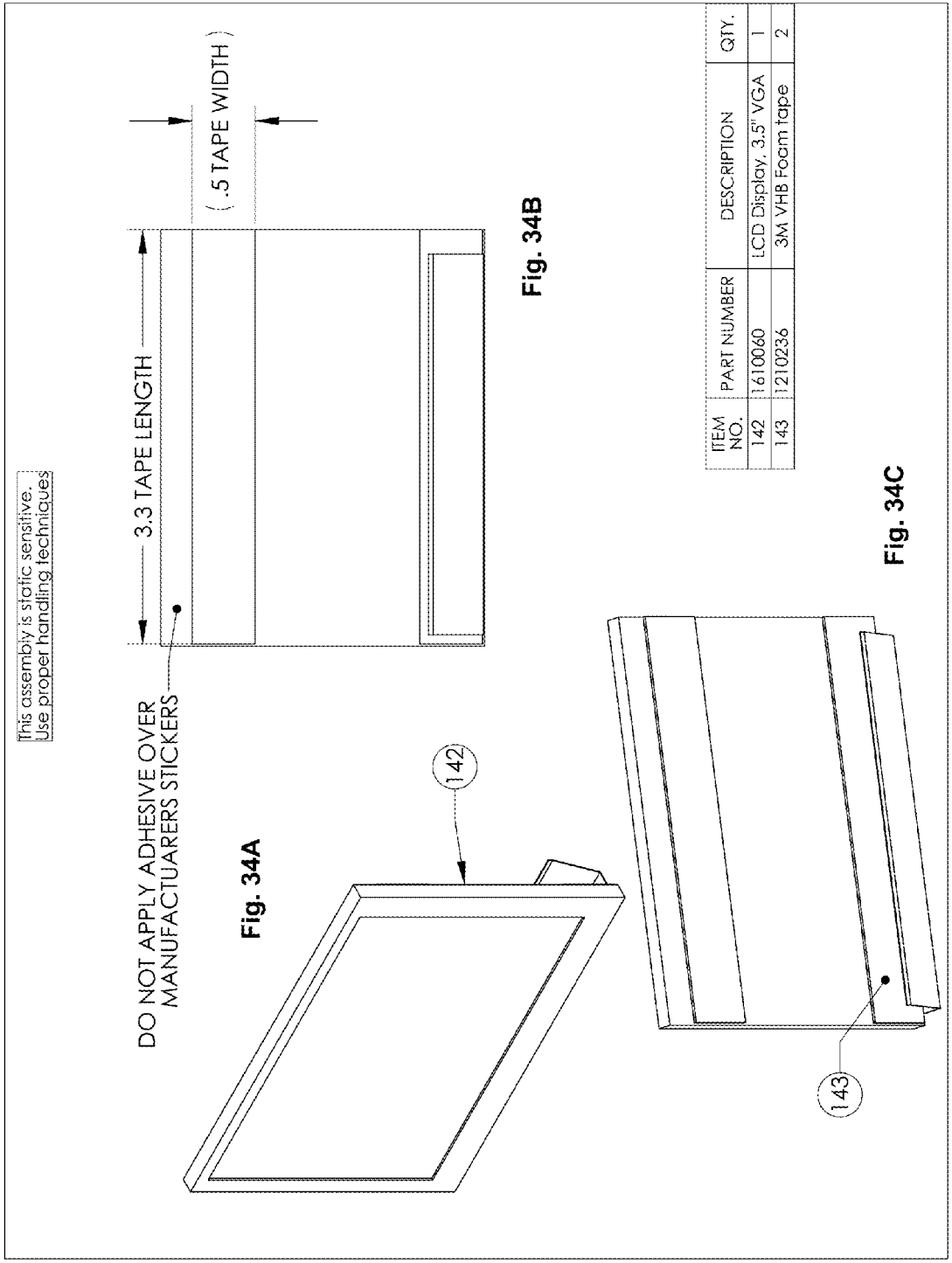

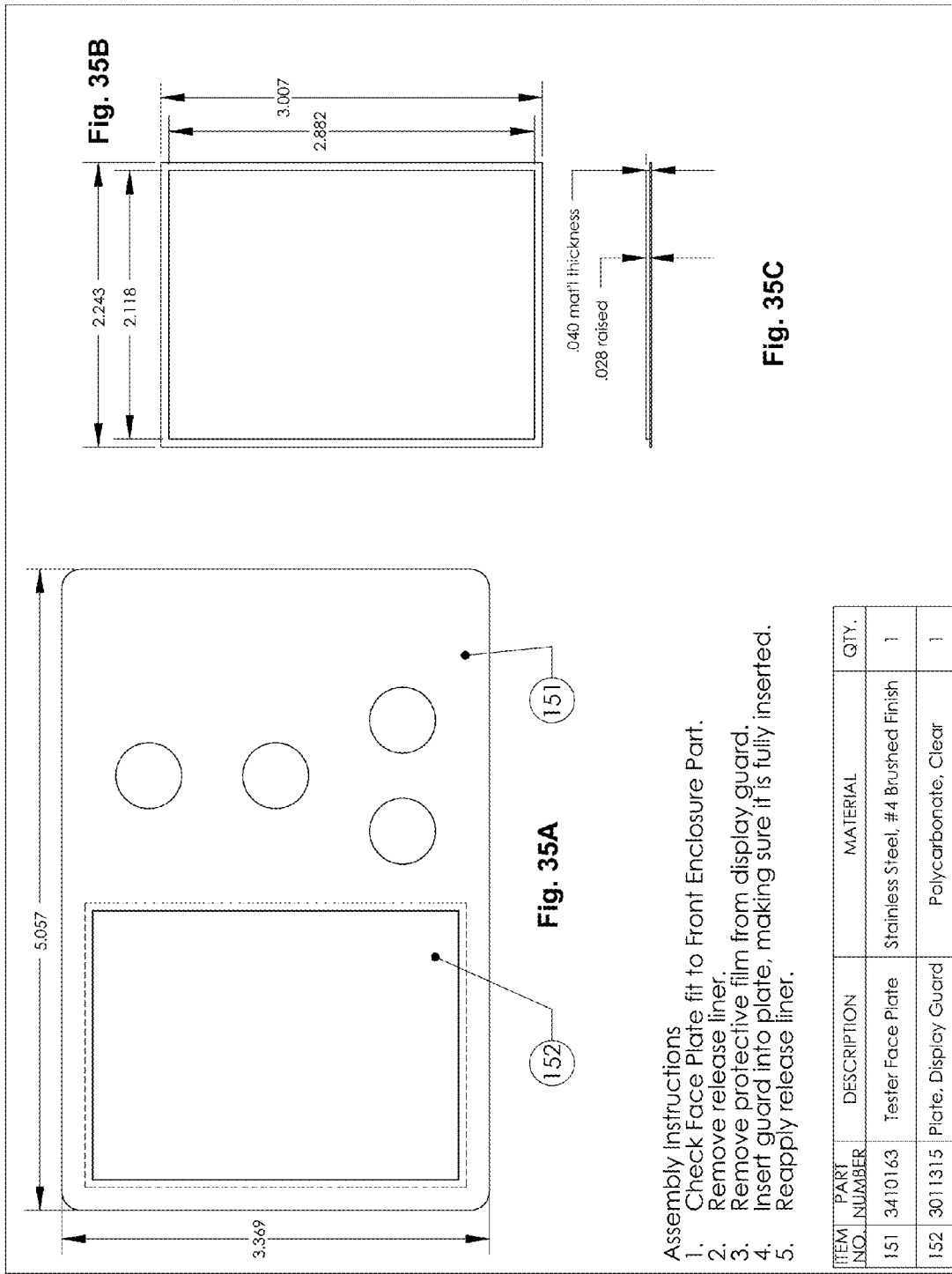

Tie back cables as shown to avoid interfering with 4 mounting holes.

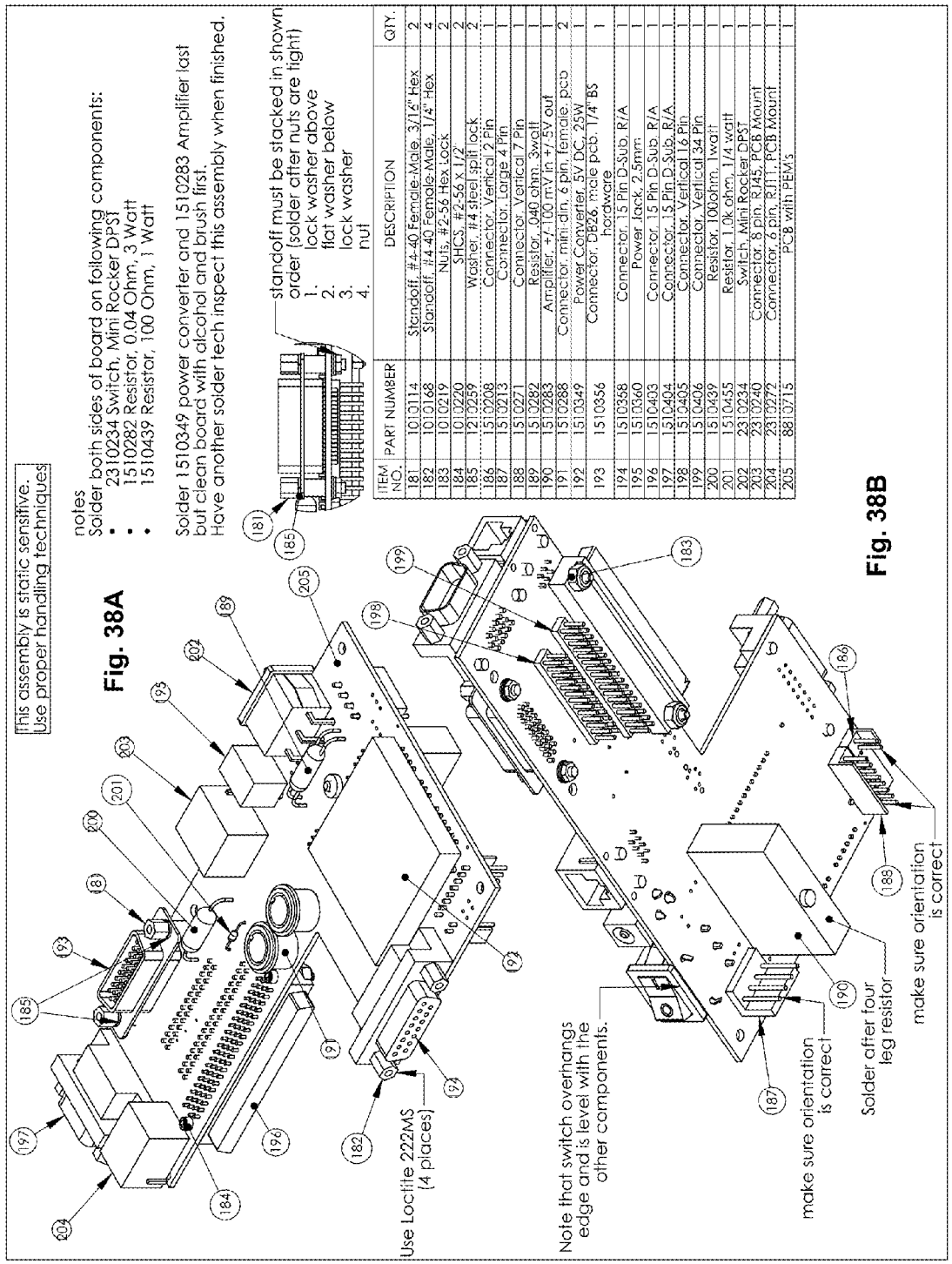

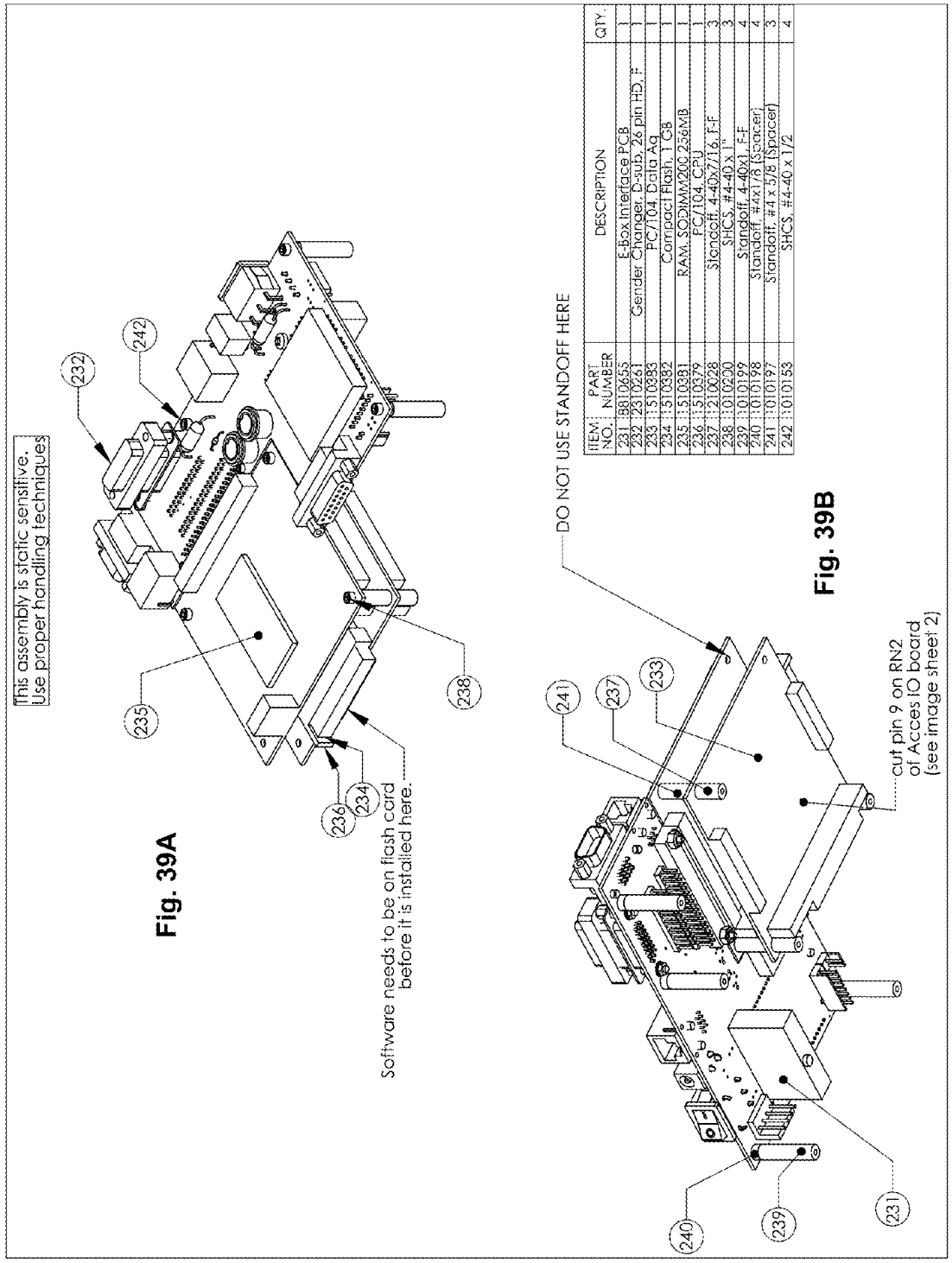

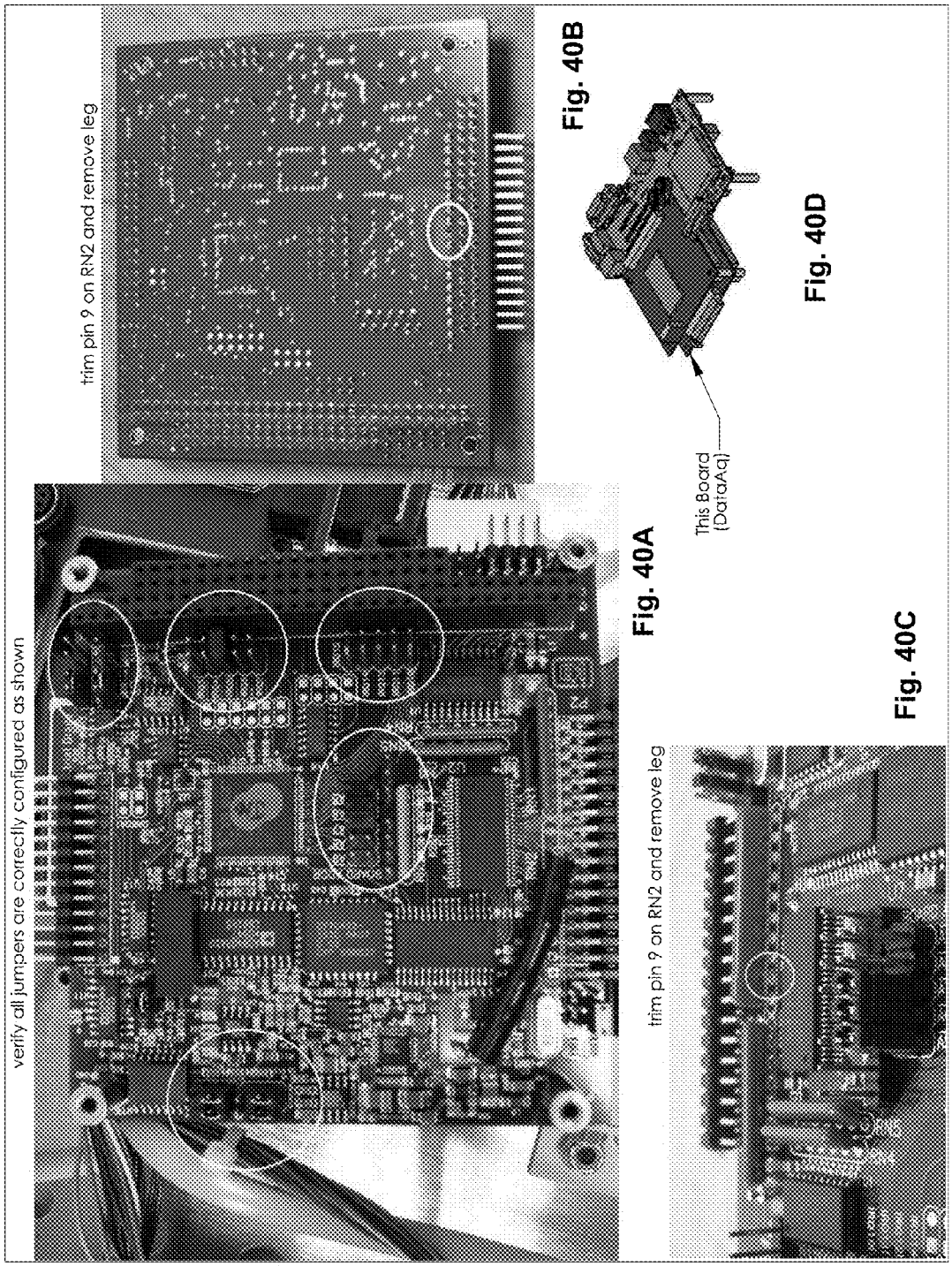

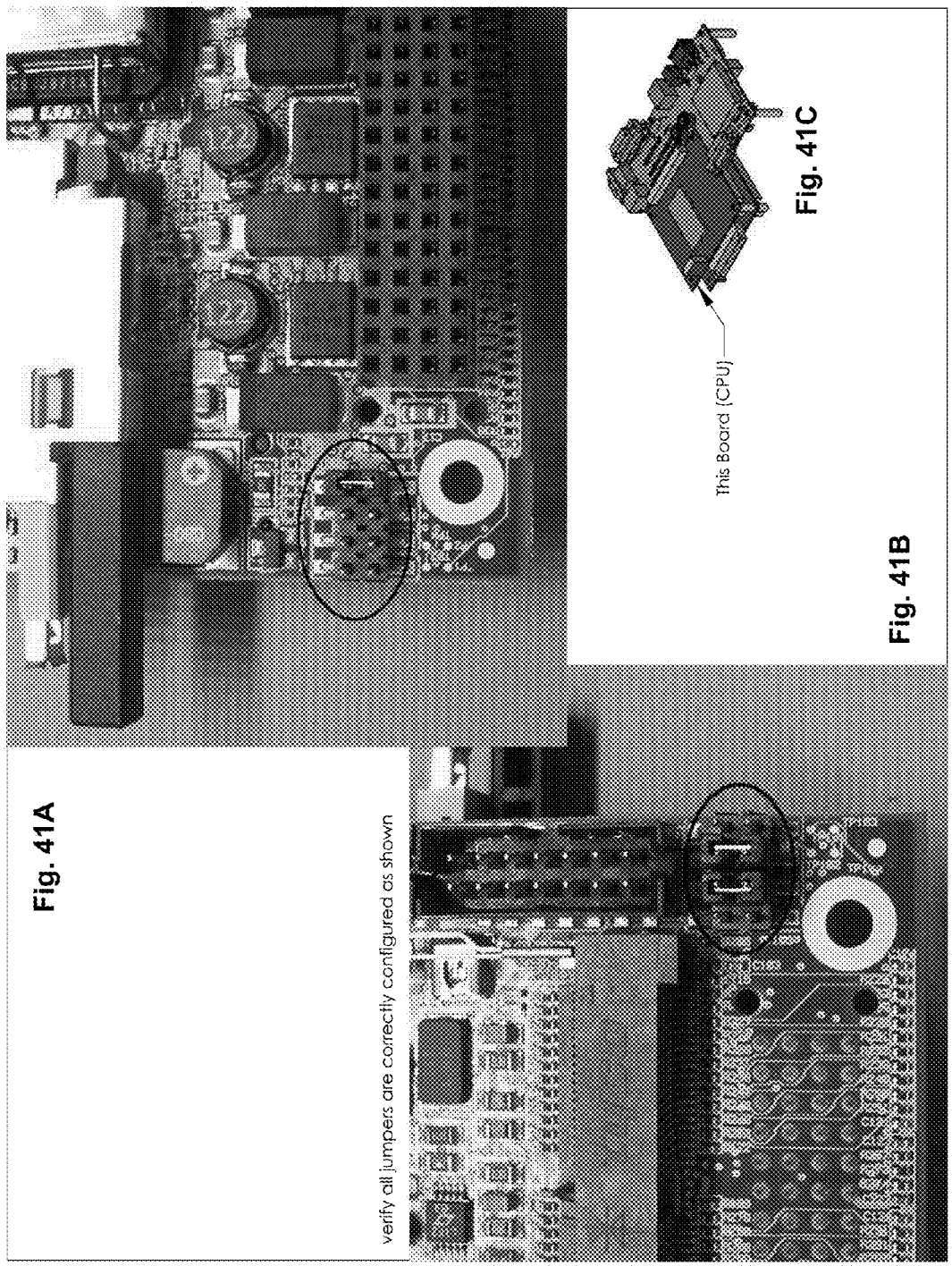

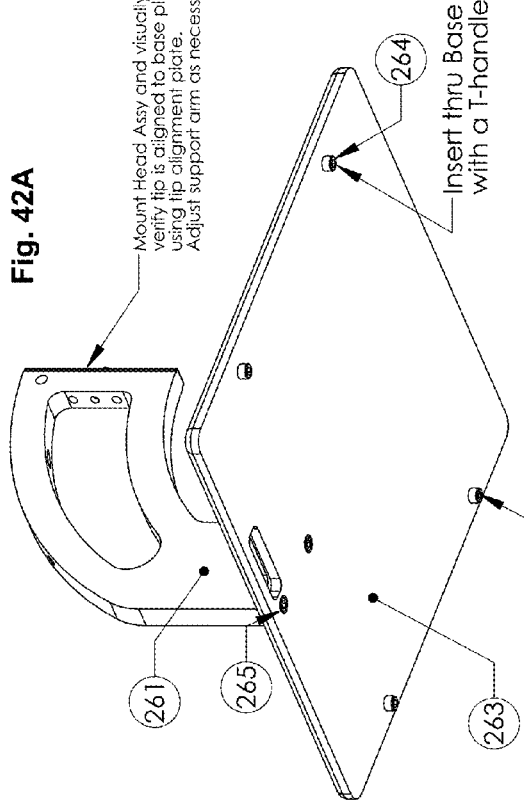
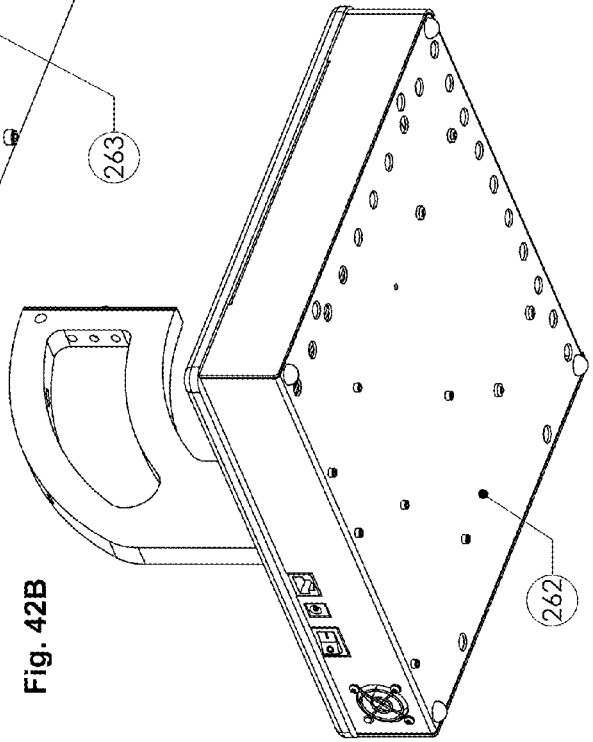
Fig. 42A
Fig. 42B

| ITEM NO. | PART NUMBER | DESCRIPTION | QTY. |
|---|---|---|---|
| 281 | 3011297 | Arm, support | 1 |
| 282 | 1110086 | Dowel Pin, 3/16 x 3/4 | 1 |

.188±.020 press pin

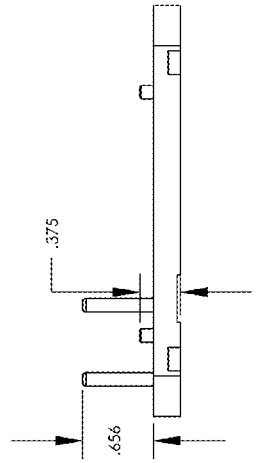
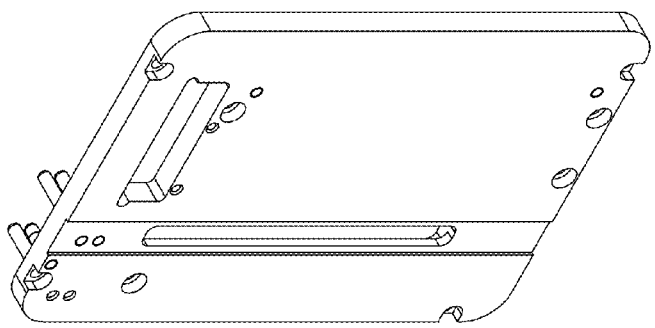
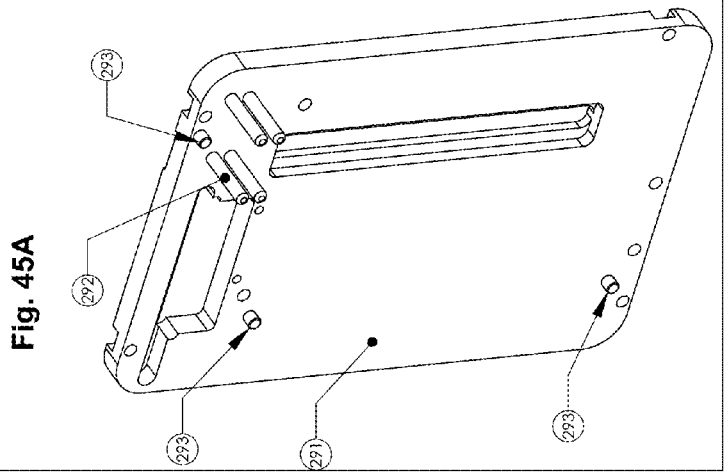

APPARATUS FOR DETERMINING DEFORMATION RESPONSE

This application is a continuation application of, and claims benefit of and priority to, U.S. patent application Ser. No. 12/663,836, issuing on Apr. 17, 2012 as U.S. Pat. No. 8,156,825, said application filed Dec. 9, 2009 (published as publication number US 2010/0170348 A1 on Jul. 8, 2010), which itself is the United States National Stage of international patent application number PCT/US2008/066596, filed Jun. 11, 2008 (published as WO 2008/154598 A2 on Dec. 18, 2008), which itself claims priority to and benefit of U.S. Provisional application 60/934,210, filed Jun. 11, 2007, all of said applications hereby incorporated herein in their entirety.

TECHNICAL FIELD

Generally, the inventive technology may find application in the field of testing of objects for response to a deformation. In particular, the inventive technology may find application whenever information relative to deformation response, including but not limited to deformation force vs. deformation position, life cycle response, and/or application specific responses (e.g., electrical switch performance), is valuable.

BACKGROUND

Materials exhibit deformation in response to a force. The amount of force necessary to generate a specific deformation, the speed of deformation at a specific position between undeformed and maximally deformed position, the onset of plastic deformation, are just three of many parameters that may characterize deformation response of a test object. Depending on the specific test object, other parameters, such as electrical resistance in the case of force activated electrical switch domes (which may be pressed by an operator to input data and may be found in a variety of electrical appliances and devices) may reveal valuable information about its switch-related functionality (e.g., will it function as a switch after 1,000,000 cycles?). Deformation force vs. deformation position (also referred to as displacement, or travel in the industry) information may provide information relevant to the functionality, suitability and/or applicability of a variety of test objects, whether they be materials, devices, contiguities, etc.

A classic example of an apparatus adapted to test performance is switch dome testers, which may be adapted to test force vs. displacement (or deformation position), electrical response, or life cycle response in order to characterize functionality, suitability and/or applicability of existing or intended switch designs. The most predominant type of such tester include strain gauges established in a cantilevered bar adapted to exhibit an enhanced deformation (due to vacuations established at non-terminal portions of the cantilever) in response to a load applied at one end. A deformation drive is supplied at a non-terminal site of the cantilever such that the strain gauges are between such non-terminal site and that site from which a "finger" that delivers a deformation force to the dome below is located. Electrical readings from such gages can then be used to generate force vs. displacement (also known as travel or deformation or simply position) data. Notably, such apparatus do not adjust an input to meet a constraint, do not exhibit a drive component and force deliverer that move simultaneously at the same speed and acceleration, and do not use a linear actuator in any fashion. Further, such apparatus may be limited in applicability, accuracy, reliability, durability, cyclical speed, controllability and/or range of applied force.

It is a goal of at least one embodiment of the inventive technology to provide an apparatus and method that, with an enhanced (relative to prior art apparatus and methods) delivered force range and cyclical speed may have application not only in the field of switch dome testing but also in the field of testing for elastic response and hardness. Such enhanced ranges and speeds (e.g., in cycles per second and/or deformation speed) may be the result of the use of a voice coil based linear actuator. Indeed, embodiments of the inventive technology afford significant increases in cycles per second for reliability/life/cyclical response testing (greater than about 10 cycles per second, between about 10 to about 20 cycles per second, about 20 cycles per second, and, in certain embodiments, perhaps greater than about 20 cycles per second or more).

It is a goal of at least one embodiment of the inventive technology to provide an apparatus and method that relies on an input-based control scheme, thereby affording an enhanced level of control and one that, in particular embodiments, is more suited to certain types of testing, particularly those where accelerative and inertial effects may introduce error to test results.

It is a goal of at least one embodiment of the inventive technology to provide an apparatus and method that exhibits improved ability to recreate a test over several actuation cycles on different test objects (e.g., different force activated switch domes, or buttons).

It is a goal of at least one embodiment of the inventive technology to provide an apparatus and method that exhibits improved accuracy in control of testing parameters, particularly over many deformations (e.g., 100,000 cycles), and, in certain embodiments provide control sufficient to replicate actual deformation force characteristics (e.g., speed, acceleration, force) to improve characterization of response, whether in singular force application or cyclic testing mode.

It is a goal of at least one embodiment of the inventive technology to provide an apparatus and method that exhibits an improved ability to quantify reliability (e.g., the number of cycles until switch failure) of a test object designed to undergo cyclical deformation (e.g., a force activated switch dome).

It is a goal of at least one embodiment of the inventive technology to provide an apparatus and method that exhibits an improved ability to test mechanical response (mechanical decay) and electrical response (electrical decay) of, e.g., force activated switch domes, over repeated cyclic actuations.

Of course, other objects and advantages of the inventive technology may be disclosed in the sections that follow.

DISCLOSURE OF THE INVENTIVE TECHNOLOGY

One aspect of the inventive technology may be generally described as a method for determining test object deformation response that comprises the steps of moving a deformation force deliverer to deliver deformation force to a test object; adjusting a deformation force deliverer affecting input so as to meet at least one constraint while performing the step of moving the deformation force deliverer; deforming the test object with the deformation force; and determining test object response to the deformation force. Corollary apparatus, in addition to other inventive apparatus and method aspects, relating variously to test object deformation response determination are part of the inventive technology. Such aspects may relate to the use of a linear actuator in a test object deformation and to identity of motion of a deformation force deliverer and a force deliverer drive component, as herein described.

BRIEF DESCRIPTION OF THE DRAWINGS

FIG. 13C shows a closeup view of a deformation force deliverer in contact with a test object on a test object block locator while

FIG. 15A shows a power cord and software; FIG. 15B shows a rear perspective view of a test station embodiment of the inventive technology.

FIGS. 17A and B show side and top perspective views, respectively, of a servo-controller that may find application in the inventive technology. FIG. 17C shows electronics inside the interface of a test station embodiment of the inventive technology. FIG. 17D shows an exposed base, and internal componentry, as linked with a laptop computer and interface.

FIG. 27 shows a diagram of a test station embodiment of the inventive technology.

FIG. 29 shows an assembly diagram of a linear actuator that may find application in a test station embodiment of the inventive technology.

FIG. 30 shows an assembly diagram of a part of the interface of a test station embodiment of the inventive technology.

FIG. 31 shows an assembly diagram of a part of the interface of a test station embodiment of the inventive technology.

FIG. 32 shows an assembly diagram of button (switch dome) used as part of the interface of a test station embodiment of the inventive technology.

FIGS. 33A and 33B show assembly diagrams of a housing of the interface of a test station embodiment of the inventive technology.

FIG. 34 shows an assembly diagram of a housing of the interface of a test station embodiment of the inventive technology.

FIG. 35 shows an assembly diagram of a housing of the interface of a test station embodiment of the inventive technology.

FIG. 38 shows an assembly diagram of a base of a test station embodiment of the inventive technology.

FIGS. 39A and B each show an assembly diagram of a base of a test station embodiment of the inventive technology.

FIGS. 40A, B and C show photographs of a circuit board that may find application in a test station embodiment of the inventive technology. FIG. D shows a schematic of the board, with data acquisition card.

FIGS. 41A and B show photographs of a circuit board that may find application in a test station embodiment of the inventive technology. FIG. C shows a schematic of the board, with central processing unit.

FIG. 42 shows an assembly drawing of structural components of a test station embodiment of the inventive technology.

FIG. 45 shows an assembly drawing (A is rear perspective view; B is front perspective view; C is a side view) of an interface plate of a test station embodiment of the inventive technology.

FIG. 50A-50C are the enlarged portions of FIG. 49.

FIG. 51 shows how FIGS. 52A-52F relate to one another in an electrical schematic of electrical aspects of a test station embodiment of the inventive technology.

FIG. 52A-52F are the enlarged portions of FIG. 51.

MODE(S) FOR CARRYING OUT THE INVENTION

Figure 1:
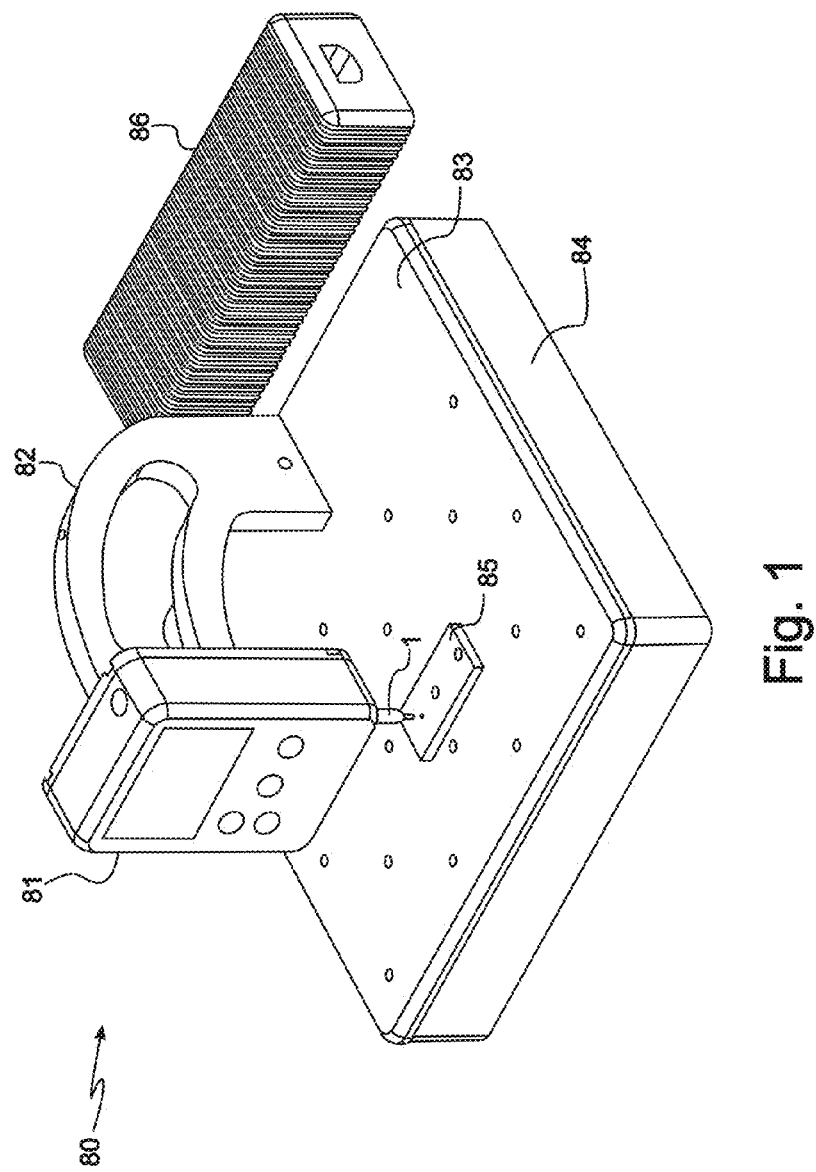
FIG. 1 shows a perspective view of a test station embodiment of the inventive apparatus.

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

A particular aspect of the inventive technology may be generally described as a method for determining test object deformation response that comprises the steps of moving a deformation force deliverer 1 (e.g., an extended shaft of, e.g., a linear actuator 15) to deliver deformation force 24 to a test object 3; adjusting a deformation force deliverer affecting input so as to meet at least one constraint while performing (e.g., simultaneously, or in rapid alternating fashion perhaps) the step of moving the deformation force deliverer 1; deforming the test object 3 with the deformation force; and determining test object response to the deformation force. Test object deformation response may include, perhaps most significantly, deformation force vs. deformation position (travel or displacement) and deformation speed vs. deformation position (where deformation position may simply be an indication of the extent of deformation, or travel, or displacement during deformation, such as 0.63 mm, of a point on the test object).

Other parameters that may be generated in characterization of response include but are not limited to: trip force, return force, minimum force, standing free height, displacement (travel), tactile ratio, contact bounce (e.g., a duration of instability of a switch state after actuation), tactile slope, electrical resistance, tease force, tease travel, release, tactile recovery slope, resistance threshold, testing resistance, bounce time, force required, maximum resistance, number of cycles, impact speed, and displacement velocity. Generally, particularly when the test object is a force activated switch dome, mechanical, electrical and reliability response, such as force vs. displacement, electrical functionality, and life cycle response (e.g., how repeated actuation cycles affect both electrical and mechanical response), are tested. Certain inventive apparatus and methods able to test force activated switch domes may be able to capture response in numerical and/or graphical form as described by ASTM switch testing standards F1570-01; F1597-02; F1682-02; F1997-99. Of course, some of the afore-mentioned parameters (e.g., electrical resistance), may be relevant only when certain test objects, such as force activated dome switches, are tested.

As there are a wide variety of applications of the inventive technology, there are a wide variety of test objects. Broadly, they include any objects whose response to a deformation force is of interest (where deformation force is any force that causes a deformation, regardless of how small, whether elastic and/or plastic). Such response may be characterized as elastic response, hardness response (e.g., when does the material initiate elastic and/or plastic deformation?), and/or cyclical response (e.g., when does the material fail under repeated loading?; how is the deformation force vs. deformation position curve different after 10,000 cycles?), as but a few examples. Of course, a cycle includes a single deformation and release to undeformed state (e.g., a depression of a switch dome with a finger to close a circuit, and a release of such deformation force so the dome returns to its undeformed configuration). Test objects more specifically include, but are by no means limited to: force activated switch domes, force activated switch components (e.g., tactile switches with shapes other than dome), buttons (e.g., as part of a switch, and which include force activated domes), elastomeric materials, mattresses, fabricated materials, fruits and vegetables (for, perhaps, freshness characterization), metals, composite materials, springs, items/devices used or deformed in any fashion repeatedly (e.g., car door handles) and gems. Of course, the inventive technology may be found in automated fashion as part of product quality control, perhaps in an assembly line, as but one of many applications.

It should be understood that a deformation is considered to occur even where it might not be observable by the human eye. Indeed, for particular embodiments of the inventive technology to work properly when the deformation is "unobservable", all that is needed is a sensor that can notice such small deformations (perhaps a linear encoder, including a sensitive photo-eye and a magnified linear, marked slide). As particular embodiments may require sensing changes in deformation position that occur when a very hard material is impacted by, e.g., the deformation force deliverer, particularly sensitive equipment may be necessary to determine test object response.

The deformation force deliverer includes the off-drive components (including, e.g., an extended linear actuator shaft and any tip 5 on such shaft that may directly apply the force to a test object) that move to deliver a deformation force to a test object. It is of note that where a claim limits deformation force deliverer motion or behavior in a certain manner, as long as at least one part of a deformation force deliverer moves or behaves in such manner, such claim limitation is said to be met. As such, where a claim limits deformation force deliverer speed and/or acceleration in some manner (e.g., such is/are identical to that observed by the deformation force deliverer drive), and a rubber tip of the force deliverer exhibits, during deformation of the test object, a different speed and/or acceleration than the rest of the force deliverer because the tip itself deforms more than the rest of the deliverer during test object deformation, such phenomenon (i.e., such differential speed among components of the force deliverer) will not preclude coverage of such "differently-tipped" type design. Such rubber tip may find use in certain types of cyclical failure testing of force activated electrical switch domes. They typically are not used when determining a simple force vs. displacement (or travel) curve because of the inertial and accelerative effects, and resultant error, that may be introduced.

The step of adjusting a deformation force deliverer affecting input so as to meet at least one constraint may comprise the step of adjusting a deformation force deliverer affecting input so as to meet at least one deformation force deliverer motion constraint, such as a constant speed constraint, a constant acceleration constraint (which may be a better replicant of a finger applied force), and/or deformation force deliverer position extrema constraints (which may correspond with an undeformed test object configuration and a maximally deformed test object configuration). It should be noted that instead of using two extrema, other motion range control schemes can be used (e.g., stop at 110% of deformation force). As can be readily understood, a deformation force deliverer affecting input is that input that, when changed, causes a change in the deformation force deliverer (e.g., the motion thereof, or the force delivered thereby).

Often, when the constraint is a deformation force deliverer motion constraint, the step of determining test object response comprises the step of determining deformation force as it relates to deformation position. When the constraint is a deformation force deliverer motion constraint, the step of adjusting a deformation force deliverer affecting input may comprise the step of using a servo-controller 11 and a linear encoder 12 (which may or may not be part of a linear actuator), and/or the step of determining test object response may comprise the step of reading recorded calibration data. The servo-controller (one manufactured by SMAC™, e.g.) may, perhaps through use of a proportional integral derivative controller, use measured data (perhaps deformation speed, acceleration and/or deformation position that may be measured with a linear encoder) to determine whether and by how much input (e.g., current, or perhaps pneumatic pressure) should be adjusted to meet a constraint. It can then adjust input as necessary. It is of note that, particularly where that part that contacts the test object and applies the deformation force (a deformation force deliverer tip) is of the same material as the deformation force deliverer (e.g., they have the same elastic response), deformation position may be directly associated with, and even identical with, force deliverer position (e.g., both may have traveled the same amount in one test cycle). As mentioned, a rubber tip may be used (e.g., in certain cyclical testing), perhaps to better replicate the force applied by a human finger.

Figure 25:
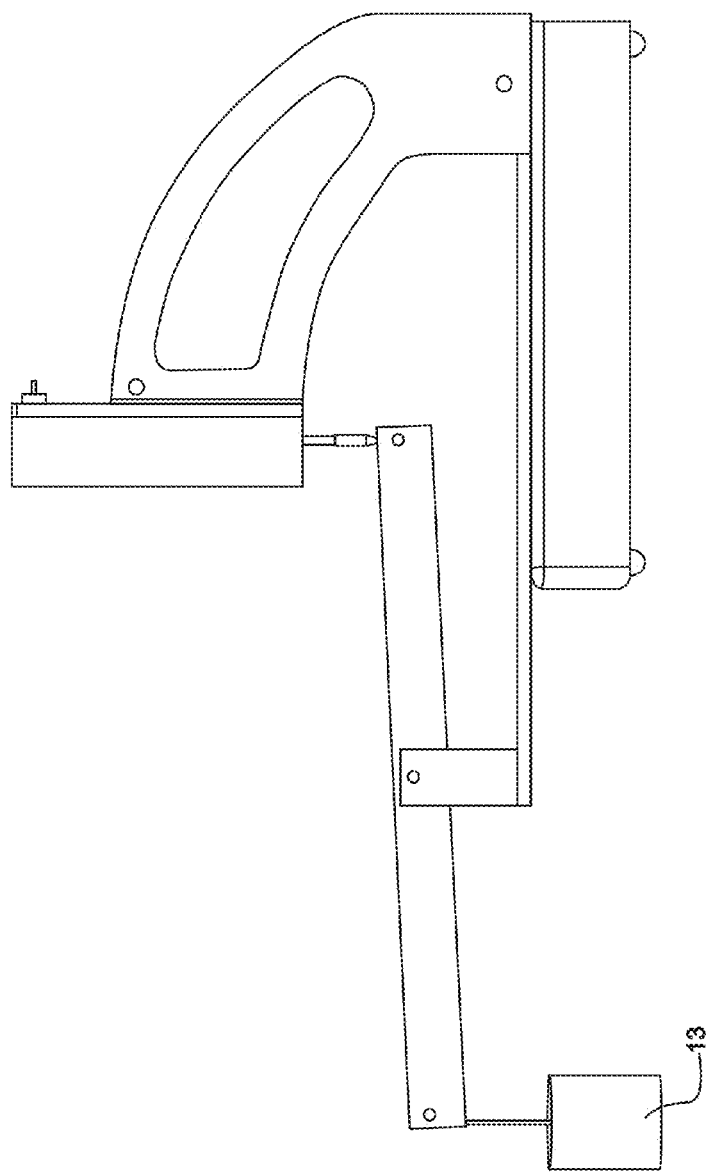
FIG. 25 shows a diagram of a test station embodiment as configured during calibration.
Figure 26A:
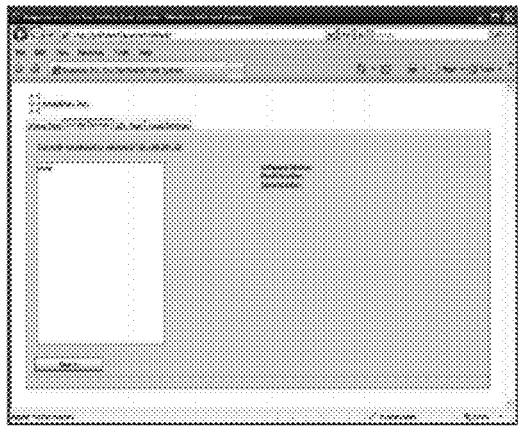
FIG. 26A-E show possible screens as they may appear on a screen (whether on the interface or on a stand-alone computer such as a laptop).
Figure 26B:
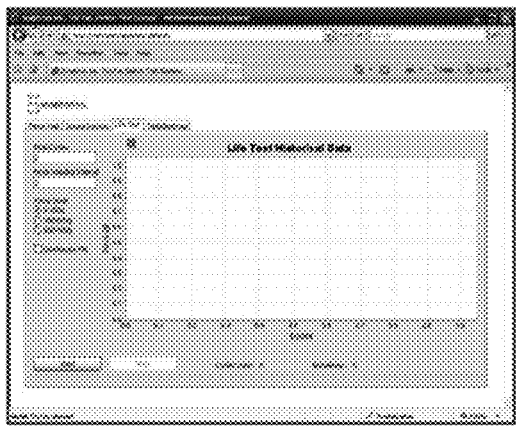
Figure 26C:
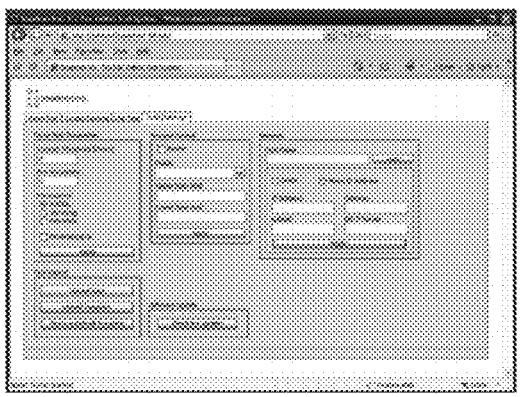
Figure 26D:
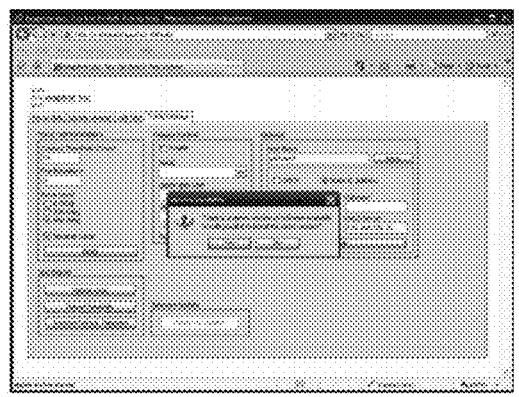
Figure 26E:
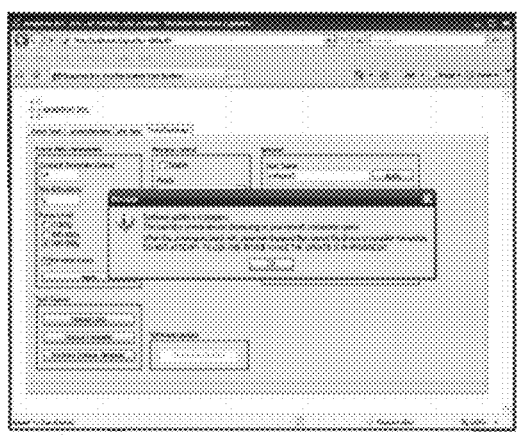
Figure 26F:
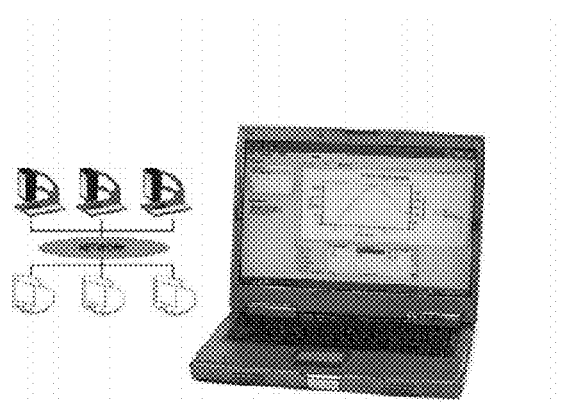
FIG. 26F shows a laptop with a screen showing a force vs. displacement curve, in addition to showing how a plurality of test stations and computers may be linked through a network.
Figure 28:
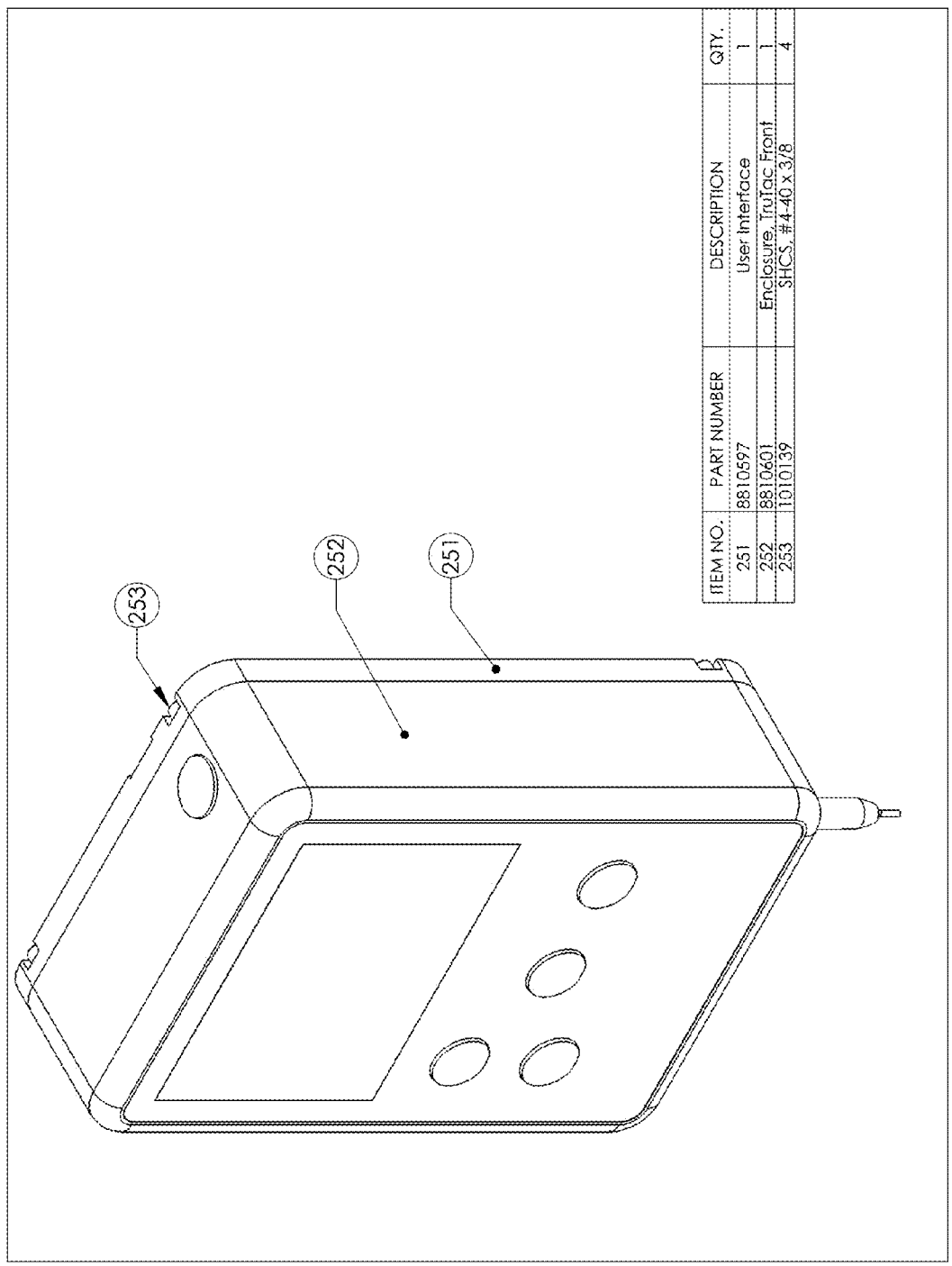
FIG. 28 shows a diagram of an interface of a test station embodiment of the inventive technology.
Figures 36A, 36B:
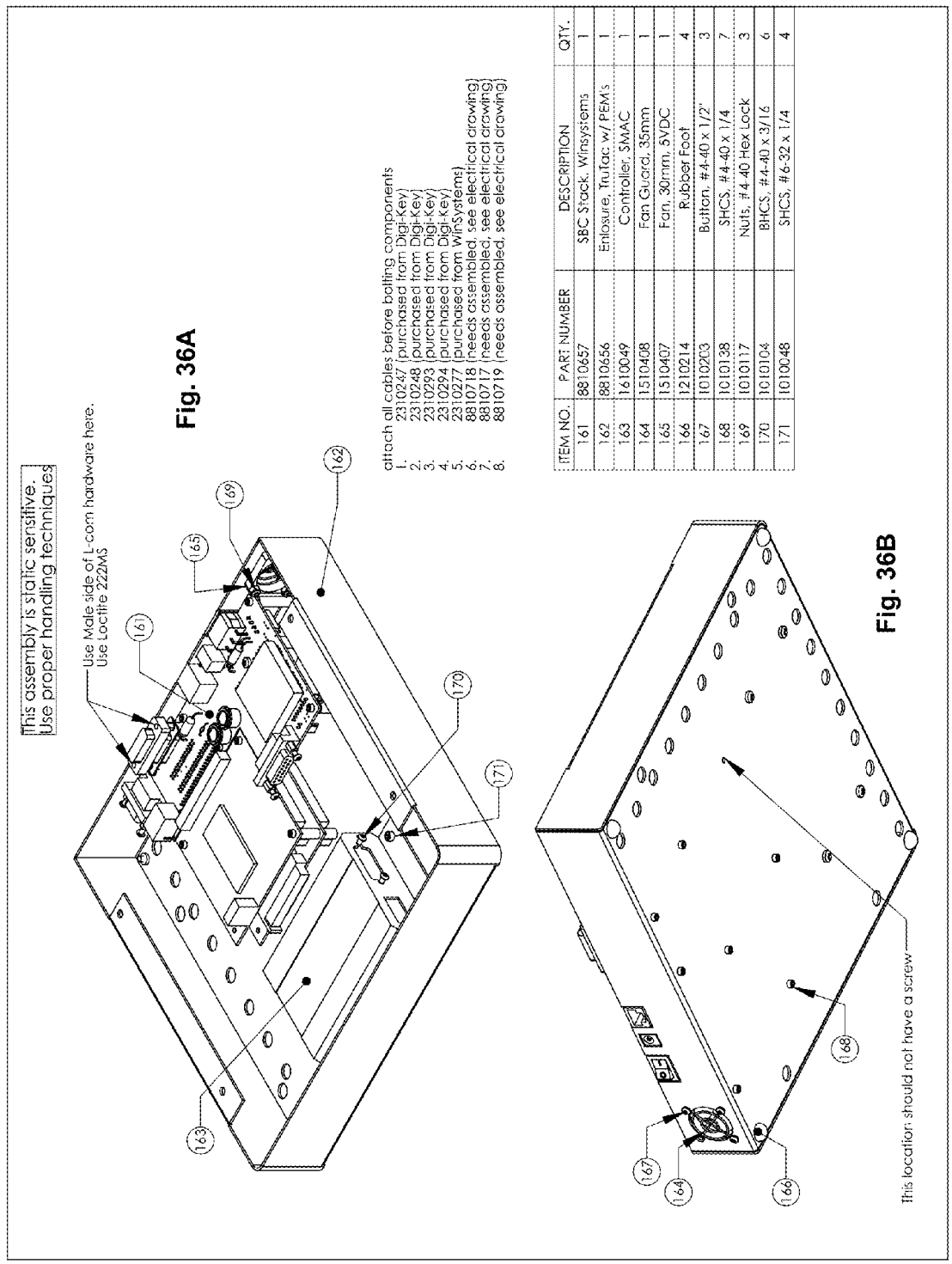
FIG. 36 shows an assembly diagram of a base of a test station embodiment of the inventive technology.
Figure 37B:
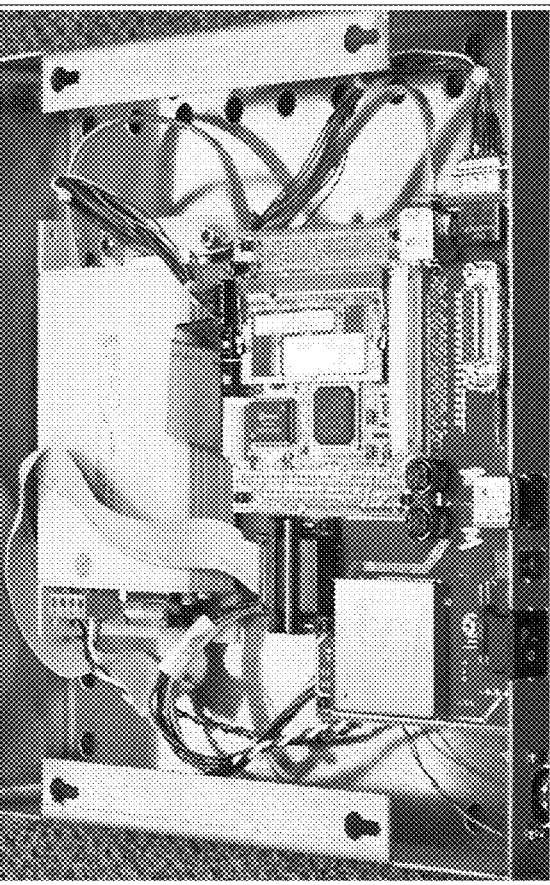
FIGS. 37B and C show photos thereof.
Figure 37A:
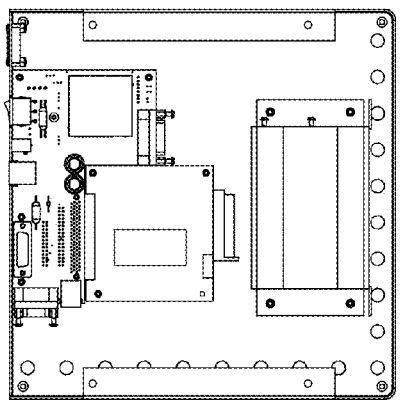
FIG. 37A shows an assembly diagram of a base of a test station embodiment of the inventive technology.
Figure 37C:
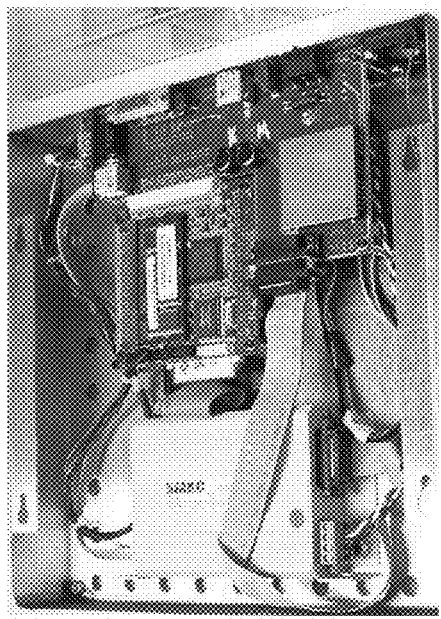
Figure 43:
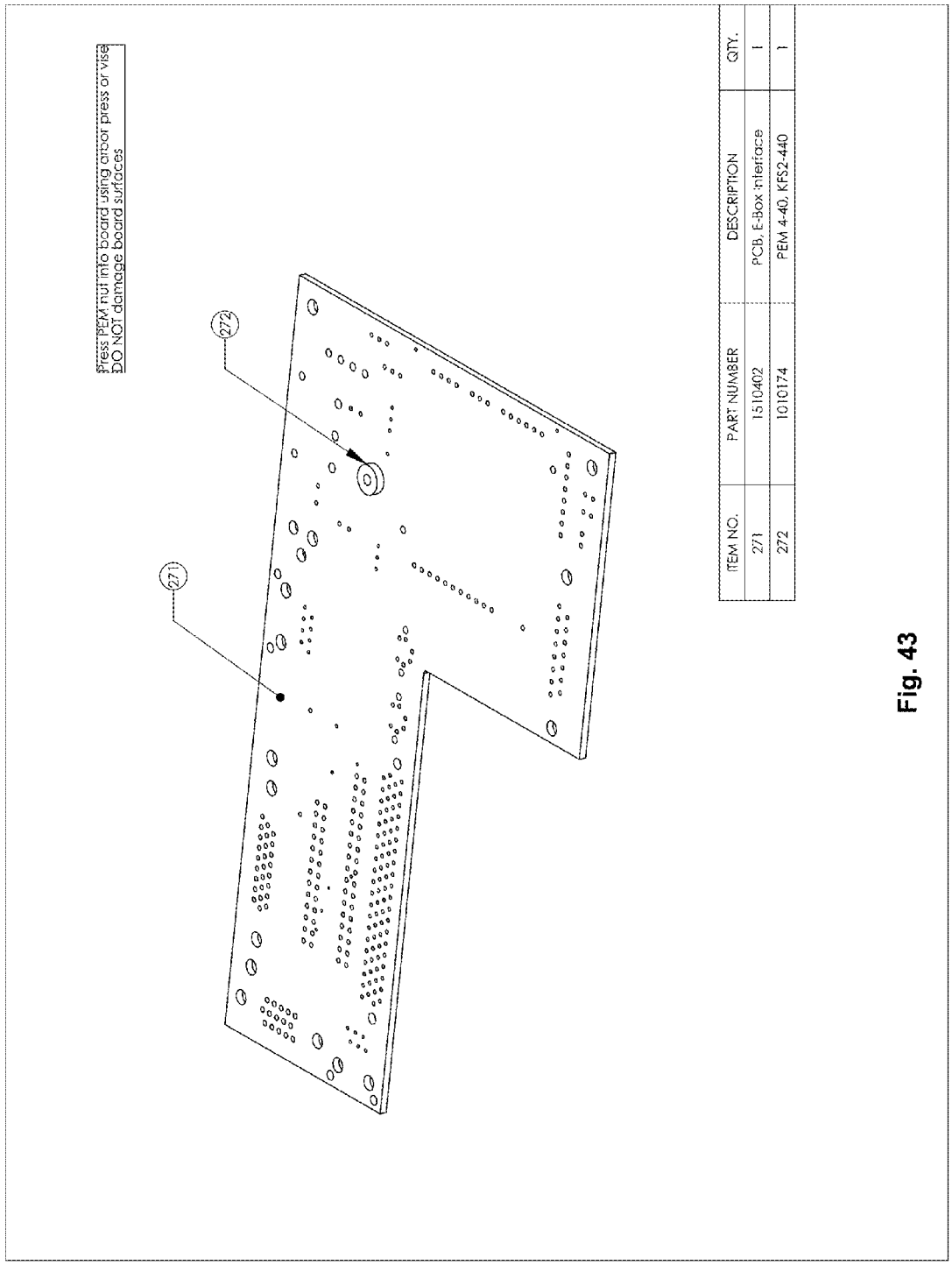
FIG. 43 shows an assembly drawing of a structural board of a test station embodiment of the inventive technology.
Figure 44B:
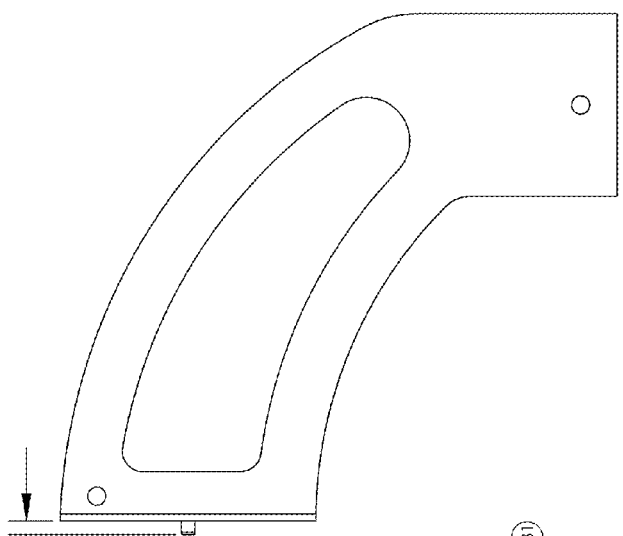
FIG. 44A shows an assembly drawing (A is perspective view; B is side view) of a support arm of a test station embodiment of the inventive technology.
Figure 44A:
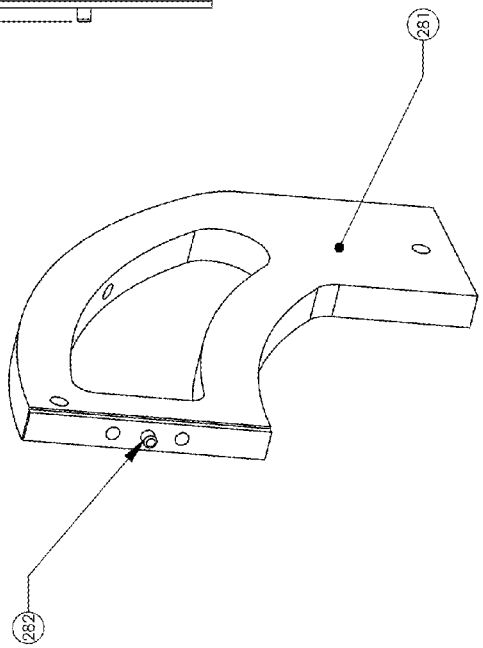
Figure 46:
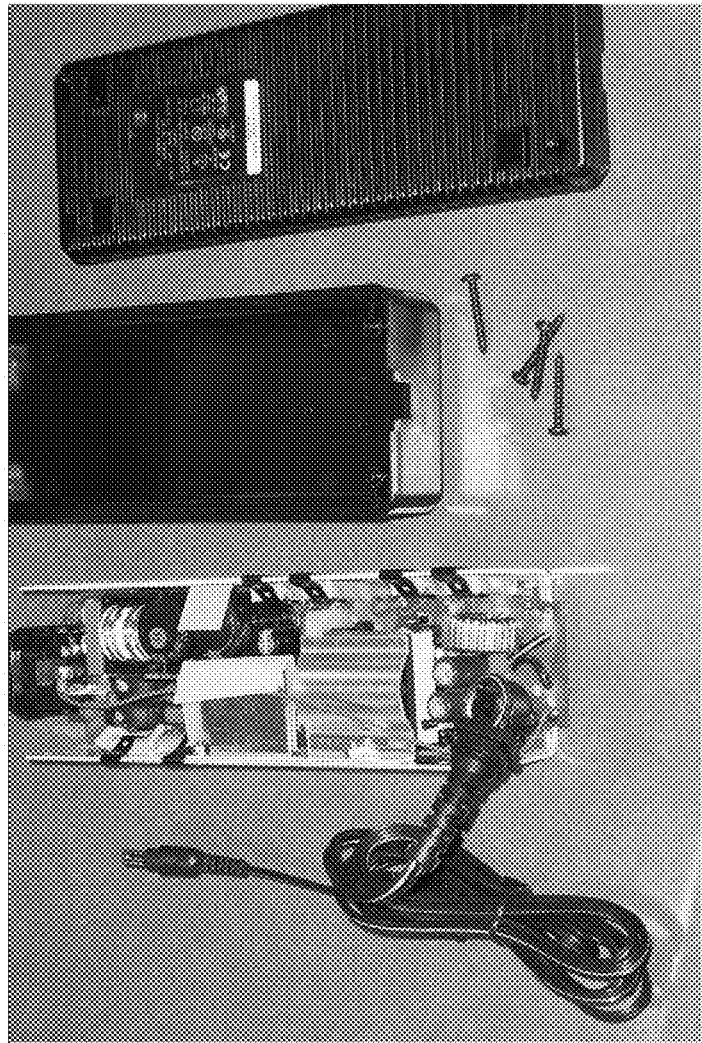
FIG. 46 shows a photograph of components as they may appear before final assembly of a test station embodiment of the inventive technology.
Figure 47:
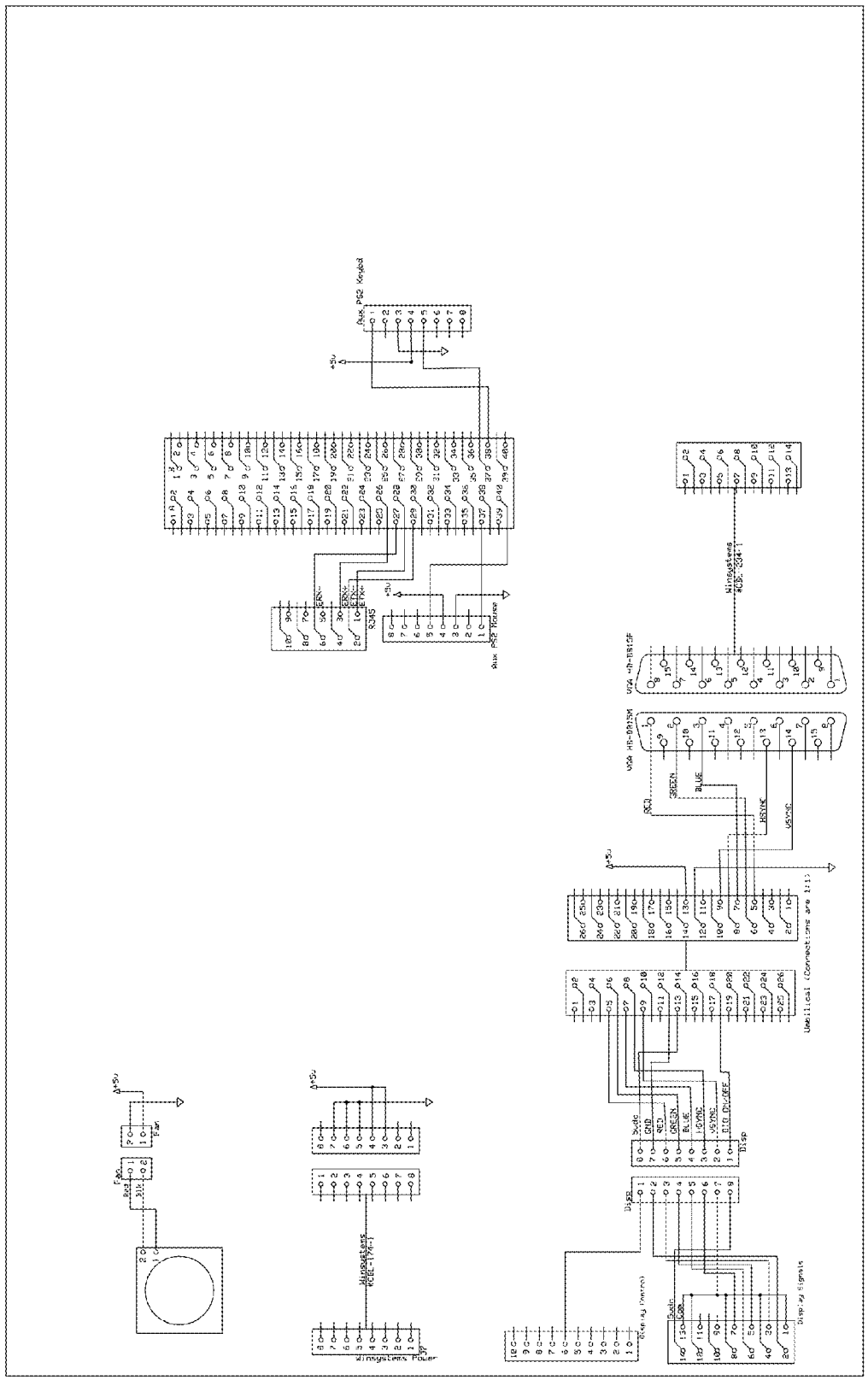
FIG. 47 shows how FIGS. 48A-48G relate to one another in an electrical schematic of electrical aspects of a test station embodiment of the inventive technology.
Figure 48:
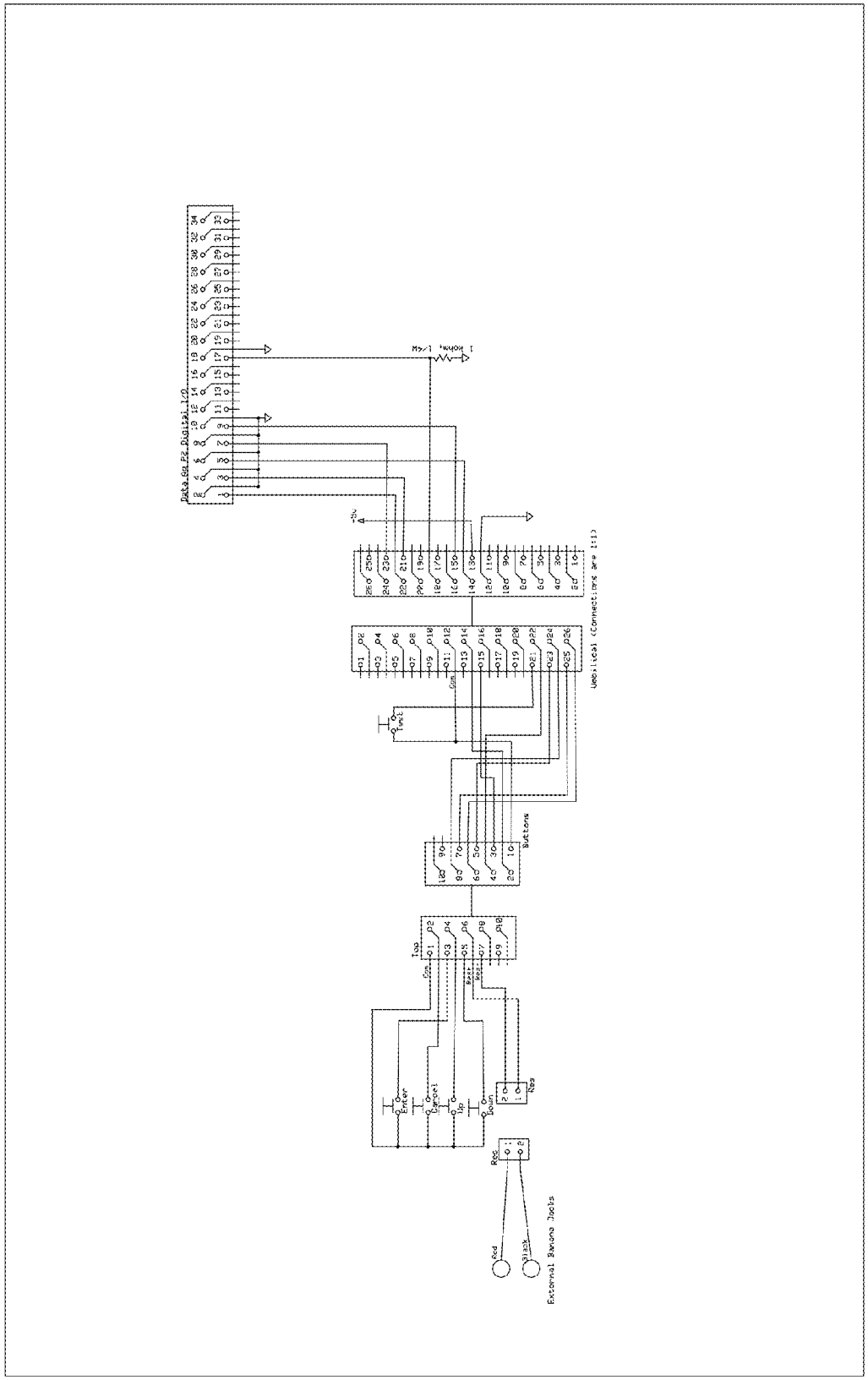
FIG. 48A-48G are the enlarged portions of FIG. 47.
Figure 49:
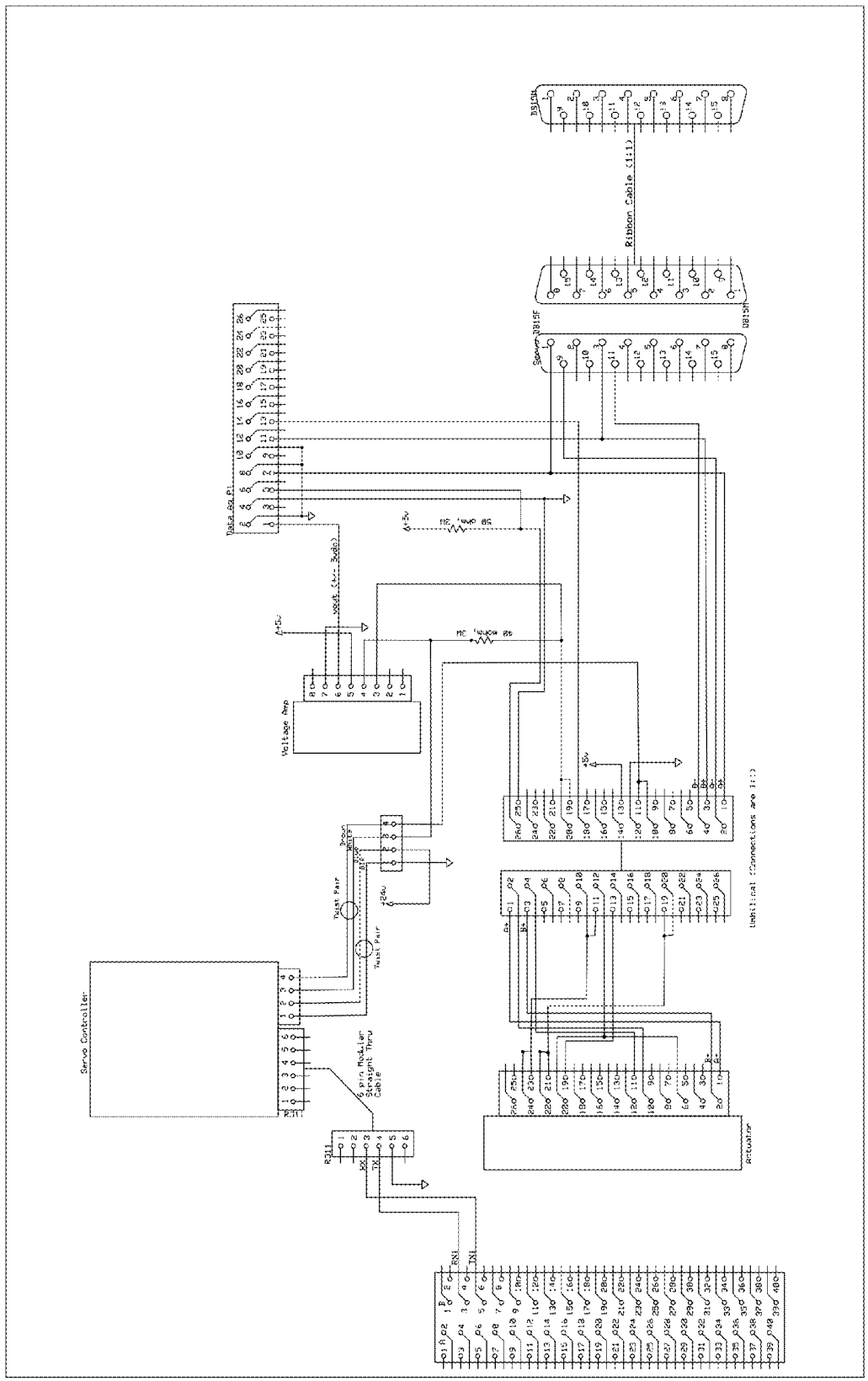
FIG. 49 shows how FIGS. 50A-50C relate to one another in an electrical schematic of electrical aspects of a test station embodiment of the inventive technology.

Calibration data, which may relate force to deformation force deliverer position, e.g., the vertical position or the deformation force deliverer (which may be directly related, perhaps identical, to deformation position or displacement of the test object) to deformation force and input current, may be generated in the following manner: a first mass 13 may be configured (e.g., suspended, perhaps in levered fashion) so as to deliver a known force to the deformation force deliverer (perhaps in a direction opposite that of the deformation force delivered thereby). Current to a device that drives the deformation force deliverer (e.g., current to a linear actuator) may be then controllably increased (e.g., at a constant rate) while position data is recorded for a plurality of current values, up to an appropriately high value (which would be obvious to the calibrating technician and may depend on the displacement range necessitated by an anticipated testing application(s)). Data for such mass may then be recorded. These steps would be repeated for a variety of masses that would sufficiently cover the range of expected forces for the anticipated testing application(s). An example of a few calibration data points could be: for 100 grams, at 0.23 mm of displacement, a current of 3.01 amps; for 100 g., at 0.27 mm of displacement, a current of 3.42 amps; for 200 g., at 0.23 mm of displacement, a current of 5.28 amps; for 200 g., at 0.27 mm displacement, a current of 5.72 amps. The data may be presented on a graph with a horizontal ("x") axis of deformation force deliverer position, a vertical ("y") axis of applied current (or corresponding voltage), and a series of perhaps curves (e.g., lines), each associated with a specific mass (see, e.g., FIG. 25). If the goal is to determine deformation force, such curves could be used (perhaps the computer would use the actual data that such curves represent) by using a computer component to read (a term that includes interpolate) which force (or mass) is associated with known deformation position (which may be measured by a linear actuator) and known current data. If the goal is to determine current to be applied to generate a constant force, such data could be also be useful, in ways that would be apparent to one of ordinary skill in the art. Determining either force (e.g., in a deformation force deliverer motion constraint application), or, on the other hand, current (e.g., current needed to meet a force constraint, such as to maintain a specific, constant force), will often require interpolation between measured calibration data (typically between two masses). It may be that, instead of the "brute force", mass-by-mass calibration, a mathematical relationship usable to generate force from measured position and current data may be generated.

Of course, if a constant deformation speed (displacement speed) is a constraint, current may be increased or decreased by the servo-controller 11 when readings from the linear encoder 12 indicate that speed is falling slightly below, or rising slightly above, the constant deformation speed constraint. Recorded calibration data, which may relate force to position and current, may then be used to generate force vs. deformation position values (current and position are known or measured, and, from such measurements, deformation force can be estimated at each deformation position using calibration data). When a constraint relates to motion of the displacement of the test object (e.g., speed or acceleration of deformation), and particularly when the test object is a force activated switch dome (including but not necessarily limited to what are known as bi-stable domes), it is of note that the test object may be said to exhibit a constant speed even when movements at the very beginning of the deformation and after the trip force is met are not constant (but perhaps all other movements are). Of course, in a typical force delivery (e.g., half of a cycle), the force deliverer must be first accelerated from zero speed (so, at such initial times, speed is not and cannot be constant), and, again, particularly with regard to testing of certain force activated switch domes (with a deformation force applied in the positive direction of deformation), speed cannot be controlled when a threshold-triggered deformation (observed at the trip of a switch dome) advances a deformed portion of the dome in such positive direction at a speed that is greater than that of the part of the force deliverer (e.g., a force deliverer tip) that applies the deformation force). When such trip related concern does not apply, there nonetheless exist non-constant speeds at the beginning and end of a cycle (of course, speed must increase and decrease from and to zero at such travel portions); where motion is constant after such acceleration and terminal deceleration, the speed is said to be constant (or meet some other intended (and perhaps user-input) constraint.

A constant deformation speed constraint may be preferred over a constant acceleration or other constraints because a constant speed constraint avoids error that may be introduced by accelerative or inertial effects that may be associated with such other constraints. It is also of note that deformation force deliverer position extrema constraints may be used to demarcate the endpoints of the travel of the test object during deformation.

In preferred embodiments, the step of adjusting a deformation force deliverer affecting input may comprise the step of adjusting an electrical input, which itself may comprise the step of adjusting a current; as is well known, one way in which current may be adjusted is by adjusting a voltage. In such embodiments, and, indeed, in others, the step of adjusting a deformation force deliverer affecting input may comprise the step of using a linear encoder 12 and a servo controller 11 (e.g., as in certain deformation motion constraint embodiments) or the step of using recorded calibration data 58 and a servo controller 11 (e.g., as in certain deformation force constraint embodiments). Also, in preferred embodiments, the step of adjusting a deformation force deliverer affecting input is repeated automatically (i.e., the step of adjusting a deformation force deliverer affecting input is automatically adjusting). Of course, such may occur many times per second; the more often the feedback is received and adjustments are made, the more accurate and representative the results.

In particular embodiments, the step of adjusting a deformation force deliverer affecting input so as to meet at least one constraint may comprise the step of adjusting a deformation force deliverer affecting input so as to meet a deformation force constraint (e.g., a constant deformation force). In such embodiments, one particular control scheme may control force deliverer motion with additional deformation force deliverer position extrema constraints. In such embodiments, the step of adjusting the deformation force deliverer affecting input may comprise the step of reading recorded calibration data and using a servo-controller 11. More specifically, the calibration data, which may relate current to force and to position, may be used to determine which current is needed to generate the desired deformation force (e.g., the desired constant force) at a specific position; the servo-controller 11 may then simply adjust current to that amount. In deformation force constraint embodiments, the step of determining test object response may comprise the step of using a linear encoder 12. Simply, the linear encoder 12 may be used to measure speed at individual deformation positions. As such, the step of determining test object response may comprise the step of determining deformation speed as it relates to deformation position.

When the step of determining test object response comprises the step of determining the deformation force, the step of adjusting a deformation force deliverer affecting input so as to meet at least one constraint may comprise the step of using a linear encoder 12 and a servo controller 11 to apply the proper amount of current necessary to move the deformation force deliverer at a constant speed or acceleration. Further, the step of determining deformation force (e.g., deformation force vs. deformation position) may comprise the step of generating adjusted deformation force dependent input values (e.g., adjusted currents), and reading recorded calibration data based on such values (e.g., reading which force is associated with a specific current applied while the test object is deformed at a certain position). Again, when determining test object response comprises the step of determining the deformation force, determining test object response may comprise the step of determining deformation force as it relates to deformation position; force versus test object deformation data (displacement or travel data) may be presented, whether graphically or otherwise.

When the step of determining test object response comprises the step of determining deformation speed, the step of adjusting a deformation force deliverer affecting input so as to meet at least one constraint may comprise the step of using calibration data to determine current necessary to deliver a specific constant force at force deliverer positions. As mentioned, such may involve the use of recorded calibration data and a servo-controller 11. Further, the step of determining deformation speed may comprise the step of using a linear encoder 12 to generate speed vs. deformation position data, and the step of determining deformation speed (again, which may be identical to deformation force deliverer speed) may comprise the step of generating adjusted deformation force dependent input values (e.g., adjusted currents necessary to keep the force at the desired level). Of course, deformation speed versus test object deformation data may be presented, whether graphically or otherwise.

In particular embodiments, the step of moving a deformation force deliverer to deliver deformation force to a test object 3 may comprise the step of delivering current to a linear actuator 15 (such as a linear voice coil actuator, whether it have moving voice coil 16 or moving permanent magnet). Alternatives to a linear actuator include but are not limited to: electrostatic speaker type diaphragm and plate system, and planar magnetic speaker type systems.

Figure 2:
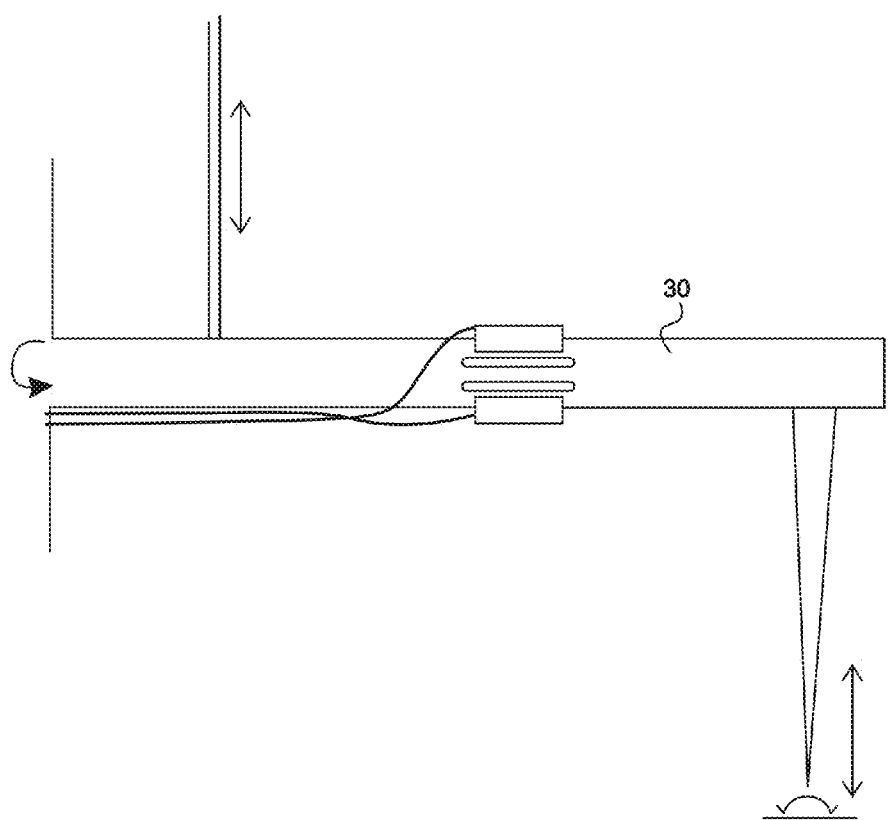
FIG. 2 shows a side view of a prior art switch dome tester.
Figure 3A:
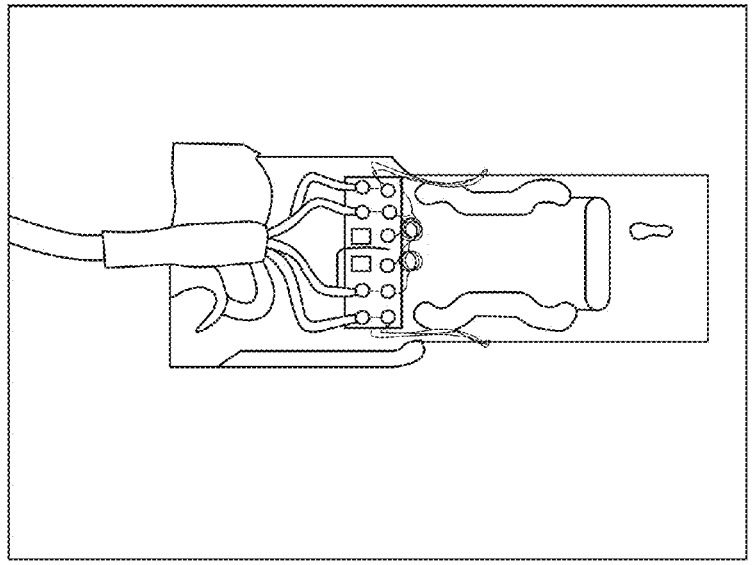
FIGS. 3A and B show a side and top view of a portion of a cantilever of a prior art tester, including strain gages.
Figure 3B:
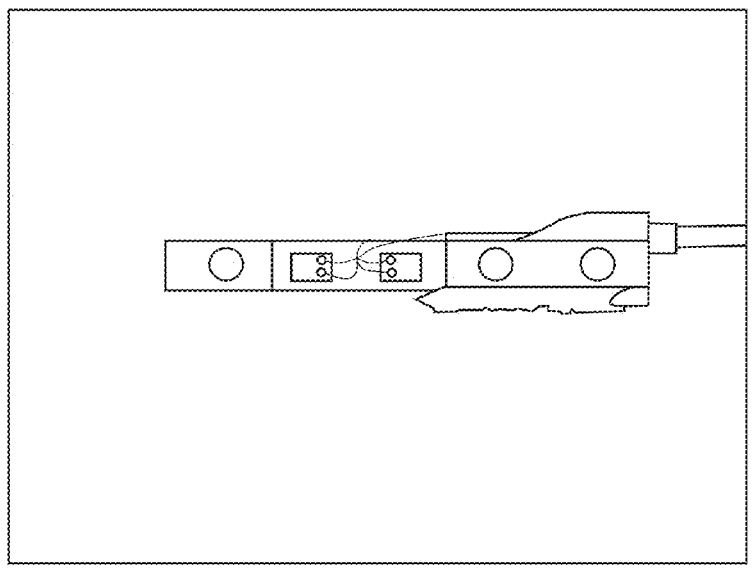
Figure 4:
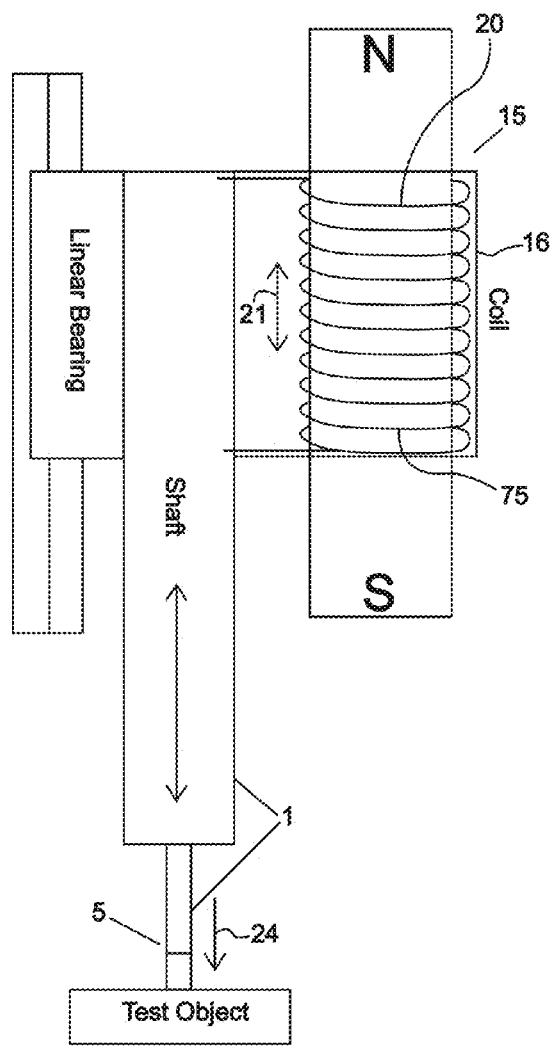
FIG. 4 shows a side view schematic of a voice coil embodiment of the inventive technology.
Figure 5:
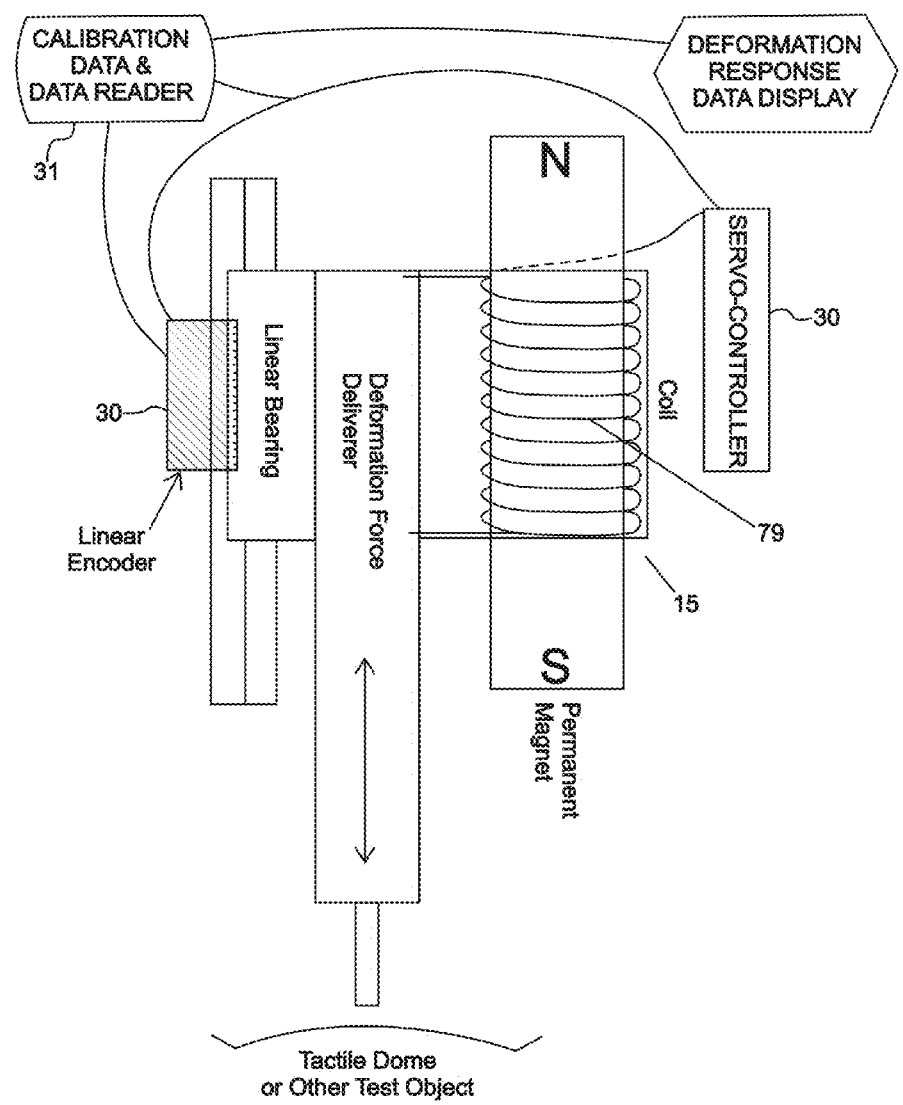
FIG. 5 shows a side view schematic of a voice coil embodiment of the inventive technology.
Figure 6A:
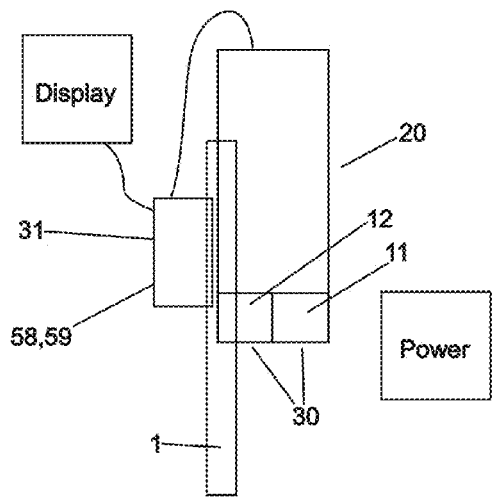
FIGS. 6A and B show side view schematics of embodiments of the inventive technology.
Figure 6B:
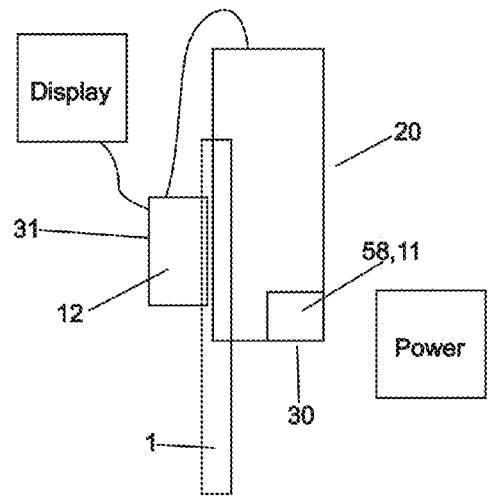
Figure 7:
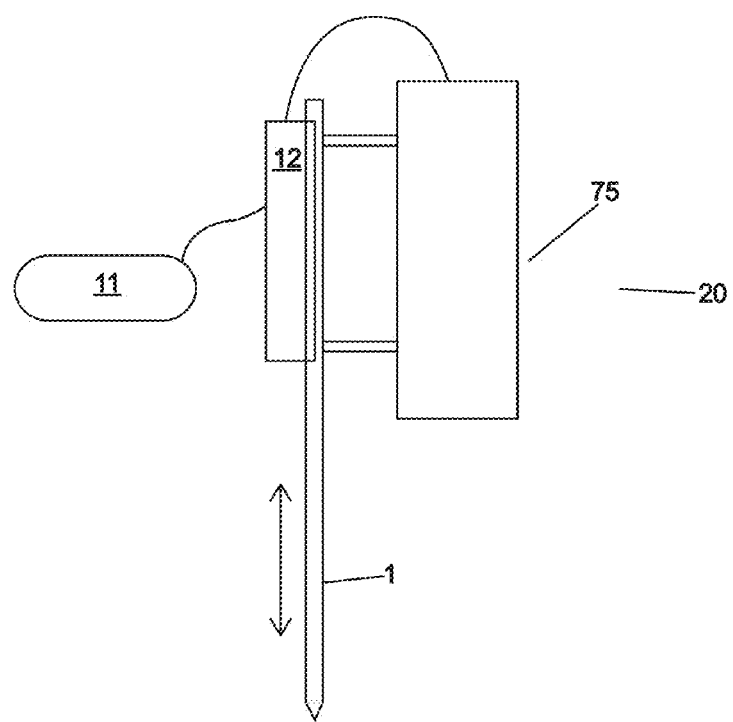
FIG. 7 shows a side view schematic of an embodiment of the inventive technology.
Figure 8:
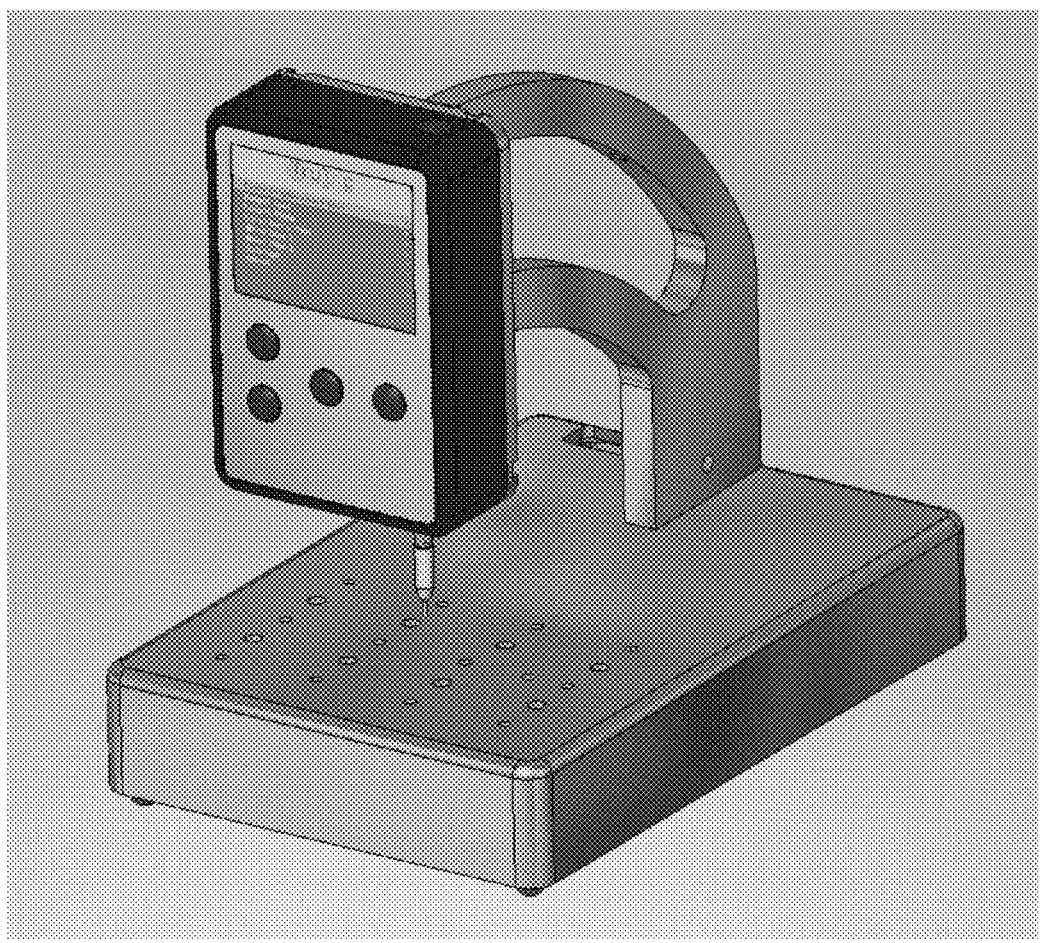
FIG. 8 shows a perspective view of a test station embodiment of the inventive apparatus.
Figure 9:
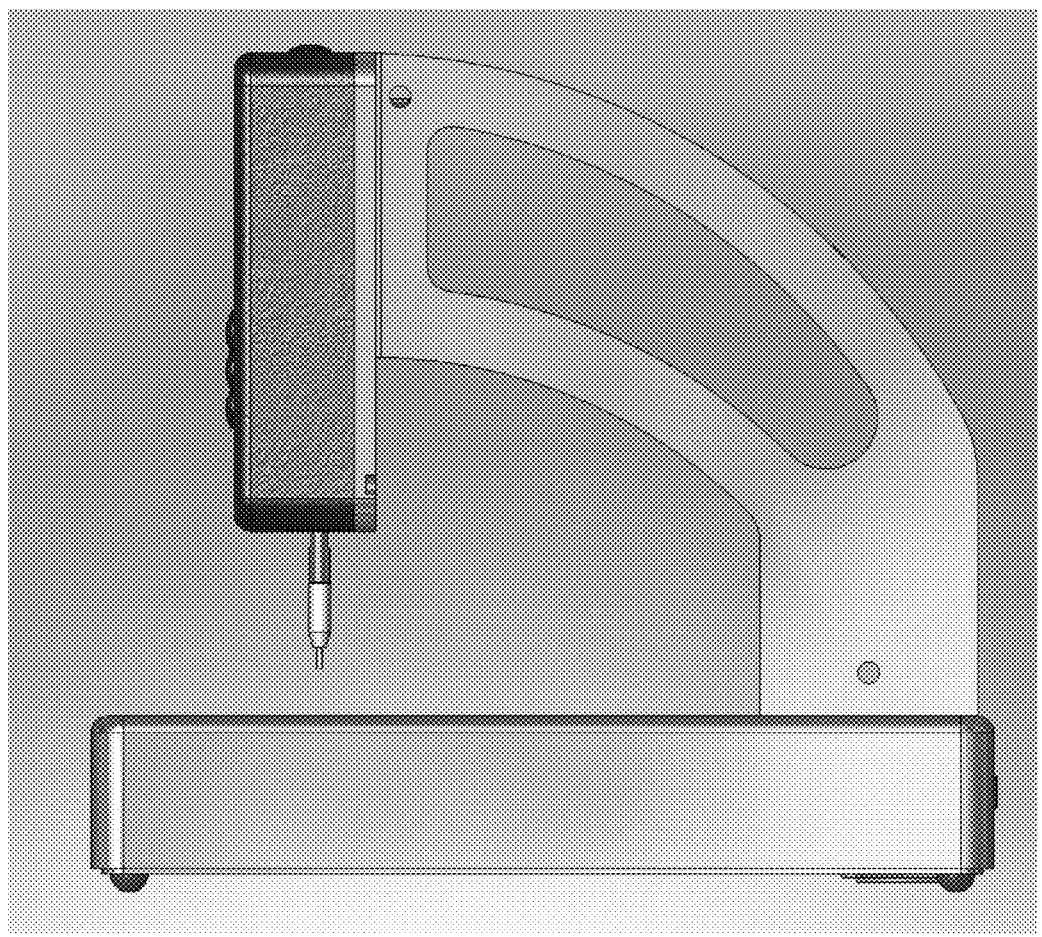
FIG. 9 shows a side view of a test station embodiment of the inventive apparatus.
Figure 10:
FIG. 10 shows a front view of a test station embodiment of the inventive apparatus.
Figure 11:
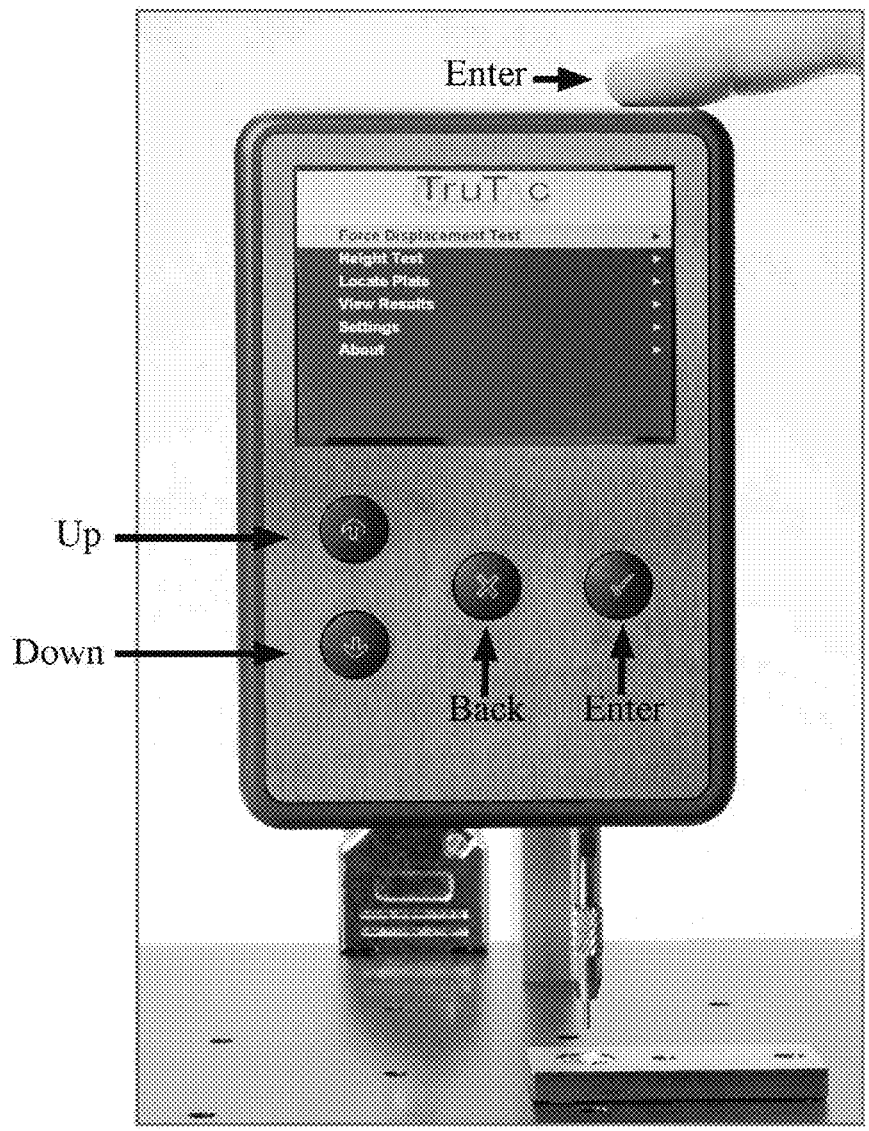
FIG. 11 shows a perspective view of an interface, test object block locator, and deformation force deliverer of a test station embodiment of the inventive apparatus.
Figure 12A:
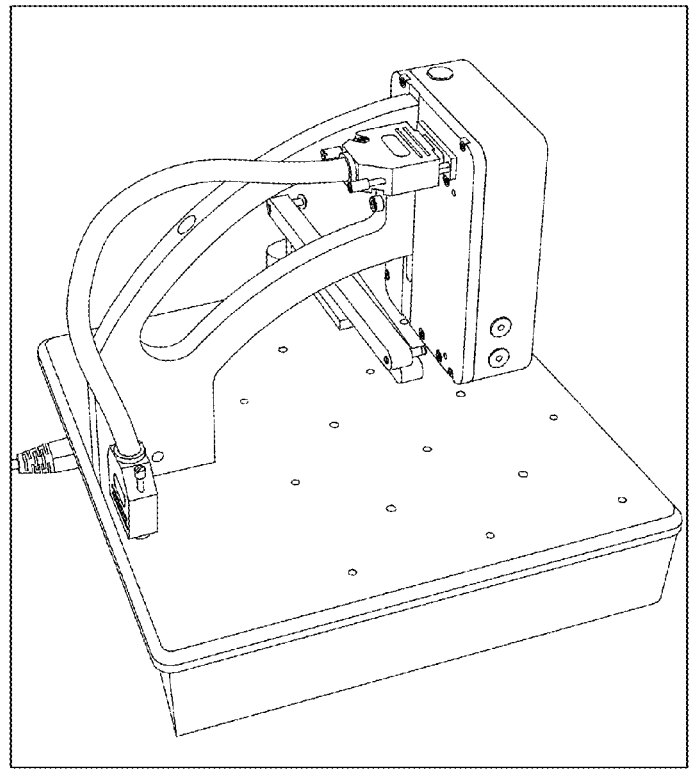
FIGS. 12A and B show a perspective rear and a front view of a test station embodiment of the inventive apparatus.
Figure 12B:
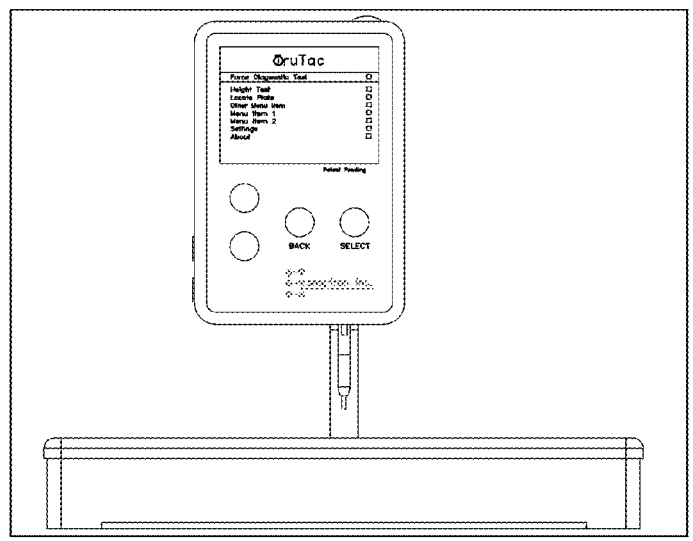
Figure 13A:
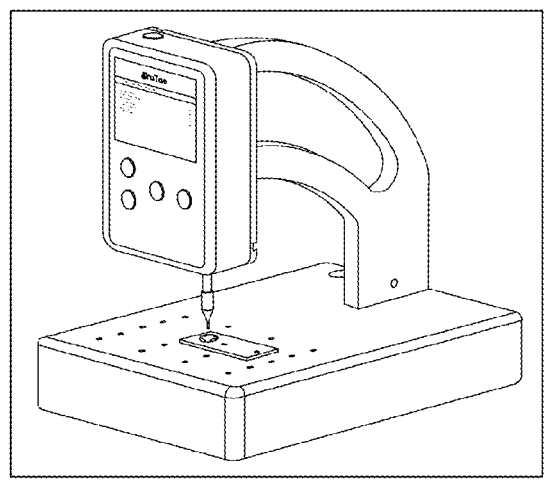
FIGS. 13A and B show a perspective side and perspective front view of a test station embodiment of the inventive technology.
Figure 13B:
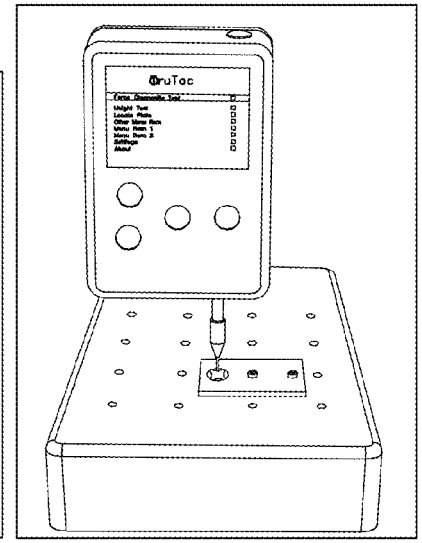
Figure 13C:
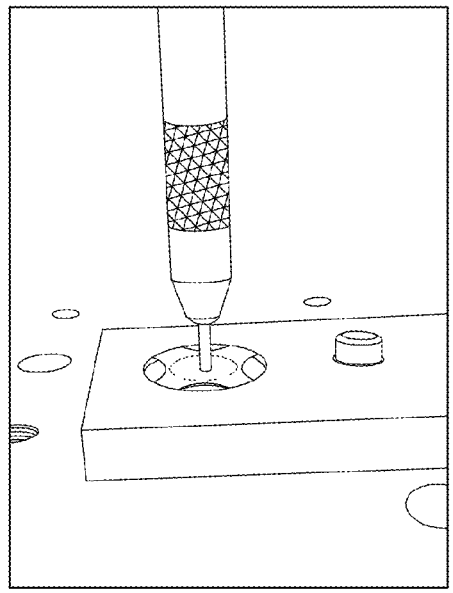
Figure 13D:
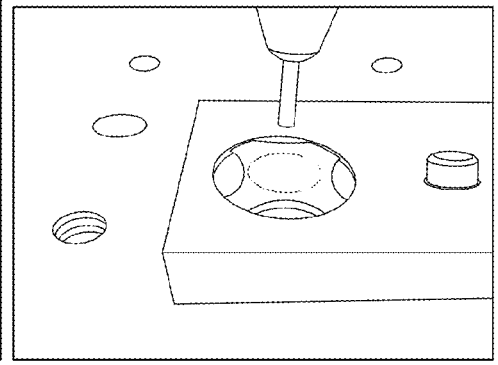
FIG. 13D shows a closeup view of a deformation force deliverer above a test object on a test object block locator.
Figure 14:
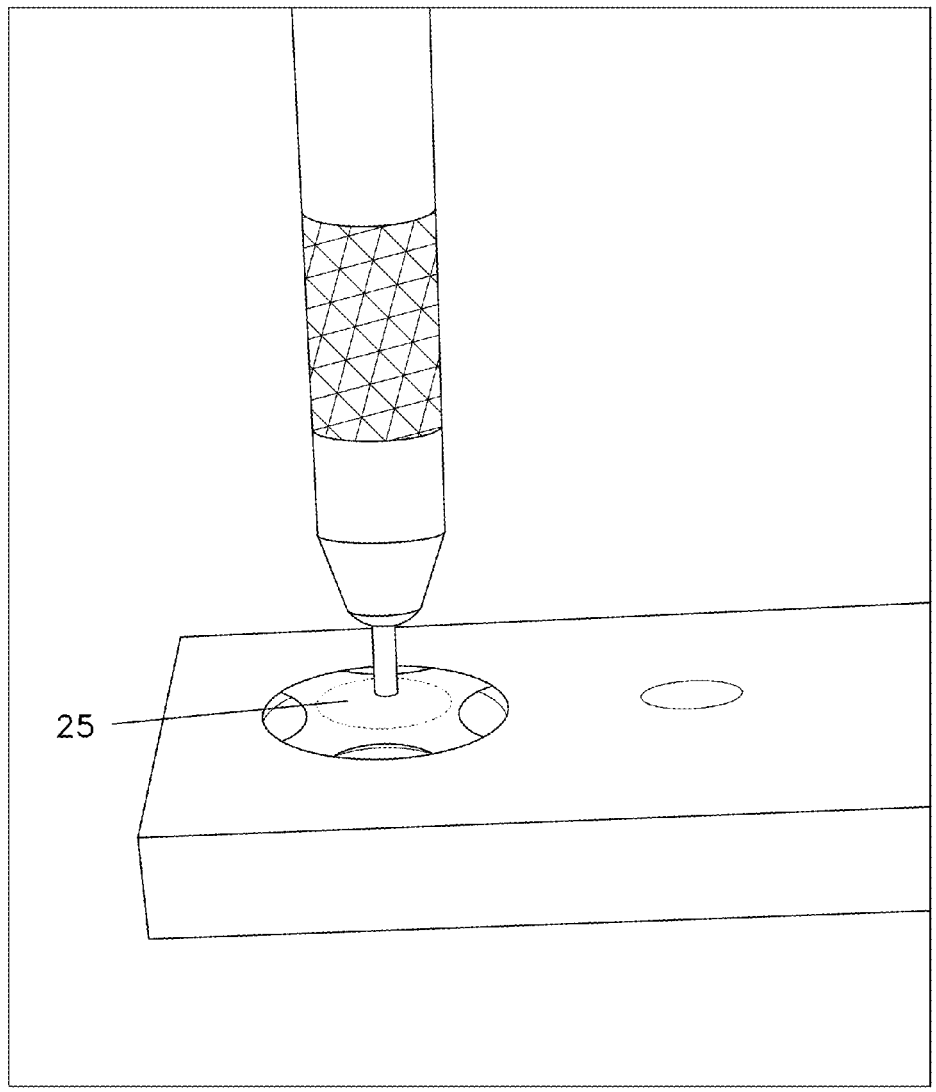
FIG. 14 shows a closeup view of a deformation force deliverer in contact with a test object on a test object block locator.
Figure 16A:
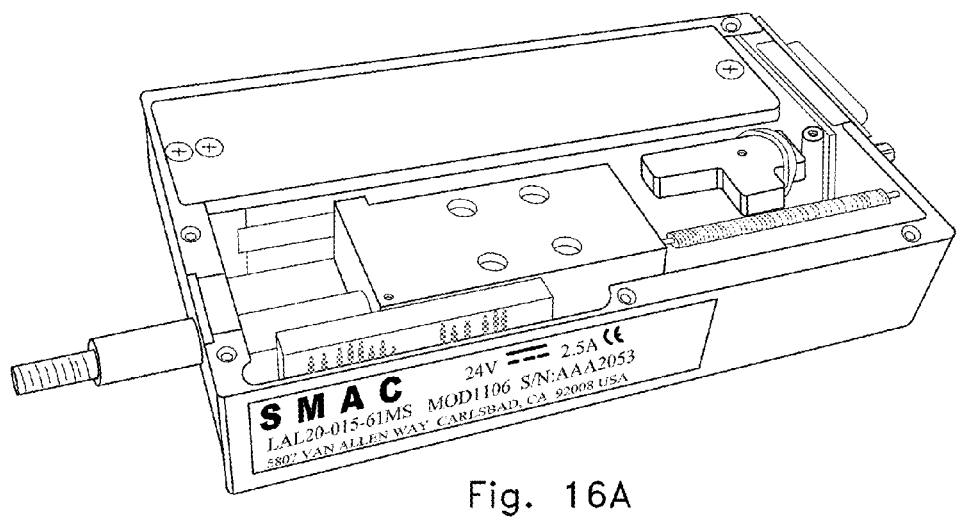
FIGS. 16A and B show a side perspective view and a direct side view, respectively, of a linear actuator that may find application in the inventive technology.
Figure 16B:
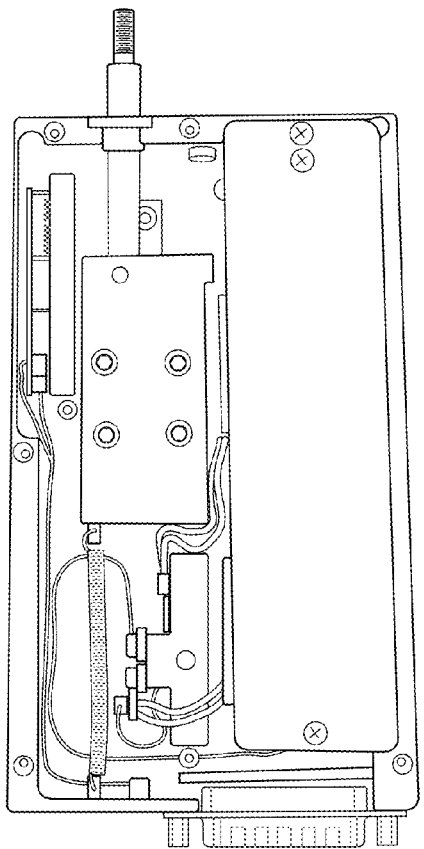
Figure 18:
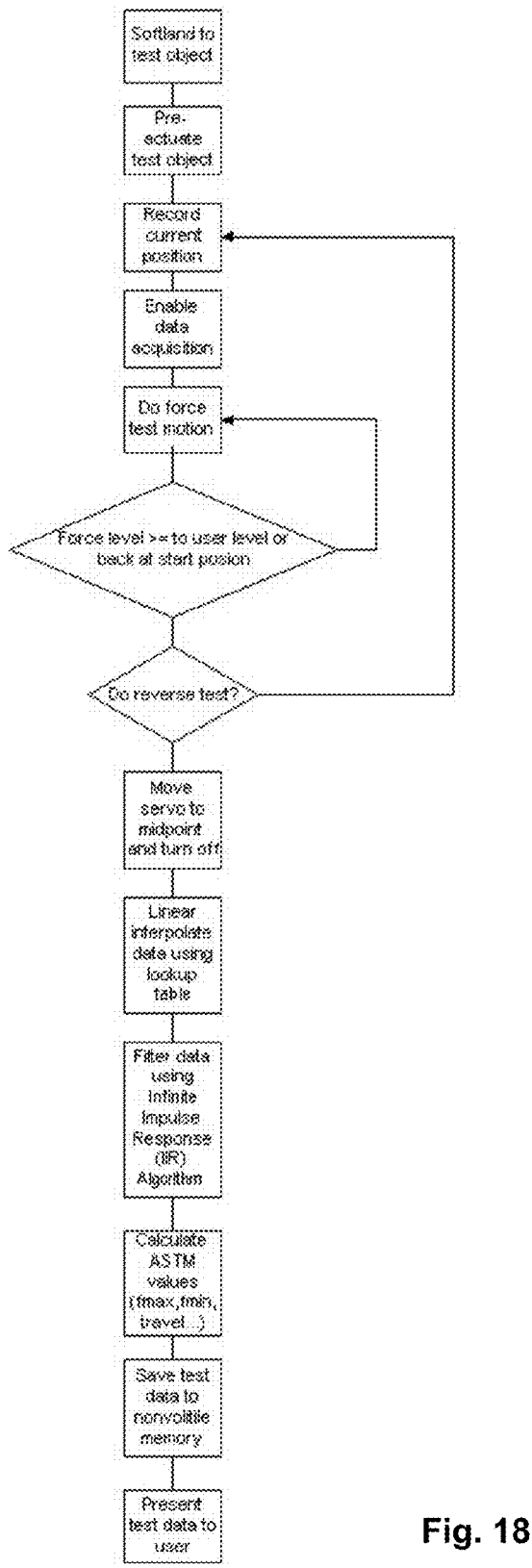
FIG. 18 shows a flow chart that presents primary computational/code steps of software that may find application in the inventive technology.
Figure 19:
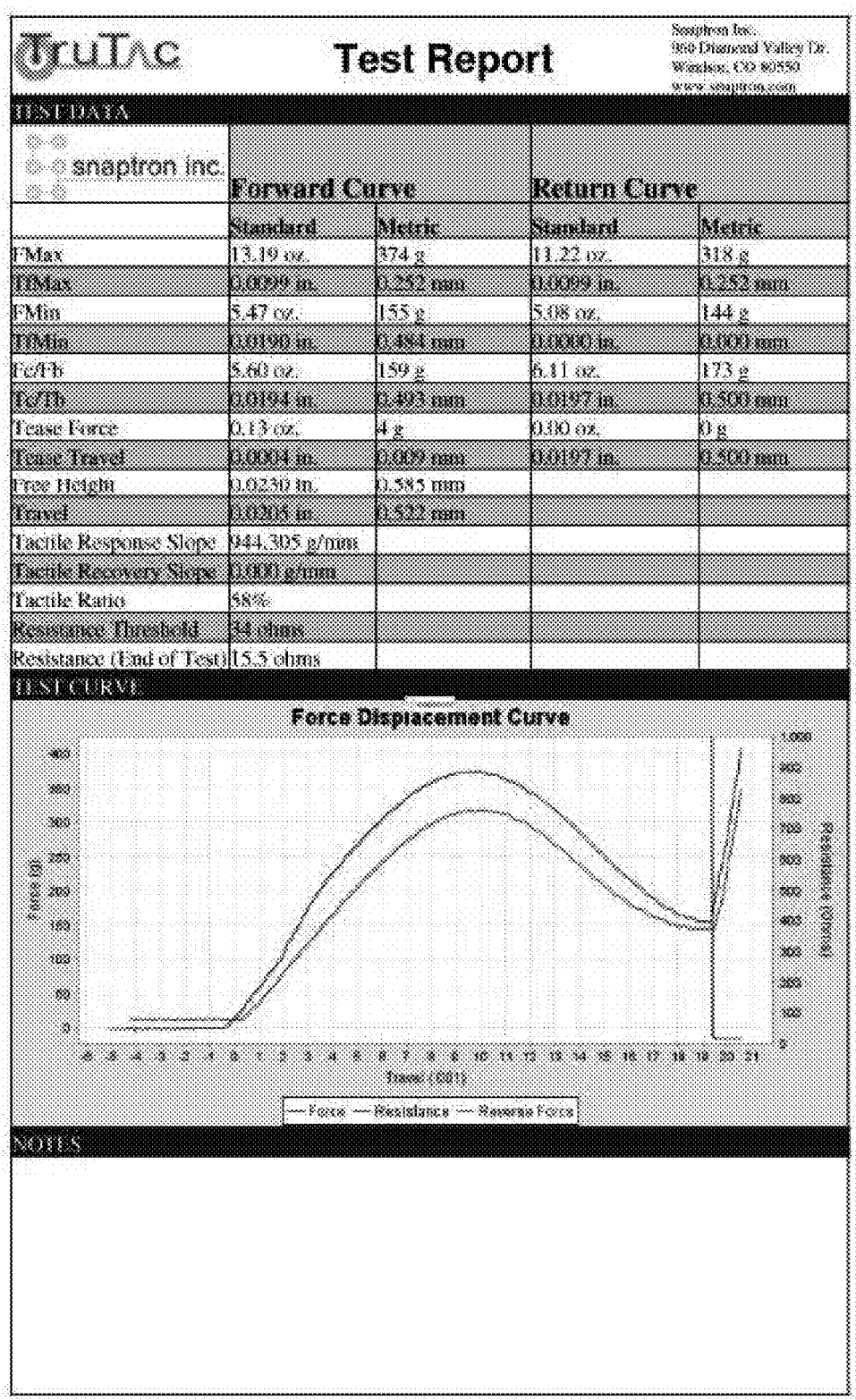
FIG. 19 shows a deformation force vs. deformation position (travel) curve, and associated data, for a specific test object (a force activated switch dome in this case).
Figure 20:
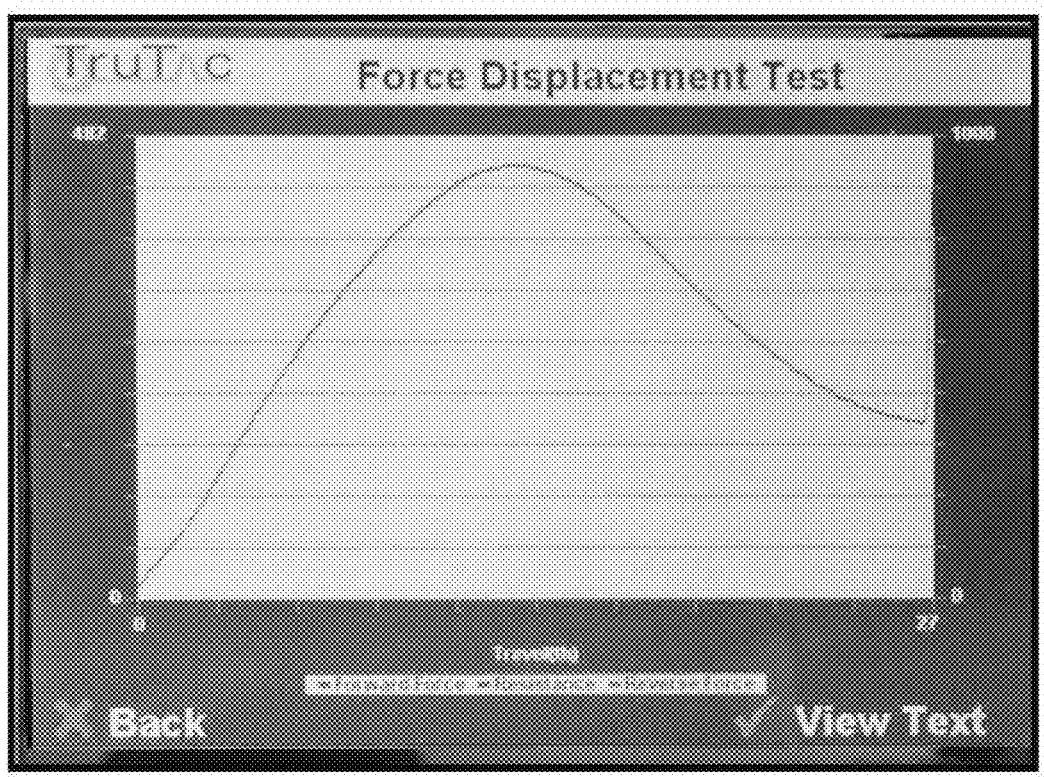
FIG. 20 shows a deformation force vs. deformation position (travel) curve for a specific test object (a force activated switch dome in this case).
Figure 21:
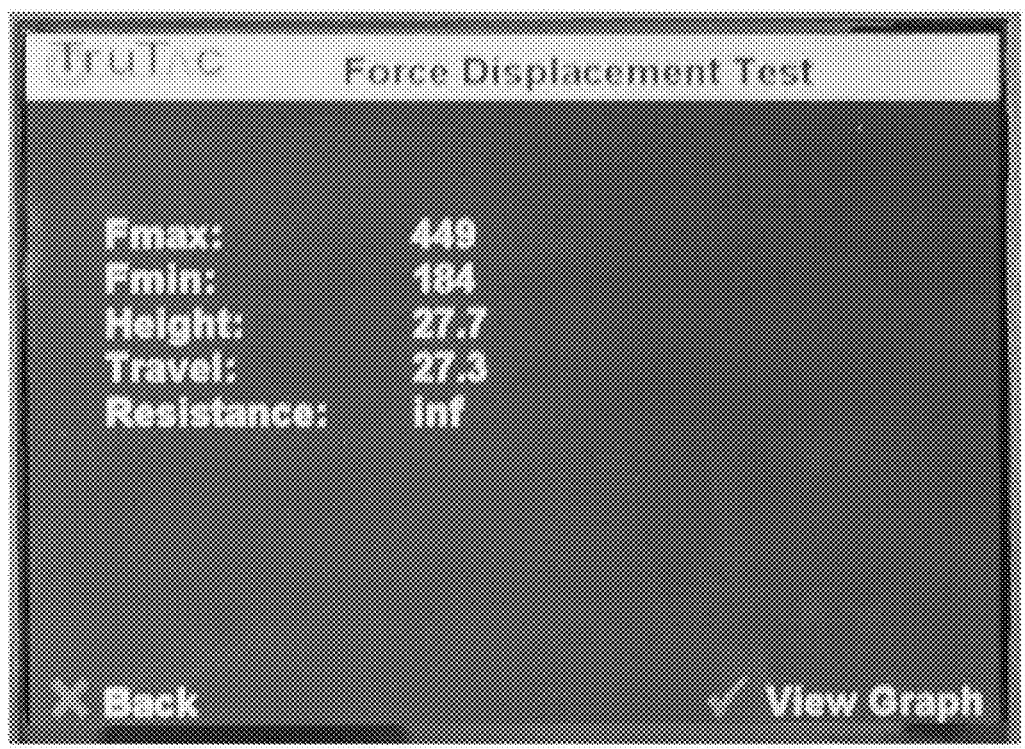
FIG. 21 shows numerical results of certain response parameters as generated by a switch dome test.
Figure 22:
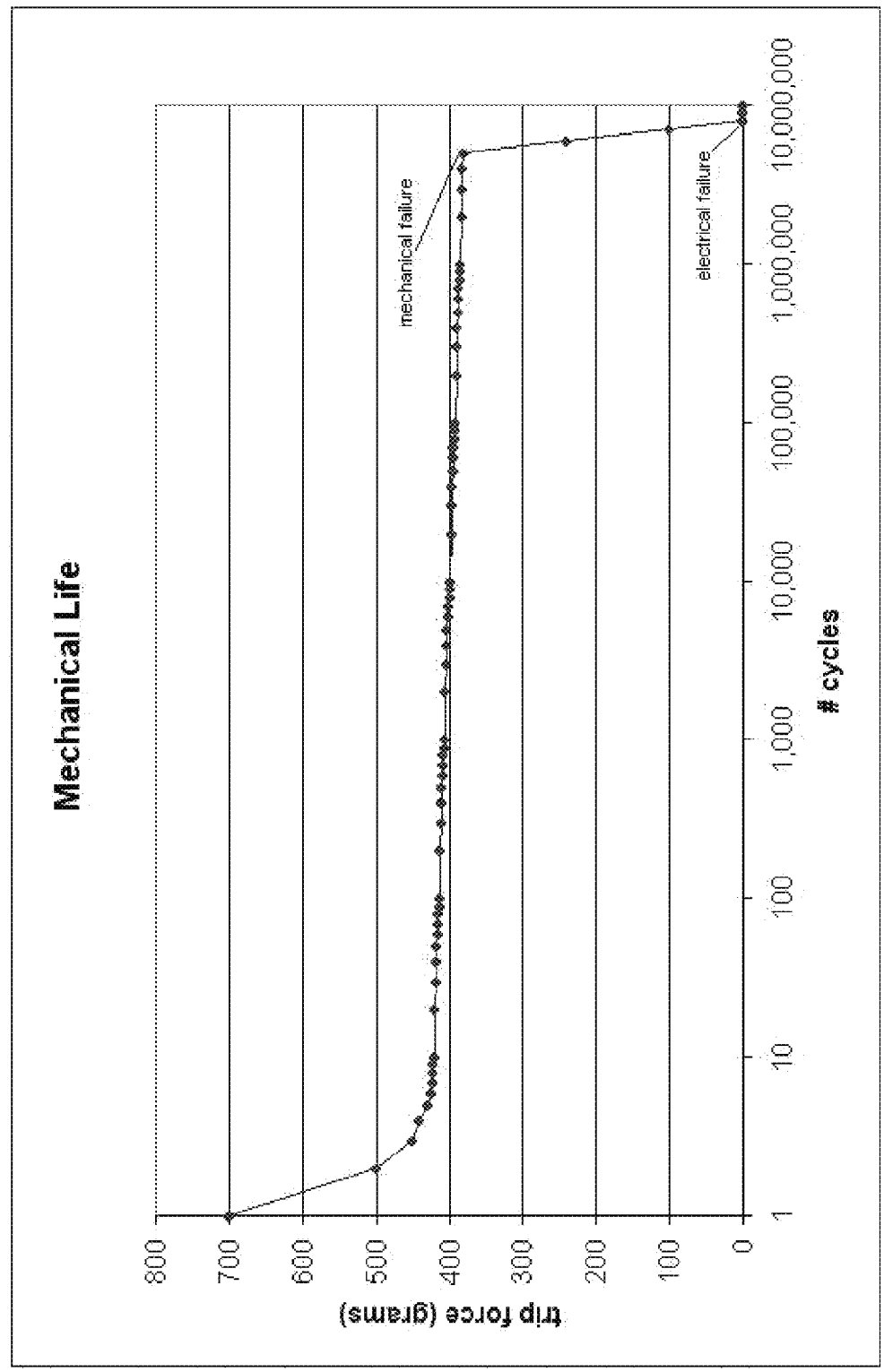
FIG. 22 shows a trip force vs. cycles graph generated by a switch dome test.
Figure 23:
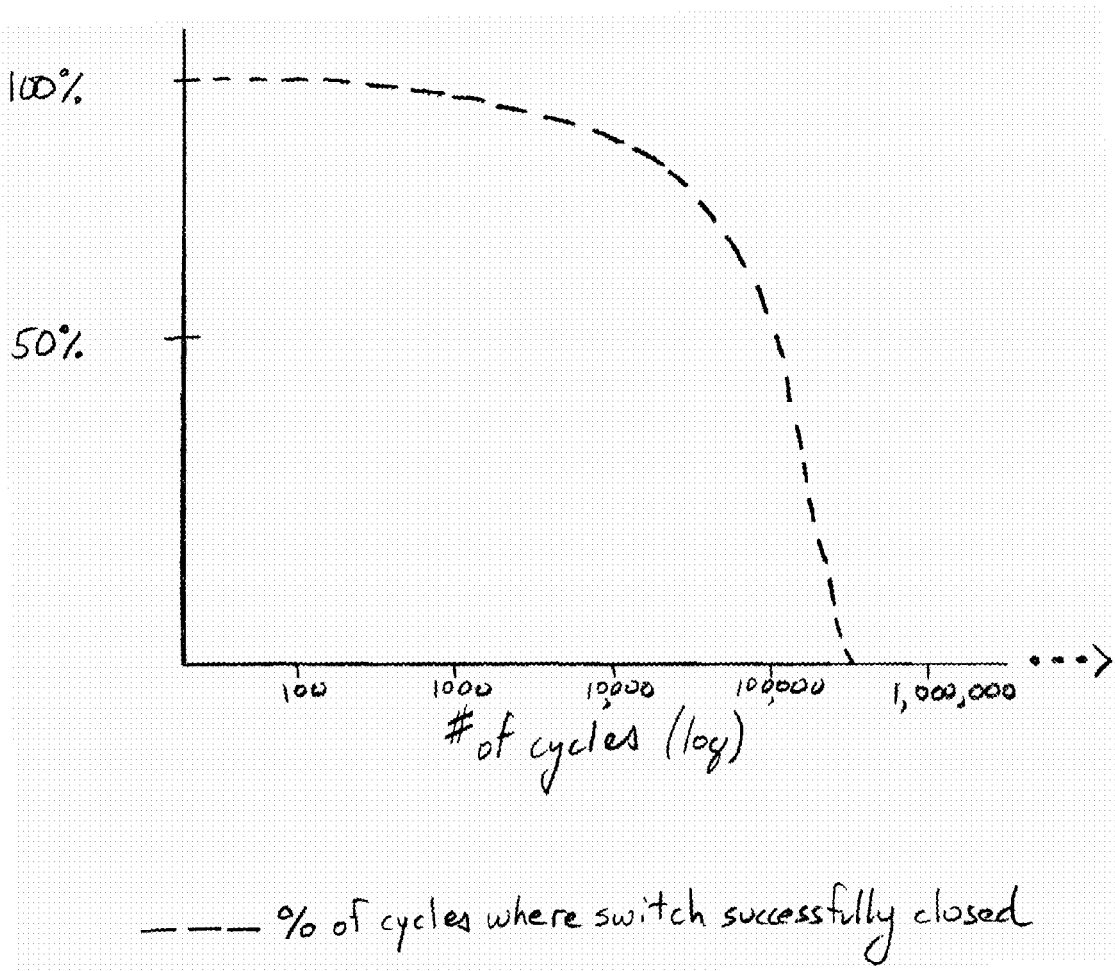
FIG. 23 shows a successful switch closure vs. cycles generated by a switch dome reliability (cyclical response) test.
Figure 24:
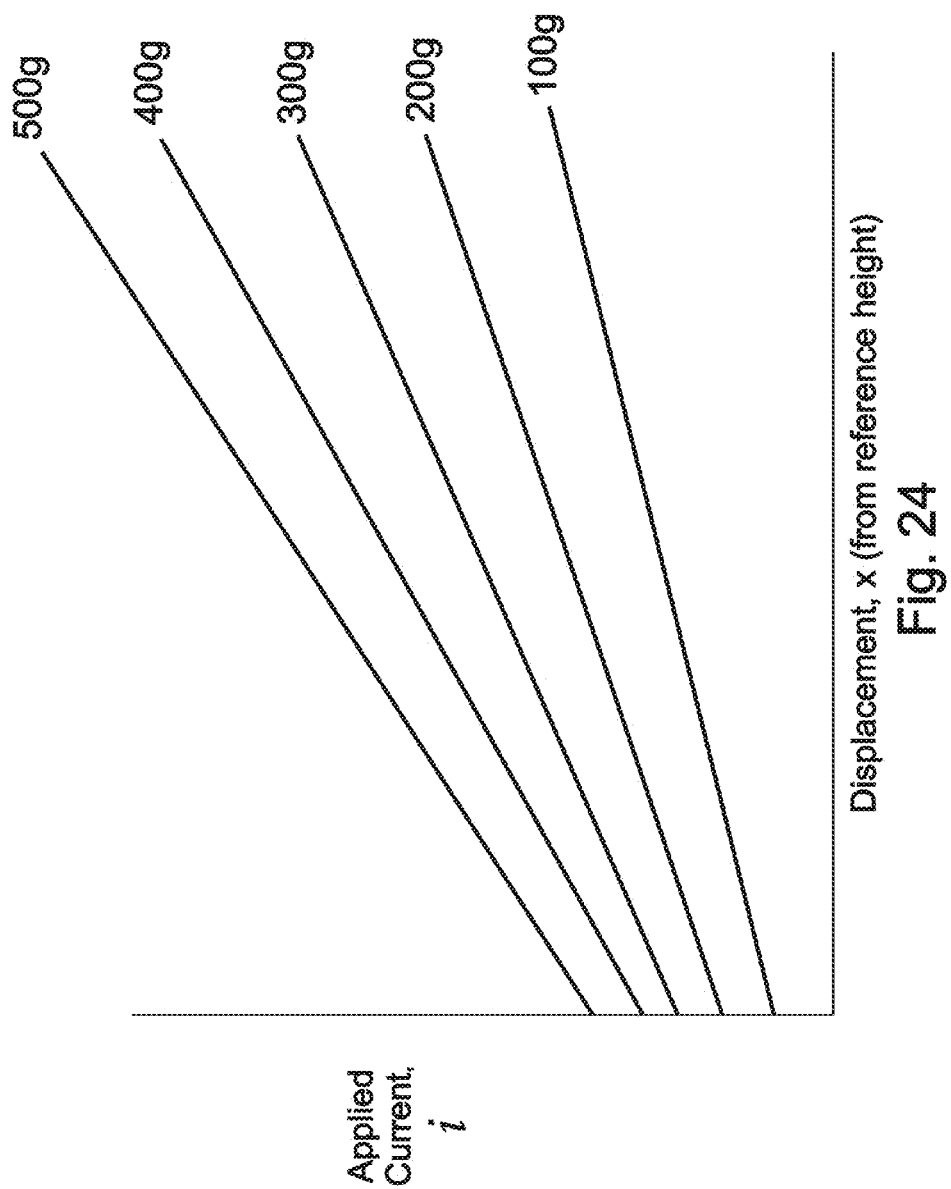
FIG. 24 shows a calibration curve.

Certain embodiments may further comprise the step of moving a force deliverer drive component 75 (i.e., a moving component that, at least in significant part, supplies the drive force; e.g., if a voice coil linear actuator is used, moving voice coil or moving permanent magnet, depending on the type of voice coil linear actuator used) at a first speed and a first acceleration (at a certain point in time) while delivering a drive force 21 to the deformation force deliverer, wherein the step of moving the deformation force deliverer comprises the step of moving the deformation force deliverer at the first speed and first acceleration and simultaneously with the step of moving the force deliverer drive component 75 (e.g., linear actuator drive component 79). It is of note that embodiments are in stark contrast to prior art, load cell, or strain gage based systems (see, e.g., FIG. 2), where the drive component and the force deliverer do not move simultaneously at the same speed and acceleration; indeed, the differences of such parameters in such prior art devices stem from the basic theory behind such devices—intentional, and often enhanced, deformation of an component (a cantilever 30) established between the drive component and the deformation force deliverer. In the inventive technology, the force deliverer drive component may be, but is certainly not limited to, a moving linear actuator component such as the voice coil or permanent magnet, depending on whether the voice coil moves or the permanent magnet moves. As the name implies, the deformation force deliverer drive component moves and thereby drives the deformation force deliverer.

Of course, and as mentioned above, the inventive methods may find various application. In certain applications, the step of moving a deformation force deliverer to deliver deformation force to a test object may comprise the step of moving the deformation force deliverer to deliver deformation force to a force activated switch dome. Also, the step of determining test object response to the deformation force may comprise the step of determining hardness and the step of determining test object response to the deformation force may comprise the step of determining elasticity. Hardness testing in particular may involve the extent of deformation in response to a quickly applied sufficiently large load.

Certain embodiments relate to cyclical failure response of the test object, where the step of determining test object response may comprise the step of determining a cyclical failure response of the test object; such embodiments may further comprise the step of repeating the steps of moving, adjusting and deforming as such steps are further described above. Such embodiments may further comprise the step of generating test object performance parameter (trip force and/or electrical resistance, as but two examples) versus cycles response data. Often, but by no means always, the test object is a force activated switch dome 25. Switch domes (tactile domes) are classic examples of items tested for cyclical failure. They are also extensively tested for other parameters (as mentioned above), including but not limited to: deformation force vs. position, maximum force, trip force, tactile ratio and electrical resistance (to determine whether the contacts are effectively made and the switch has closed or not), as but a few examples.

The inventive technology may include inventive apparatus that, in certain ways, correlate with the above-described inventive methods. Accordingly, embodiments of the inventive technology may relate to an apparatus for determining test object deformation response, comprising a deformation force deliverer 1 that delivers deformation force 24 to a test object 3; an input adjuster 30 (e.g., a current adjuster) that adjusts an input (to, e.g., a linear actuator) that affects motion of the deformation force deliverer so as to meet at least one constraint; a deformation force deliverer drive that drives said deformation force deliverer; and a test object response determiner 31 (e.g., a computer component) that determines test object response to the deformation force.

In particular embodiments of such inventive apparatus, the at least one constraint may comprise at least one deformation force deliverer motion constraint (e.g., a constant speed constraint, a constant acceleration constraint, and/or deformation force deliverer position extrema constraints). Test object response may be deformation force as it relates to deformation position (e.g., a plurality of force vs. deformation data, one piece of which could, e.g., be 23 grams of mass at 0.41 mm of deformation of the test object). Indeed, mass may be used as an indicator of force. In such embodiments, the input adjuster 30 may comprise a linear encoder 12 and a servo-controller 11, and/or test object response determiner 31 that itself may comprise recorded calibrated data 58 and a reader 59 able to read such data. Computational protocols used to generate the desired output may be as described above.

In certain embodiments, the at least one constraint may comprise at least one deformation force constraint, and the test object response may comprise deformation speed as it relates to deformation position. In such embodiments, the input adjuster may comprise recorded calibration data 58 and a servo-controller 11 (often the servo-controller itself is able to read such data), and the test object determiner 31 may comprise a linear encoder 12 (which could determine speed of the deformation force deliverer and thus, in embodiments without, e.g., a rubber tip, deformation speed). Computational protocols used to generate the desired output may be as described above.

When the input adjuster 30 comprises a servo-controller 11 and a linear encoder 12 (and, indeed, even in other designs), the test object response may comprise deformation force versus position (displacement or travel), and the at least one constraint may comprise a constant speed constraint, a constant acceleration constraint, and/or deformation force deliverer position extrema constraints (which correspond to, e.g., the deformed and maximally deformed positions of the test object). In such designs, in particular, the test object response determiner 31 may comprise recorded calibration data. Of course, whenever a component comprises recorded calibration data, there may be also provided a reader to read and perhaps output such data.

When the input adjuster 30 comprises a servo-controller 11 and recorded calibrated calibration data (and, indeed, even in other designs), test object response may comprise deformation speed (displacement speed, or travel speed) versus position. Often in such embodiments, the at least one constraint includes a constant force constraint and the test object response determiner comprises a linear encoder. Computational protocols used to generate the desired output may be as described above.

In particular embodiments, the deformation force deliverer drive 20 is a linear actuator 15, such as a voice coil linear actuator (again, including moving voice coil and moving permanent magnet types of voice coil linear actuators). Particular embodiments may further comprise a deformation force deliverer drive component 75 (e.g., a moving voice coil of a moving voice coil type linear actuator) that moves at a first speed and a first acceleration (a certain points in time), and, in such embodiments, the deformation force deliverer moves at the first speed and the first acceleration simultaneously with the deformation force deliverer drive component. As explained above, this is in stark contrast to prior art strain gauge designs.

In these, and other embodiments, the test object 3 may comprise a force activated switch dome 25 (as but one of many examples), and test object response may comprise a hardness related response, an elasticity response, and/or cyclical failure response (as but a few examples). Often, when test object response comprises cyclical failure response, the deformation force deliverer repeatedly delivers the deformation force 24 to the test object 3 to determine cyclical failure response.

Another aspect of the inventive technology may be described as a method for determining test object deformation response and may comprise the steps of: moving a force deliverer drive component 75 at a first speed and a first acceleration while delivering a drive force 21 to a deformation force deliverer 1; simultaneously moving the deformation force deliverer at the first speed and the first acceleration; deforming a test object 3 with a deformation force 24 delivered by the deformation force deliverer 1 while performing the step of simultaneously moving the deformation force deliverer at the first speed and the first acceleration; and determining test object response to the deformation force 24.

Particular embodiments of such inventive technology may further comprise the step of adjusting a deformation force deliverer affecting input so as to meet at least one constraint, whose particular aspects may be as described elsewhere in this specification (e.g., such constraints include but are not limited to test object deformation motion constraints such as constant speed or acceleration or deformation force constraints such as constant deformation force).

In particular closed loop system embodiments, the step of moving a force deliverer drive component 75 may comprise the step of powering the force deliverer drive 20 with a varying current; in such embodiments, current may be adjusted to meet a deformation force deliverer motion constraint. As such, these closed loop embodiments may be said to rely on feedback, where the feedback may be information provided by a linear encoder 12 relative to deformation speed, acceleration or position of the test object, which the servo-controller 11 can then act on so as to meet the deformation speed, acceleration or position and/or position constraint.

Certain embodiments may be more accurately described as open loop systems in that they may not rely on feedback as in the afore-described closed loop systems. In one example of such a system, the step of moving a force deliverer drive component 75 comprises the step of powering the force deliverer drive 20 with a constant current. In open loop systems in particular, the step of determining test object response may not only comprise the step of determining deformation force vs. deformation position, but the step of determining test object response may comprise the step of determining deformation speed vs. deformation position. Of course, in any system where deformation speed is not constrained (e.g., not caused to be constant), deformation speed vs. deformation position may provide valuable test object response information. Computational protocols in open loop, constant current systems may simply measure force using a linear encoder 12 (to generate deformation position data) and calibration tables to use that position data to read (perhaps while interpolating) force associated with a given current and position. Additionally, the linear encoder 12 may be useful to provide speed vs. position data.

Regardless of whether the method is closed or open loop, the step of moving a force deliverer drive component 75 may comprise the step of delivering current to a linear actuator 12. Further, the step of deforming a test object 3 may comprise the step of deforming a force activated switch dome 25, the step of determining test object response to deformation force may comprise the step of determining hardness, determining elasticity, and/or determining a cyclical response. When the method relates to determining cyclical response (e.g., cyclical failure response), the method may further comprise the step of repeating the steps of moving a force deliverer drive component 75, simultaneously moving the deformation force deliverer 1, and deforming a test object with a deformation force. In such embodiments, the method may further comprise the step of generating test object performance parameter versus cycles response data (e.g., the maximum force, and/or the electrical resistance at 1, 100, 100, 1,000, 10,000, 100,000 cycles, perhaps until failure). Of course, data relative to the number of "pass/fails" relative to meeting a certain parameter in a given number of cycles may be generated. Whether the test object 3 is a force activated switch dome 25 or something else, the test object performance parameter may comprise trip force and/or an electrical resistance, as but two examples. Of course, electrical resistance may be used to indicate whether a switch has closed or not; a substantially infinite resistance (or, at least, very high) may be associated with an open switch while a resistance reading of less than a certain amount (e.g., less than a certain ohmage) indicates closing of a switch. The apparatus may provide information, e.g., relative to the number of successful switch closings or purely elastic deformations (e.g., no plastic deformation, which may signify failure), observed over a certain number of cycles.

An aspect of the inventive technology related to that method described directly above may be described as an apparatus for determining test object deformation response and may comprise: a force deliverer drive component 75 that moves at a first speed and a first acceleration while delivering a drive force 21; a deformation force deliverer 1 to which the drive force 21 is delivered and that moves at the first speed and the first acceleration to deliver deformation force to a test object 3; and a test object response determiner 31 that determines a response of a test object to the deformation force, wherein the deformation force deliverer is capable of delivering a deformation force to the test object, and wherein the deformation force deliverer moves simultaneously with the force deliverer drive component 75.

The apparatus may further comprise an input adjuster 30 that adjusts an input that affects motion of the deformation force deliverer so as to meet at least one constraint. In those embodiments where the test object response determiner is capable of determining deformation force vs. deformation position, the at least one constraint may comprise a test object deformation speed and/or acceleration constraint, and, perhaps also the aforementioned position extrema constraints. Further, in such embodiments, the input adjuster may comprise a servo-controller 11 and a linear encoder 12, while the test object response determiner 31 may comprise recorded calibration data, and a computer component capable of reading such data. In those embodiments where the test object response determiner is capable of determining speed vs. deformation position, the at least one constraint may comprise a test object deformation force constraint. Further, in such force constraint embodiments, the input adjuster may comprise recorded calibration data and a servo-controller 11, and the test object response determiner may comprise a linear encoder 12.

As with other aspects of the inventive technology, particular embodiments of this apparatus may be described as closed or open loop. In closed loop systems, the force deliverer drive 20 may be powered with a varying current (albeit one varied in a controlled fashion, as where current is varied to meet a deformation force deliverer speed constraint or deformation force constraint) while moving at a first speed and a first acceleration while delivering the drive force; the test object response determiner 31 may determine deformation force vs. deformation position, and/or the test object response determiner may determine deformation speed vs. deformation position.

In what may more accurately be described as an open loop apparatus, the force deliverer drive component 75 may be powered with a constant current while moving at a first speed and a first acceleration while delivering the drive force. In such embodiments (and, indeed, in others), the test object response determiner 31 may determine deformation force vs. deformation position and/or the test object response determiner may determine deformation speed vs. deformation position.

Regardless of whether the inventive apparatus is closed or open loop, the deformation force deliverer drive component 75 may comprise a linear actuator component 79 (again, such as a moving voice coil or a moving permanent magnet); the linear actuator may be a voice coil linear actuator (e.g., a moving voice coil linear actuator or a moving permanent magnet voice coil linear actuator). As with other aspects of the inventive technology, applications are varied; the test object may 3 be a force activated switch dome 25 (as but one example of many possible test objects), and test object response includes but is not limited to hardness-related response, elasticity response, and cyclical response, such as cyclical failure response. In those embodiments used for cyclical failure testing, the deformation force deliverer may repeatedly delivers the deformation force 24 to the test object 3 to determine cyclical failure response.

Particular aspects of the inventive technology are linear actuator limited. As such, a method for determining test object deformation response may comprise the steps of: delivering current to a linear actuator 15; moving a deformation force deliverer to deliver deformation force to a test object while performing the step of delivering current; deforming the test object 3 with the deformation force 24; and determining test object response to the deformation force.

Such aspects may further comprise the step of adjusting a deformation force deliverer affecting input (e.g., current applied to a linear actuator) so as to meet at least one constraint (deformation force deliverer motion constraint such as a test object deformation speed constraint or a test object deformation acceleration constraint, or, on the other hand, a deformation force constraint). Particularly when the constraint is a deformation force deliverer motion constraint, the step of determining test object response may comprise the step of determining deformation force vs. deformation position. Further, in such embodiment, the step of adjusting the deformation force deliverer affecting input may comprise the step of adjusting the current. Indeed, embodiments with constraints (which may be referred to as closed loop embodiments), the step of delivering current to the linear actuator may comprise the step of delivering varying current to the linear actuator. When the constraint is a deformation force constraint, the step of determining test object response may comprise the step of determining deformation speed vs. deformation position. In aspects of the inventive technology that do not include such constraints, and thus which may be more accurately be described as open loop, the step of delivering current to the linear actuator may comprise the step of delivering constant current to the linear actuator. In open loop systems, not only might it be helpful to determine force vs. position, but what might also be revealing is deformation speed vs. deformation position data. Of course, as mentioned, deformation speed vs. deformation position data may also be revealing in closed loop embodiments that have a force constraint (e.g., a constant force).

Particular embodiments may further comprise the step of moving a linear actuator drive component 79 (a moving voice coil or a moving permanent magnet, as but two examples) at a first speed and a first acceleration while delivering a drive force 21 to the deformation force deliverer 1; in such embodiments, the step of moving the deformation force deliverer 1 may comprise the step of moving the deformation force deliverer at the first speed and first acceleration and simultaneously with the step of moving the linear actuator drive component 79.

As mentioned, applications of this technology are varied. As such, the step of deforming the test object may comprise the step of deforming a force activated switch dome 25 (as but one example of many possible test objects). The step of determining test object response to the deformation force may comprise the step of determining hardness, the step of determining test object response to the deformation force may comprise the step of determining elasticity; and/or the step of determining test object response to the deformation force may comprise the step of determining a cyclical response (e.g., cyclical failure response). In those embodiments directed at life cycle response testing (whether failure related or otherwise), the inventive methods may further comprise the step of repeating the steps of moving the deformation force deliverer, and deforming a test object. In such embodiments, the step of determining test object response may comprise the step of determining a cyclical failure response of the test object (e.g., a force activated switch dome), and the method may further comprise the step of generating test object performance parameter versus cycles response data (e.g., trip force or an electrical resistance).

Apparatus corollary to the above-described inventive method technology may be described as an apparatus for determining test object deformation response and may comprise a linear actuator 15 that moves a deformation force deliverer 1 that delivers deformation force 24 to a test object 3; and a test object response determiner 31 that determines a response of the test object 3 to the deformation force 24.

Particular embodiments may further include an input adjuster 30 that adjusts an input that affects motion of the deformation force deliverer so as to meet at least one constraint. In such embodiments (which may be described as closed loop embodiments), the test object response determiner may be capable of determining deformation force vs. deformation position (particularly in those embodiments with at least one deformation force deliverer motion constraint). In such embodiments, constraints may include but are not necessarily limited to a test object deformation speed constraint and/or a test object deformation acceleration constraint. In such embodiments, the input adjuster 30 may comprise a linear encoder 12 and a servo-controller 11.

In closed loop embodiments where the test object response determiner 31 is capable of determining speed vs. deformation position (which may be found when the constraint is a deformation force constraint), the input adjuster 30 may include a servo-controller 11 and recorded calibration data (and perhaps a computer component capable of reading such data if the servo-controller itself does not include such reading capability). In those embodiments where test object response determiner 31 is capable of determining speed vs. deformation position, the test object response determiner may include a linear encoder 12.

In closed loop systems, the linear actuator 15 may be powered with a varying current while delivering a deformation force. In open loop systems, the linear actuator may be powered with a constant current while delivering a deformation force. In either such embodiments, the test object response determiner 31 may determine deformation force vs. deformation position and/or deformation speed vs. deformation position. As mentioned, a typical closed loop system designed to generate deformation speed vs. deformation position data will operate under a constant force constraint while a typical closed loop system designed to generate deformation force vs. deformation position data will operate under a constant deformation speed (or acceleration) constraint; in either, current input may be adjusted to meet such constraints. A typical open loop system will operate under a constant current constraint (e.g., a constant current fed to a linear actuator) and may use a linear encoder 12 to generate deformation speed vs. deformation position data, or a linear encoder 12 and calibration data 58 to generate deformation force vs. deformation position data (of course, the deformation force may be read using measured deformation speed and position data).

As in other aspects of the inventive technology, a drive component 75 (moving voice coil, e.g., if a linear actuator 15 is used) may move at a first speed and a first acceleration, and the deformation force deliverer 1 may move at the first speed and the first acceleration simultaneously with the drive component. Regardless, the applications are, as with other aspects of the inventive technology, quite varied. The test object may be, but is certainly not limited to, a force activated switch dome 25, and test object response may be a hardness related response, an elasticity response, and/or a cyclical response (e.g., a cyclical failure response). Particularly where the response to be determined is a cyclical response, the deformation force deliverer may repeatedly deliver the deformation force to the test object to determine cyclical failure response.

It is of note that, for each of the inventive aspects, componentry may be configured/housed in a variety of manners. One is a test station 80 (e.g., a Tru-Tac™ test station) that includes an interface 81 (in which may be housed, e.g., a linear actuator and linear encoder) from which may extend a deformation force deliverer 1, support arm 82 for the interface, base plate 83 above a base 84 in which may be housed a servo-controller and other electrical componentry, test object block locator 85 adapted for securement on the base plate, and a power supply 86. Of course, this is merely one of many different ways of configuring the inventive apparatus. Associated electrical/computer parts that may enable co-functionality of electrical componentry as intended may include, but is certainly not limited to a motherboard, data acquisition card. amplifiers, resistors, shunt resistors to assist in monitoring current (to, e.g., a voice coil), jacks, switches, RAM, etc., as would be readily understood from one of ordinary skill in the art upon reviewing the supplied electrical diagrams. Of course, any specifications/dimensions/product models, etc. shown in the figures or otherwise described in this application are merely exemplary and do not in any fashion limit the scope of the inventive technology.

Aspects of the inventive technology may include CPU and other hardware, and software, necessary to render the unit entirely controllable via computer. Software, whether in C++, Java, or other, may facilitate user-control and operation of the tester via. A webserver may allow coordination of the unit with the internet, thereby allowing enhancing functionality, communication and manipulation of results, in addition to coordination of separate units in desired fashion. Computer control of the test may allow for comprehensive control of testing protocol, including the ability to test to provide results that accord with anticipated use of the object, or for other reasons. For example, a simple testing protocol enabled by the enhanced computerized control exhibited by the inventive technology is, as but one of countless examples, test for force vs. displacement, test for electrical performance, cycle 5,000 times, test for force vs. displacement, test for electrical performance, cycle 10,000 times, test for force vs. displacement, test for electrical performance, cycle 1,000 times, etc.

In particular embodiments, a focus of the inventive technology may indeed be on the use of a voice coil in combination with a linear encoder and controller to provide positional, speed and/or acceleration information about linear motion of a deformation force deliverer such as a linear actuator shaft (generally, a servo-motion based technique). It should be understood that whenever a voice coil is used to drive a deformation force deliverer in a linear manner, such is considered a voice coil linear actuator. It should also be understood, for purposes of clarity, that explanations of, e.g., specific terms, that appear in this disclosure typically apply to all uses of such terms.

Additional disclosure relative to use of embodiments of the inventive technology may be as follows (of course, detailed specification, including but not limited to dimensions, below and in other parts of the application, are merely exemplary). Reference to TruTac™, in addition to any descriptive text appearing below (other than the claims), is merely explanatory relative to this specific test station; it shall not limit the scope of the claims in any manner.

Overview of the TruTac™ Force Displacement Test Station:

The TruTac™ force displacement test station is capable of accurate, repeatable force tests on various types of switches and switch assemblies. It is a stand alone unit that tests and displays measurement readings to the user via its incorporated LCD panel, or in tandem with a PC. Single or multiple TruTac test stations can also be integrated with a company network so data can be programmed, viewed, and downloaded remotely. The TruTac can be used to test metal domes, poly domes, membrane switches, and most other switches, depending on tester configuration. It may be the first tester to comply with ASTM standards, and tests include trip force, return force, standing free height, displacement (travel), tactile ratio, tactile slope, and switch resistance. The TruTac™ can also test the life of a switch and be programmed to conduct intermittent tests for mechanical and electrical failures. Life testing speeds of 20 actuations per second are possible depending on switch travel.

Features

First switch test unit to conform to new ASTM 2592 standard

Tests trip force, return force, free height, displacement, tactile ratio, tactile slope, resistance, life, and more Compact design Built in LCD with intuitive displays PC and network compatible Fast and accurate tests Pre-drilled and threaded testing platform for custom tooling plate configurations Custom features available Set Up The TruTac test station comes complete with the base, support arm, and interface screen preassembled. A power supply, power cord, and applicator tips are also included.

Set-up

1. The TruTac test station will arrive packaged in a box with foam padding to protect it during shipping. Upon receiving your TruTac unit, remove the TruTac box from the shipping box. Open the top of the TruTac box and remove the foam packaging to reveal the test station. Carefully remove the top of the foam padding so that the TruTac test station is visible. Gently remove the TruTac while holding the interface stand (Exhibit D) and place it on a solid surface. The power supply (Exhibit E), power cord (Exhibit L), and bag containing both actuator tips (Exhibit C) are located under the TruTac unit.

Note: Hold the unit by the silver stand when handling the TruTac test station. Never hold the TruTac test station by the interface control box.

2. The test unit will operate best if placed on a solid table that is free from vibrations. Avoid placing any part of the system closer than necessary to sources of electrical or magnetic disturbance such as computer monitors, speakers or fluorescent lights.

3. Connect the AC power cord from the power supply into a wall socket or power strip. Connect the DC power cable from the power supply to the unit.

4. Turn the power switch to the "on" position. Allow 2 minutes for the system to boot-up.

PC Access

In certain models the TruTac can be used in conjunction with a PC via Ethernet connection to get detailed test information and reports. Graphical User Interface (GUI) software comes pre-installed on the TruTac test station, and runs on the user's web browser using Java technology. Since the software is web browser based, data can be programmed, viewed, or downloaded remotely from any computer which has authorized access to your company network.

To access software screens on a PC, you may connect an Ethernet cable to the back of the TruTac test station. Open your web browser (e.g. Google, MSN, Yahoo, etc.) and type the name of the test station (or IP address) in the navigation bar. The TruTac test station is designed to automatically acknowledge your network IP address once connected.

Note: The test station name and IP address can typically be found on the TruTac test station by scrolling to About on the main screen and pressing Enter.

Note: The TruTac typically comes pre installed with Java Runtime version 1.6. It will automatically try to determine if you have a compatible Java Runetime version already installed on your PC. If not, it will direct you to a link with information on how to download the appropriate Java version.

Note: The TruTac test station typically can be connected to a stand alone PC using a cross over Ethernet cable.

Note: Some networks may have security measures that will block automatic login. Contact your IT Network administrator if the network is not automatically acknowledged.

In certain models a warning message that reads "The application's digitial signature cannot be verified. Do you want to run the application?" may be displayed when first logging in to the graphic interface software. Select Run to grant permission to access your network.

Note: The TruTac test station may be compatible with Internet Explorer versions 6.0 and 7.0, Firefox, and Opera. Use Java Runetime Engine v1.5 or v1.6.

Note: A copy of Java software (which can be downloaded to your PC) and the TruTac user's manual may be contained on the CD that come with the TruTac test station.

User Interface

In certain models the user interface on the TruTac test unit may include an LED interface display screen, and five keys (Up, Down, Back, and two Enter buttons).

Depending on the test being performed, the LED display screen may display commands at the bottom of the screen to help the user navigate to the appropriate area.

Main Screen

In certain models the stand alone inspection mode may allow the user to get test data directly from the user interface screen of the TruTac test station. Test data may include Fmax, Fmin, height, travel and resistance.

Note: To get accurate results, the actuator tip should actuate directly in the center of the switch.

The default screen on the user interface may have the following options:

Force Displacement Test
Height Test
Locate Plate
View Results
Settings
About

Force Displacement Test

In certain models to conduct a force displacement test, scroll to Force Displacement Test on the main screen and press the Enter key.

Line up the center of the switch with the actuator tip by either 1) pulling down on the actuator, or 2) using the Jog Down key command, until the actuator is positioned in the center. Return the actuator to its original position.

Once the switch is centered properly, select the Enter key to conduct the test.

Note: You may wish to pre-actuate your switch prior to conducting a test. See Settings (page 16, 17) for settings information.

Once you select Enter, a message will appear on the LED display screen indicating that the "Test is running . . . ". Once the test is complete, the screen will list results for:
Fmax
Fmin
Height
Travel
Final Resistance Select the Enter key to switch back and forth between the View Graph and view text screens. Select the Back key to return to the main menu.

The bottom of the screen gives you the options to go Back or View Graph. The Back key will bring you to the main screen. The Enter key will allow you to view a force displacement curve showing Forward Force, Resistance, and Reverse Force.

Height Test

In certain models to conduct a free height test, scroll down to Height Test on the main screen and press the Enter key.

Line up the center of the switch to be tested with the actuator tip by either 1) pulling down on the actuator, or 2) using the Jog Down key command, until the actuator is positioned in the center. Return the actuator to its original position.

Once the switch is centered properly, select the Enter key to conduct the test.

A data screen will appear with the free height of the switch being tested. Press the Back button to return to the main screen.

Note: Prior to conducting the first test, it is advised to locate the testing plate in order to get the zero position. See Locate Plate (page 8) for to see procedures for locating the test plate.

Locate Plate

Prior to conducting the first test, it is advised to locate the testing plate in order to get the zero position. This test will record the position of the plate which is necessary to get accurate measurement readings.

In certain models to locate the testing plate from the main screen, use the down arrow key to scroll to Locate Plate and press the Enter key. A message reading "Locating plate" will display on the screen while the actuator finds the zero position. Once that position is recorded, the main screen will reappear and you can proceed with testing.

Note: The Locate Plate function must be run if the testing plate height has changed to provide a new zero reference for measurement. The value of the last Locate Plate function will remain valid even if the TruTac test station is powered off.

Warning: In certain models do not test directly on the testing platform as it may cause damage to the surface. Always use a testing fixture plate.

View Results

In certain models the view the results of the most recent test run, scroll on the main screen to the View Results and press the Enter key.

A data screen will appear that lists the following results of the most recent test:
Date
Time
Fmax
Fmin
Free Height
Travel
Resistance Settings In certain models the settings screen allows adjustment to:
Pre-actuations
Contact threshold
Enable/disable reverse curve
Force level To view the settings screen, scroll down to Settings on the main screen and press the Enter key.

The following commands will be listed at the bottom of the settings screen.
Main (returns to the main screen)
Scroll Up
Scroll Down
Edit (allows you to adjust settings)

To adjust a setting, use the Scroll Up or Scroll Down keys to a desired setting and select the Enter key. Adjust the setting by using the up or down keys. Once the desired setting is reached, select the Enter key.

The following are the adjustment ranges:
Pre-actuations: 0-100 actuations
(actuates the switch before running the test)
Contact threshold*: 1-1,000 Ohms
(threshold used to determine when contact has been made during the actuation of a switch)

Enable/disable reverse curve: Yes/No
(determines whether a reverse curve test is executed or not)

Once you have entered your desired settings, select the Back key to return to the main menu

* Contact threshold is used to calculate ASTM values of contact force (Fc), break force (Fb), travel contact (Tc), and travel break (Tb)

About

In certain models the about screen displays general information about the test unit. To view the about screen, scroll down to About on the main screeen and press the Enter key.

In addition to general Snaptron, Inc. Information, the following is displayed on the About screen;
Software version number
Hardware version number
Network name
Network IP Address Select the Back key to return to the main menu.

Connecting

In certain models the TruTac test station may be pre-programmed so no special software installation is required. The TruTac test station software screens are displayed via your web browser. Once you have accessed the graphic interface screen on your PC, the user can run tests and view data remotely.

Note: Please see PC Access (on page 7) for information on connecting to the PC graphic interface screen.

There are four PC graphic interface tabs:
1. Force Test tab
2. Locate Devices tab
3. Life Test tab
4. Tools/Settings tab Force Test In certain models the graphic interface screen will default to the Force Test tab. On this tab, a force curve is generated mapping data pertaining to force measured in grams), travel (measured in thousandths), and resistance (meausured in Ohms).

In the Force Test tab the user can execute a force test and view the results—including Fmax, Fmin, travel, height, and resistance. The user has the option to run and view the results of a test, and to save all the raw test data to a comma separated file (.csv). Prior to running a test, conduct the Locate Plate function (page 14) on the TruTac test station. Once the zero position has been determined, place the center of a switch directly under the actuator. Select the Run Test button on the PC screen to initiate the test and view the results.

There are three icons at the top of the Force Test tab:
1. Save test data to file (left)
2. Generate test report (middle)
3. View user manual (right)

Save Test Data to File

In certain models after completing a test, selecting this icon will save raw test data to the location you select in an .csv format. Columns that represent the raw data are 1) position (th), 2) force (g), and 3) resistance (Ohms).

Generate Test Report

In certain models this function takes HTML report information and converts it into PDF format. The report can then be printed, attached to an existing document, emailed, etc. The standard report lists ASTM standards, including Fmax, Tfmax, Fmin, Tfmin, Fc/Fb, Tc/Tb, tease force, tease travel, free height, travel, tactile response slope, tactile recovery slope, tactile ratio, resistance threshold, and resistance (end of test). The standard report also includes the force displacement curve and an area to add notes. Reports for the most recent test conducted is automatically saved on the TruTac unit. In addition to the standard report, custom reports can also be added. See Tools/Settings (page 23) for information on creating custom reports.

View User Manual

This opens a PDF of the TruTac user manual.

Locate Device Tab

In certain models the Locate Device tab is for users who have multiple TruTac test stations on their network and are wanting to locate a specific unit or units. Selecting the Search button will send out a network broadcast and all TruTac test stations that are on the network (and turned on) will automatically reply back.

All connected TruTacs will be populated on the list menu. A single click on a device name will display the general information, including current software revision, model number and serial number of the unit. A double click on the device name will open a new window in the user's web browser, load the software screen of that device, and establish a connection with that device.

Life Test Tab

In certain models the Life Test tab shows data (number of cycles and force readings) of the current or most recent life test. The user can also set and adjust parameters for life testing, including the number of cycles to run, intermittent and final force readings, and the force in which a switch is life tested (ranges measured in grams). The progress of a life test is displayed on the screen.

Note: The options for the force levels on the Life Test tab controls the force during life cycle testing AND force readings. When a life test is being conducted, the force range selected overrides the settings for force testing selected in the Tools/Settings tab.

In certain models, there are two options for testing the life of a switch:

Option #1

The user enters the total number of cycles, at what intervals to conduct a force test, and the force level at which to run the force tests.

In certain models the user then selects the Start button on the PC screen and historical data is recorded on the graph.

Option #2

In certain models the user can create a test script file using a simple set of commands and upload this to the TruTac test station. To do this, select the Use Recipe File followed by selecting the Load Recipe button. This will upload the command codes from a text file.

Commands may be as follows:
doforcetest—Conducts a force test
cycle XX—Conducts life tests whereas "XX" is the number of cycles An example of a test script is shown below:
doforcetest
doforcetest
doforcetest
doforcetest
cycle 10
doforcetest
cycle 20
doforcetest Upon executing the test script, the TruTac will do the following:
4 force tests
Cycle the switch 10 times
1 force test
Cycle the switch 20 times
1 force test
Test complete In certain models the user has the option to save the test data to a comma seperated file (.csv) that includes a timestamp, force readings, and resistance readings. To save the data, select the icon at the top of the PC screen.

The bottom of the PC screen shows both the Cycle Count and Actuation Count. The cycle count indicates the amount of times each dome is actuated, while the actuation count shows the amount of electrical actuations (circuit being completed) being achieved.

Note: The user has the option to connect the switch under the test resistance connection.

Note: The cycle rate can be adjusted to approximately 20 cycles per second, depending on the travel of the switch being tested.

Tools/Settings Tab

In certain models there are five categories in the Tools/Settings tab; force test parameters, test reports, network, software update, and process control mode.

Category 1: Force Test Parameters

Contact Threshold: Refers to the resistance measurement on a switch and is measured in Ohms. When resistance falls between the set levels, it is considered an actuation.

Pre-Actuations: Refers to the number of actuations conducted prior to the force reading test. Pre-actuations are suggested to stabilize the switch prior to the force reading. The range for pre-actuations is 0 to 100.

Force Level: Refers to the amount of force used to actuate the dome to conduct a force test. Feedback may be used to assure compliance with range limits. Ranges include, but are not necessarily limited to:

0 g to 300 g
300 g to 600 g
600 g to 900g

Reverse Curve: Refers to the presence of a reverse curve on the force test. When the reverse curve box on the PC screen is checked, the reverse curve is enabled. When the box is unchecked, the curve is disabled.

Category 2: Test Report

Upload Logo: Allows you to upload a logo into the default template. Logos must be in a .bmp format with maximum size parameters of 150 pixels×50 pixels.

Upload Template: Allows you to upload a custom report template (text based document) based on your desired criteria. Report templates are created using HTML coding. Once uploaded, the report is converted to a PDF when the "Generate Test Report" icon is selected.

Note: Some knowledge of HTML coding is required to create and upload a custom test report. If necessary, contact Snaptron for assistance creating custom test reports.

Restore Default Template: This will reset the report template back to the default template (ASTM standards).

Category 3: Process Control Mode

In certain models the user can apply limits to all ASTM values via an Upper Spec Limit (USL) and a Lower Spec Limit (LSL).

Fields for the ASTM standards are Fmax, Fmin, Frmax, Frmin, TfMax, TfMin, Fc/Fb, Tc/Tb, tease force, tease travel, free height, travel, tactile response slope, tactile recovery slope, tactile ratio, resistance threshold, final resistance.

When the Process Control Mode is Enabled, the front panel of the TruTac test station locks, and the top button on the unit is used to conduct force tests. Data is streamed from the TruTac test station, through the PC interface screen, to a text file. All ASTM values are saved in the text file. The TruTac screen will indicate Pass or Fail if any one of the ASTM values entered in out of the selected range.

Category 4: Software Update

In certain models selecting the "Check for Update" in the Software Update category will look for the latest version of the TruTac software and, if found, download and install the update.

Category 5: Network Settings

In certain models this allows you to adjust the network settings for the TruTac test station, including the host name, IP address, gateway, subnet, and DHCP server. Contact your IT professional or Snaptron for information regarding these settings.

System Components
    TruTac test unit
    0.050" actuator tip
    Power supply
    Power cable TuTac Test Station Specifications
Power Requirements:
    Rated voltage (100-240VAC)
    Line frequency (47-63 Hz
    Current (2.2 A max. at 90 VAC input)
Weight:
TruTac (13.5 lbs.)
Power supply (1.5 lbs.)
Unit Dimensions:
11 W×11 L×10.2 H (in)
Screen Dimensions:
2.9 W×2.1 H (in)
Throat Dimensions:
3.1 H×5.0 D (in)
Power Supply Dimensions:
9.0 L×2.9 W×2.0 H (in)
Screen Resolution:
640×480 pixels
Software Compatibility:
Java Runtime Environment (version 1.5 or newer)
Testing Specifications (In Certain Models):
Curve Generation:
    Force vs. displacement line graph
    A graphical representation of a switch's tactile feel
Measurement Units:
Grams, 10-3 inch
Max Displacement:
0.60 (in.)
Max Force:
1200 (grams)
Displacement Accuracy:
+/−0.005 (in)
Force Accuracy:
+/−5 (grams)
Resistance Accuracy:
+/−0.00
Resistance Range:
0-1000 Ohms
Max Life Test Speed:
20 cycles per second
Max Life Test Stroke:
0.60 (in.)
Testing Terms/Explanations (Non-Binding, but Clarifying Explanations may be as Follows):

Force: Mechanical resistance to motion (e.g., in grams or ounces).

Displacement: Measured distance of movement when a test object is depressed (may be referred to as travel or deformation position).

Free Height: Measurement taken from the top of the test object to the surface in which the switch is resting.

Travel: Displacement with specified start and finish; in case of a switch, usually starts when force exceeds zero and finishes when switch contact occurs.

Resistance: Electrical resistance as measured between two test points whose internal contacts, when held closed, complete a circuit.

Contact threshold: Indicates the threshold levels set for desired resistance measurement of a switch.

Force curve (forward): Shows the hysteresis of the relationship between force applied and displacement in the forward movement of a test object.

Release curve (return): Shows the hysteresis of the relationship between force and displacement in the return movement of a test object.

Fmax (actuation force): Maximum force measured prior to or including point (Fmin). Sometimes referred to as the actuation force.

Fmin (release force): Minimum force seen between Fmax and point at which probe movement ceases. Sometimes referred to as release force.

Frmax: Return max force. Maximum force measured during return cycle after achieving Frmin.

Frmin: Return min force. Minimum force seen during return cycle before reaching Frmax.

Tfmax: Displacement at Fmax (forward movement).
Tfmin: Displacement at Fmin (forward movement).
Tfrmax: Displacement at Frmax (return movement)
Tfrmin: Displacement at Frmin (return movement).
Fc: Contact force (the force at contact closure).
Fb: Break force (the force at contact break).
Tc: Contact displacement (the displacement at contact closure).
Tb: Break displacement (the displacement at contact break).

Tease force: The displacement measurement on the force-displacement curve between contact force (Fc) and minimum force (Fmin).

Tease travel: The amount of displacement where switch contact is not made between contact force (Fc) and minimum force (Fmin).

Tactile response slope: Rate of change of applied force with respect to displacement, as measured between Tfmax and Tfmin.

Tactile recovery slope: Rate of change of return force with respect to displacement, as measured between Tfr min and TFrmax.

Tactile ratio: Combination of actuation force (Fmax) and release force (Fmin). Measured as Fmax−Fmin/Fmax (×100).

Resistance threshold: Point at which test object is considered actuated. Final resistance: Reading at end of test.

Care and Handling
  When cleaning the LCD, buttons and cases, use a soft damp cloth only. Do not use solvents or scouring agents.
  Do not submerge the unit or power supply in any liquid.
  Extra care should be taken when handling the force applicator tip as the internal support bearing can be damaged.
  Torque transmitted to the actuator shaft should be kept to a minimum and not allowed to exceed 1.3 N-m (11 lbf-in).
  The force applicator should be cleaned with a dry, lint free cloth. It should be free of any visible contamination and should more freely by hand.
  When picking up or moving the test station, always hold it by the support arm or the base of the unit.
  Test tips are attached via threads that attach as part of the force applicator. To remove a test tip, unscrew going counter clockwise.
  The TruTac may have pre-drilled and threaded platform holes for custom tooling plate configurations. Never drill holes into the base as it may damage the functionality of the unit.
  It is recommended that calibrations of the TruTac test station are conducted every 6 months in order to ensure the most accurate readings.

As can be easily understood from the foregoing, the basic concepts of the present invention may be embodied in a variety of ways. It involves both deformation response testing techniques as well as devices to accomplish the appropriate testing. In this application, the testing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this international application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and is designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "determiner" should be understood to encompass disclosure of the act of "determining"—whether explicitly discussed or not— and, conversely, were there effectively disclosure of the act of "determining", such a disclosure should be understood to encompass disclosure of a "determiner" and even a "means for determining" Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in any information disclosure statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the deformation response determination devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An apparatus for determining test object deformation response, comprising:
   a force deliverer drive component that moves at a first speed and a first acceleration while delivering a drive force;
   a deformation force deliverer to which said drive force is delivered and that moves simultaneously with said force deliver drive component at said first speed and said first acceleration to deliver deformation force to a test object; and
   a test object response determiner that determines a deformation response of said test object to said deformation force, said test object response determiner comprising:
      recorded drive component current versus test object deformation calibration data for a plurality of drive forces and said test object; and
      a computer processor programmed to use said calibration data for said plurality of drive forces to transform measured test object response data into generated test object response data,
   wherein said generated test object response data comprises test object deformation position versus deformation force data.

2. An apparatus for determining test object deformation response as described in claim 1 further comprising an input adjuster that adjusts an input that affects motion of said deformation force deliverer so as to meet at least one constraint.

3. An apparatus for determining test object deformation response as described in claim 1 wherein said at least one constraint comprises a test object deformation speed constraint.

4. An apparatus for determining test object deformation response as described in claim 1 wherein said at least one constraint comprises a test object deformation acceleration constraint.

5. An apparatus for determining test object deformation response as described in claim 1 wherein said input adjuster comprises a servo-controller and a linear encoder.

6. An apparatus for determining test object deformation response as described in claim 2 wherein said generated test object response data comprises speed versus deformation position data.

7. An apparatus for determining test object deformation response as described in claim 6 wherein said at least one constraint comprises a test object deformation force constraint.

8. An apparatus for determining test object deformation response as described in claim 6 wherein said input adjuster comprises said recorded calibration data and a servo-controller.

9. An apparatus for determining test object deformation response as described in claim 6 wherein said test object response determiner comprises a linear encoder.

10. An apparatus for determining test object deformation response as described in claim 1 wherein said force deliverer drive is powered with a constant current while a drive component thereof moves at said first speed and said first acceleration while delivering said drive force.

11. An apparatus for determining test object deformation response as described in claim 10 wherein said generated test object response data comprises test object deformation speed versus test object deformation position data.

12. An apparatus for determining test object deformation response as described in claim 1 wherein said force deliverer drive is powered with a varying current while a drive component thereof moves at said first speed and said first acceleration while delivering said drive force.

13. An apparatus for determining test object deformation response as described in claim 1 wherein said deformation force deliverer drive comprises a linear actuator component.

14. An apparatus for determining test object deformation response as described in claim 13 wherein said linear actuator comprises a voice coil linear actuator.

15. An apparatus for determining test object deformation response as described in claim 14 wherein said voice coil linear actuator comprises a moving voice coil linear actuator.

16. An apparatus for determining test object deformation response as described in claim 1 wherein said test object comprises a force activated switch dome.

17. An apparatus for determining test object deformation response as described in claim 1 wherein said test object response comprises hardness-related response.

18. An apparatus for determining test object deformation response as described in claim 1 wherein said test object response comprises elasticity response.

19. An apparatus for determining test object deformation response as described in claim 1 wherein said test object response comprises cyclical response.

20. An apparatus for determining test object deformation response as described in claim 1 wherein said deformation force deliverer repeatedly delivers said deformation force to said test object to determine cyclical failure response.

21. An apparatus for determining test object deformation response, comprising:
   a linear actuator that moves a deformation force deliverer that delivers deformation force to a test object;
   a test object response determiner that determines a response of said test object to said deformation force;
   determined information relating drive component current, test object deformation, and drive force for said test object, said determined information determined from a plurality of known deformation forces; and a computer processor forming at least part of said test object response determiner, said computer processor programmed to use said determined data to transform measured test object response data into generated test object response data.

22. An apparatus for determining test object deformation response as described in claim 21 further comprising an input adjuster that adjusts an input that affects motion of said deformation force deliverer so as to meet at least one constraint.

23. An apparatus for determining test object deformation response as described in claim 22 wherein said said generated test object response data comprises test object deformation position versus deformation force data.

24. An apparatus for determining test object deformation response as described in claim 22 wherein said at least one constraint comprises a test object deformation speed constraint.

25. An apparatus for determining test object deformation response as described in claim 22 wherein said at least one constraint comprises a test object deformation acceleration constraint.

26. An apparatus for determining test object deformation response as described in claim 22 wherein said input adjuster comprises a linear encoder and a servo-controller.

27. An apparatus for determining test object deformation response as described in claim 22 wherein said test object response determiner comprises said determined information.

28. An apparatus for determining test object deformation response as described in claim 22 wherein said generated test object response data comprises test object speed versus test object deformation position data.

29. An apparatus for determining test object deformation response as described in claim 28 wherein said at least one constraint comprises a test object deformation force constraint.

30. An apparatus for determining test object deformation response as described in claim 28 wherein said input adjuster comprises a servo-controller.

31. An apparatus for determining test object deformation response as described in claim 28 wherein said test object response determiner comprises a linear encoder.

32. An apparatus for determining test object deformation response as described in claim 21 wherein said linear actuator is powered with a varying current while delivering a drive force.

33. An apparatus for determining test object deformation response as described in claim 32 wherein said said generated test object response data comprises test object deformation position versus deformation force data.

34. An apparatus for determining test object deformation response as described in claim 32 wherein said generated test object response data comprises test object deformation speed versus test object deformation position data.

35. An apparatus for determining test object deformation response as described in claim 21 wherein said linear actuator is powered with a constant current while delivering a drive force.

36. An apparatus for determining test object deformation response as described in claim 35 wherein said said generated test object response data comprises test object deformation position versus deformation force data.

37. An apparatus for determining test object deformation response as described in claim 35 wherein said generated test object response comprises test object deformation speed versus test object deformation position data.

38. An apparatus for determining test object deformation response as described in claim 21 wherein a drive component of said linear actuator moves at a first speed and a first acceleration.

39. An apparatus for determining test object deformation response as described in claim 38 wherein said deformation force deliverer moves at said first speed and said first acceleration simultaneously with said drive component.

40. An apparatus for determining test object deformation response as described in claim 21 wherein said test object comprises a force activated switch dome.

41. An apparatus for determining test object deformation response as described in claim 21 wherein said test object response comprises hardness related response.

42. An apparatus for determining test object deformation response as described in claim 21 wherein said test object response comprises elasticity response.

43. An apparatus for determining test object deformation response as described in claim 21 wherein said test object response comprises cyclical response.

44. An apparatus for determining test object deformation response as described in claim 21 wherein said deformation force deliverer repeatedly delivers said deformation force to said test object to determine cyclical failure response.

45. An apparatus for determining test object deformation response as described in claim 1 wherein said measured test object response data comprises measured deformation position data, and known current.

46. An apparatus for determining test object deformation response as described in claim 1 wherein said recorded drive component current versus test object deformation calibration data comprises numerical parameters of a mathematical relationship.

47. An apparatus for determining test object deformation response as described in claim 21 wherein said measured test object response data comprises measured deformation position data, and known current.

48. An apparatus for determining test object deformation response as described in claim 21 wherein said determined information comprises recorded drive component current versus test object deformation calibration data for a plurality of drive forces.

49. An apparatus for determining test object deformation response as described in claim 21 wherein said determined information comprises a mathematical relationship usable to generate force from said measured test object response data.

* * * * *